(12) United States Patent
Beavers et al.

(10) Patent No.: US 7,393,850 B2
(45) Date of Patent: Jul. 1, 2008

(54) SUBSTITUTED PYRAZOLES

(75) Inventors: Mary Pat Beavers, New Hope, PA (US); J. Guy Breitenbucher, Escondido, CA (US); Hui Cai, San Diego, CA (US); James P. Edwards, San Diego, CA (US); Cheryl A. Grice, Carlsbad, CA (US); Darin J. Gustin, Half Moon Bay, CA (US); Haripada Khatuya, San Diego, CA (US); Steven P. Meduna, San Diego, CA (US); Barbara A. Pio, Hillsborough, NJ (US); Kevin L. Tays, Cardiff, CA (US); Jianmei Wei, San Diego, CA (US)

(73) Assignee: Ortho McNeil Pharmaceutical, Inc.DE (US)

(*) Notice: Subject to any disclaimer, the term of this patent is extended or adjusted under 35 U.S.C. 154(b) by 0 days.

(21) Appl. No.: 11/517,212

(22) Filed: Sep. 7, 2006

(65) Prior Publication Data

US 2007/0021437 A1  Jan. 25, 2007

Related U.S. Application Data

(62) Division of application No. 09/928,122, filed on Aug. 10, 2001.

(60) Provisional application No. 60/225,138, filed on Aug. 14, 2000.

(51) Int. Cl.
  *A61K 31/4965* (2006.01)
  *C07D 401/02* (2006.01)
  *C07D 403/04* (2006.01)

(52) U.S. Cl. .................. 514/254.06; 514/254.07; 544/362; 544/368; 544/371

(58) Field of Classification Search ............ 514/254.06, 514/254.07; 544/362, 368, 371
See application file for complete search history.

(56) References Cited

U.S. PATENT DOCUMENTS

| | | | |
|---|---|---|---|
| 3,994,890 | A | 11/1976 | Fujimura et al. |
| 4,500,525 | A | 2/1985 | Winters et al. |
| 5,264,576 | A | 11/1993 | Shutske et al. |
| 5,599,815 | A | 2/1997 | Fukuda et al. |
| 5,776,718 | A | 7/1998 | Palmer et al. |
| 5,830,850 | A | 11/1998 | Gelb et al. |
| 5,976,858 | A | 11/1999 | Palmer et al. |
| 6,020,336 | A | 2/2000 | Lavielle et al. |
| 6,030,946 | A | 2/2000 | Klaus et al. |
| 6,046,204 | A | 4/2000 | Cooper et al. |
| 6,214,813 | B1 | 4/2001 | Zhang et al. |
| 6,287,840 | B1 | 9/2001 | Palmer et al. |
| 2002/0040020 | A1* | 4/2002 | Breitenbucher et al. ..... 514/218 |
| 2007/0004754 | A1* | 1/2007 | Beavers et al. ......... 514/254.06 |
| 2007/0004755 | A1* | 1/2007 | Beavers et al. ......... 514/254.06 |
| 2007/0010530 | A1* | 1/2007 | Beavers et al. ......... 514/254.05 |

FOREIGN PATENT DOCUMENTS

| | | |
|---|---|---|
| AU | 199714432 | 7/1997 |
| EP | 0254241 A | 1/1988 |
| EP | 382637 B1 | 7/1993 |
| EP | 502786 B1 | 4/1996 |
| EP | 0747049 A1 | 12/1996 |
| EP | 0902027 A1 | 3/1999 |
| EP | 655248 B1 | 9/1999 |
| GB | 1489280 A | 10/1977 |
| JP | 50116470 A | 9/1975 |
| JP | 52014765 A | 2/1977 |
| WO | WO 94/18197 A1 | 8/1994 |
| WO | WO 95/23222 A1 | 8/1995 |
| WO | WO 96/30353 A1 | 10/1996 |
| WO | WO 97/21439 A1 | 6/1997 |
| WO | WO 97/40066 A1 | 10/1997 |
| WO | WO 9856785 A | 12/1998 |
| WO | WO 99/24460 A2 | 5/1999 |
| WO | WO 99/48911 A1 | 9/1999 |
| WO | WO 99/58153 A1 | 11/1999 |
| WO | WO 00/49008 A1 | 8/2000 |
| WO | WO 00/51998 A1 | 9/2000 |
| WO | WO 00/55144 A1 | 9/2000 |
| WO | WO 01/09110 A1 | 2/2001 |
| WO | WO 01/19796 A1 | 3/2001 |
| WO | WO 01/40204 A1 | 6/2001 |

OTHER PUBLICATIONS

Palmer, J.T. et al. Vinyl Sulfones as Mechanism-Based Cysteine Protease Inhibitors. J. Med. Chem. 1995, 38(17), 3193-3196.

Bromme, D. et al., "Peptidyl vinyl sulphones: a new class of potent and selective cysteine protease inhibitors," Biochem. J. 1996, 315, 85-89.

McGrath, M.E. et al., "Crystal structure of human cathepsin S," Protein Sci. 1998, 7(6), 1294-1302.

(Continued)

*Primary Examiner*—James O. Wilson
*Assistant Examiner*—Ebenezer Sackey

(57) ABSTRACT

Substituted pyrazoles, methods of manufacturing them, compositions containing them, and methods of using them to treat, for example, autoimmune diseases mediated by cathepsin S.

38 Claims, No Drawings

OTHER PUBLICATIONS

Nerenberg, J.B. et al., "Design and Synthesis of N-Alkylated Saccharins as Selective α-1A Adrenergic Receptor Antagonists," Boorg. Med. Chem. Lett. 1998, 8, 2467-2472.

Honey, K. et al., "Role of Lysosomal Cysteine Proteinases in Antigen Presentation on CD4 T Cells," Inflammation Research 2001, Supp. 3, 50, S159, abstr. Oct. 2001.

Li, W. et al., "Tissue Specific Expression of Cathepsins and Antigen Presentation," Inflammation Research 2001, Supp. 3, 50, S159, abstr. Oct. 2002.

Magill, C. et al., "Cysteine Proteases in Antigen Presentation and Models of Inflammation," Inflammation Research 2001, Supp. 3, 50, S159, abstr. Oct. 2003.

Allen, E.M. et al, "Reversible Cathepsin S (CATS) Inhibitors Block Invariant Chain Degradation Both In Vitro and In Vivo," Inflammation Research 2001, Supp. 3, 50, S159, abstr. Oct. 2004.

Podolin, P.L. et al., "Inhibition of Cathepsin S Blocks Invariant Chain Processing and Antigen-Induced Proliferation in Vitro, and Reduces the Severity of Collagen-Induced Arthritis In Vivo," Inflammation Research 2001, Supp. 3, 50, S159, abstr. Oct. 2005.

Spero, D. et al., "Design and Synthesis of Novel Cathepsin S Inhibitors," Inflammation Research 2001, Supp. 3, 50, S206, abstr. 079.

Andronati, S.A. et al., "Synthesis of 1-{4-(4-phenyl-1-piperazinyl)butyl]1,2-dihydro-3H-1,4-benzodiazepin-2-ones and 1H-indazoles and their affinity for benzodiazepine receptors," Chemical Abstracts No. (CAN) 122:314528 (1994) 8:126-131.

Bromme, D. et al., "High level expression and crystallization of recombinant human cathepsin S," Protein Sci. 1996, 5, 789-791.

Kirschke, H. et al., "Cathepsin S," Handbook of Proteolytic Enzymes; Barrett, A.J.; Rawlings, N.D.; Woessner, J.F., Editors, Academic Press (1998) 621-624.

Nakagawa, T.Y. et al., "Impaired Invariant Chain Degradation and Antigen Presentation and Diminished Collagaen-Induced Arthritis in Cathepsin S Null Mice," Immunity 1999, 10, 207-217.

Riese, R.J. et al., "Cathepsin S Activity Regulates Antigen Presentation and Immunity," J. Clin. Invest. 1998, 101(11), 2351-2363.

Shi, G.P. et al., "Cathepsin S Required for Normal MHC Class II Peptide Loading and Germinal Center Development," Immunity 1999, 10, 197-206.

Singh, P. et al., "Quantitative Structure-Activity Relationship Studies on a New Class of Antihypertensive Agents: Derivatives of 3-Aryl-4,5,6,7-tetrahydro-1H-pyrazolo[4,3-c]pyridine," Quant. Struct.-Act. Relat. 1990, 9, 29-32.

Winters, G. et al., "Synthesis, in Vitro [3H]Prazosin Displacement, and in Vivo Activity of 3-Aryl-4,5,6,7-tetrahydropyrazolo[4,3-c]pyridines, a New Class of Antihypertensive Agents," J. Med. Chem. 1985, 28(7), 934-940.

Andronati, "Synthesis of 3-aryl-1-[4-phenyl-1-piperazinyl)butyl]iondazole derivatives and their affinity to 5-HT1A serotonin and dopamine D1 receptors," Pharmazie 1999, 54(2), 99-101.

Fujimura, Y. et al. "Indazole derivatives", Database CA Online, Chemical Abstracts Service, STN database accession No. 87:53281, XP002193796 abstract (Feb. 3, 1977) relating to JP 52014765 (Chugai Pharmaceutical Co., Ltd.).

Fujimura, Y. et al. "Indazole derivatives." Database CA Online, Chemical Abstracts Service, STN database accession No. 84:59450, XP002193797 abstract (Sep. 11, 1975) relating to JP 50116470 (Chugai Pharmaceutical Co., Ltd.).

Nakatsuka, M. et al. "Preparation of pyrazole derivatives as immunosuppressants." Database CA Online, Chemical Abstracts Service, STN database accession No. 130:52417, XP002193692 abstract (Dec. 17, 1998) relating to WO9856785 (Sumitomo Pharmaceuticals Co., Ltd.).

Leroy et al. Cathepsin S Inhibitors. Exp. Opin. Ther. Patents 2004, 14(3), 301-311.

Eberlein-Konig, et al. Immunohistochemical investigation of the cellular infiltrates at the sites of allergoid-induced late-phase cutaneous reactions associated with polle allergen-specific immunotherapy. Clin. Exp. Allergy 1999, 29(12), 1641-1647.

Gaga, et al. Eosinophil activation and T lymphocyte infiltration in allergin-induced late phase skin reactions and classical delayed-type hypersensitivity. J. Immunol. 1991, 147, 816-822.

Chapman, H.A. et al. Emerging Roles for Cysteine Proteases in Human Biology. Ann. Rev. Physiol. 1997, 59, 63-88.

Chapman, H.A. Endosomal Proteolysis and MHC Class II Function. Curr. Opin. Immunol. 1998, 10, 93-102.

Maurer, D. et al. Fce Receptor I on Dendritic Cells Delivers IgE-Bound Multivalent Antigens into a Cathepsin S-Dependent Pathway of MHC Class II Presentation. J. Immunol. 1998, 161, 2731-2739.

Nakagawa, T.Y. et al. The role of lysosomal proteinases in MHC class II-mediated antigen processing and presentation. Immunol. Rev. 1999, 172, 121-129.

Riese, R.J. et al. Cathepsins and Compartmentalization in Antigen Presentation. Curr. Opin. Immunol. 2000, 12, 107-113.

Villadangos, J.A. et al. Degradation of Mouse Invariant Chain: Roles of Cathepsins S and D and the Influence of Major Histocompatability Complex Polymorphism. J. Ex. Med. 1997, 186(4), 549-560.

Villadangos, J.A. et al. Proteases Involved in MHC Class II Antigen Presentation. Immunol. Rev. 1999, 172, 109-120.

Villadangos, J.A. et al. Proteolysis in MHC Class II Antige Presentation: Who's in Charge? Immunity 2000, 12, 233-239.

Paluchowska et al. Structure-activity relationship studies of CNS agents. 40. Effect of the amide fragment on 5-HT1A receptor activity of some analogs of MP 3022. Pol. J. Pharmacol. 1999, 51(5), 415-421.

Paluchowska et al. Influence of the aliphatic spacer length on the 5-HT1A receptor activity of new arylpiperazines with an indazole system. Pol. J. Pharmacol. 2000, 52(3), 209-216.

Reise, R.J. et al. Essential Role for cathepsin S in MHC Class II-Associated Invariant Chain Processing and Peptide Loading. Immunity 1996, 4, 357-366.

Link Jo et al., Advances in Cathepsin S Inhibitor Design, *Current Opinion Drug Discovery Development*, vol. 9(4), pp. 471-481, 2006.

Semper et al., Dendritic Cells in Allergy, *Dendritic Cells: Biology and Clinical App.*, Ch.24, pp. 435-456, 1999.

Von Bubnoff et al., Antigen-presenting cells in allergy, *J. Allergy Clin Immunol*, pp. 329-338, 2001.

Novak et al., Dendritic Cells in Allergy, *Allergy*, vol. 54, pp. 792-801, 1999.

\* cited by examiner

SUBSTITUTED PYRAZOLES

This application is a division of U.S. patent application Ser. No. 09/928,122, filed Aug. 10, 2001, that is incorporated herein by reference in its entirety, and application Ser. No. 09/928,122 in turn claims the benefit under 35 U.S.C. § 119 (e) of U.S. Provisional Application Ser. No. 60/225,138, filed on Aug. 14, 2000.

FIELD OF THE INVENTION

This invention relates to a series of substituted pyrazoles, pharmaceutical compositions containing these compounds, and intermediates used in their manufacture, and methods of using them.

BACKGROUND OF THE INVENTION

Cathepsin S (EC 3.4.22.27) is a cysteine protease of the papain family found primarily in lysosomes (Bromme, D.; McGrath, M. E. High Level Expression and Crystallization of Recombinant Human Cathepsin S. *Protein Science* 1996, 5, 789-791).

The role of cathepsin S in the immune response is anticipated by its tissue distribution: cathepsin S is found primarily in lymphatic tissues, lymph nodes, the spleen, B lymphocytes, and macrophages (Kirschke, H. Chapter 211. Cathepsin S. In Handbook of Proteolytic Enzymes. Barrett, A. J.; Rawlings, N. D.; Woessner, J. F., Eds. San Diego: Academic Press, 1998. pp. 621-624.). Cathepsin S inhibitors have been shown in animal models to modulate antigen presentation and are effective in an animal model of asthma (Riese, R. J.; Mitchell, R. N.; Villadangos, J. A.; Shi, G.-P.; Palmer, J. T.; Karp, E. R.; De Sanctis, G. T.; Ploegh, H. L.; Chapman, H. A. Cathepsin S Activity Regulates Antigen Presentation and Immunity. *J. Clin. Invest.* 1998, 101, 2351-2363 and Shi, G.-P.; Villadangos, J. A.; Dranoff, G.; Small, C.; Gu, L.; Haley, K. J.; Riese, R.; Ploegh, H. L.; Chapman, H. A. Cathepsin S Required for Normal MHC Class II Peptide Loading and Germinal Center Development. *Immunity* 1999, 10, 197-206.).

Mice in which the gene encoding cathepsin S has been knocked out are less susceptible to collagen-induced arthritis and their immune systems have an impaired ability to respond to antigens (Nakagawa, T. Y.; Brissette, W. H.; Lira, P. D.; Griffiths, R. J.; Petrushova, N.; Stock, J.; McNeish, J. D.; Eastman, S. E.; Howard, E. D.; Clarke, S. R. M.; Rosloniec, E. F.; Elliott, E. A.; Rudensky, A. Y. Impaired Invariant Chain Degradation and Antigen Presentation and Diminished Collagen-induced Arthritis in Cathepsin S Null Mice. *Immunity* 1999, 10, 207-217).

These data demonstrate that compounds that inhibit the proteolytic activity of human cathepsin S should find utility in the treatment of chronic autoimmune diseases including, but not limited to, lupus, rheumatoid arthritis, and asthma; and have potential utility in modulating the immune response to tissue transplantation.

There are a number of cathepsin S inhibitors reported in the literature. The most important patents are listed below.

Certain dipeptidyl nitriles are claimed by Novartis as cathepsin S inhibitors in: Altmann, et. al. WO-99/24460.

Dipeptidyl vinyl sulfones are claimed by Arris (now Axys) as cysteine protease (including cathepsin S) inhibitors in: Palmer, et. al. U.S. Pat. No. 5,976,858.

Certain peptidyl sulfonamides are claimed by Arris/Axys as cysteine protease (including cathepsin S) inhibitors in: Palmer, et. al. U.S. Pat. No. 5,776,718 (assigned to Arris, now Axys) & Klaus, et. al. U.S. Pat. No. 6,030,946 (assigned to Axys).

Compounds somewhat similar to those of the present invention are described in the following references.

Winters, et. al. (Winters, G.; Sala, A.; Barone, D.; Baldoli, E. *J. Med. Chem.* 1985, 28, 934-940; Singh, P.; Sharma, R. C. *Quant. Struct.-Act. Relat.* 1990, 9, 29-32; Winters, G.; Sala, A.; Barone, D. in U.S. Pat. No. 4,500,525 (1985)) have described bicyclic pyrazoles of the type shown below. R never contains a heterocyclic ring and no protease inhibitor activity is ascribed to these molecules; they are described as α1-adrenergic receptor modulators.

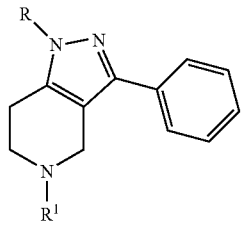

Shutske, et. al. claim the bicylic pyrazoles below. The pyridine ring is aromatic in their system (Shutske, G. M.; Kapples, K. J.; Tomer, J. D. U.S. Pat. No. 5,264,576 (1993)). Although reference is made to R being a linker to a heterocycle, the claims specify only R=hydrogen. The compounds are referred to as serotonin reuptake inhibitors.

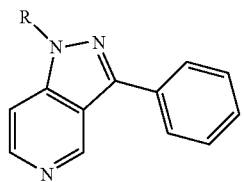

The compound 2-[4-[4-(3-methyl-5-phenyl-1H-pyrazol-1-yl)butyl]-1-piperazinyl]-pyrimidine is known from EP-382637, which describes pyrimidines having anxiolytic properties. This compound and analogs are further described in EP-502786 as cardiovascular and central nervous system agents. Pharmaceutical formulations with such compounds are disclosed in EP-655248 for use in the treatment of gastric secreation and as anti-ulcer agents. WO-9721439 describes medicaments with such compounds for treating obsessive-compulsive disorders, sleep apnea, sexual dysfunctions, emesis and motion sickness.

The compounds 5-methyl-3-phenyl-1-[4-(4-phenyl-1-piperazinyl)butyl]-1H-indazole and 5-bromo-3-(2-chlorophenyl)-1-[4-(4-phenyl-1-piperazinyl)butyl]-1H-indazole, in particular the hydrochloride salts thereof, are known from WO-9853940 and CA 122:314528, where these and similar compounds are described as kinase inhibitors in the former reference and possessing affinity for benzodiazepine receptors in the latter reference.

SUMMARY OF THE INVENTION

The present invention concerns compounds which can be represented by formula (I):

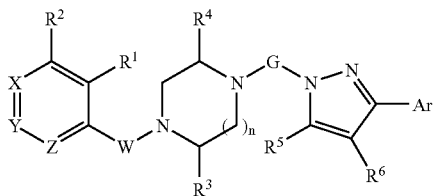

(I)

wherein:

$R^1$ is hydrogen, azido, halogen, $C_{1-5}$ alkoxy, hydroxy, $C_{1-5}$ alkyl, $C_{2-5}$ alkenyl, cyano, nitro, $R^7R^8N$, $C_{2-8}$ acyl, $R^9OC=O$, $R^{10}R^{11}NC=O$, or $R^{10}R^{11}NSO_2$; or $R^1$ is taken together with W as described below;

$R^2$ is hydrogen, halogen, $C_{1-5}$ alkoxy, $C_{1-5}$ alkyl, $C_{2-5}$ alkenyl, $C_{1-5}$ haloalkyl, cyano, or $R^{48}R^{49}N$;
  alternatively, $R^1$ and $R^2$ can be taken together to form an optionally substituted 5- to 7-membered carbocyclic or heterocyclic ring, which ring may be unsaturated or aromatic;

each of $R^3$ and $R^4$ is independently hydrogen or $C_{1-5}$ alkyl;

each of $R^5$ and $R^6$ is independently hydrogen, $C_{1-5}$ alkyl, $C_{2-5}$ alkenyl, $C_{1-5}$ alkoxy, $C_{1-5}$ alkylthio, halogen, or a 4-7 membered carbocyclyl or heterocyclyl;
  alternatively, $R^5$ and $R^6$ can be taken together to form an optionally substituted 5- to 7-membered carbocyclic or heterocyclic ring, which ring may be unsaturated or aromatic, and may be optionally substituted with between one and three substituents independently selected from halo, cyano, amino, nitro, $R^{40}$, $R^{40}O—$, $R^{40}S—$, $R^{40}O(C_{1-5}$ alkylene)-, $R^{40}O(C=O)—$, $R^{40}(C=O)—$, $R^{40}(C=S)—$, $R^{40}(C=O)O—$, $R^{40}O(C=O)(C=O)—$, $R^{40}SO_2$, $NHR^{62}(C=NH)—$, $NHR^{62}SO_2—$, and $NHR^{62}(C=O)—$;

$R^{40}$ is H, $C_{1-5}$ alkyl, $C_{2-5}$ alkenyl, phenyl, benzyl, phenethyl, $C_{1-5}$ heterocyclyl, $(C_{1-5}$ heterocyclyl)$C_{1-5}$ alkylene, amino, or mono- or di($C_{1-5}$ alkyl)amino, or $R^{58}OR^{59}—$, wherein $R^{58}$ is H, $C_{1-5}$ alkyl, $C_{2-5}$ alkenyl, phenyl, benzyl, phenethyl, $C_{1-5}$ heterocyclyl, or $(C_{1-5}$ heterocyclyl)$C_{1-6}$ alkylene and $R^{59}$ is $C_{1-5}$ alkylene, phenylene, or divalent $C_{1-5}$ heterocyclyl; and $R^{62}$ can be H in addition to the values for $R^{40}$;

$R^7$ is hydrogen, $C_{1-5}$ alkyl, $C_{3-5}$ alkenyl, phenyl, naphthyl, $C_{1-5}$ heterocyclyl, $C_{2-8}$ acyl, aroyl, $R^{27}OC=O$, $R^{28}R^{29}NC=O$, $R^{27}SO$, $R^{27}S_2$, or $R^8$ is hydrogen, $C_{1-5}$ alkyl, $C_{3-5}$ alkenyl, phenyl, or $C_{1-5}$ heterocyclyl;
  alternatively, $R^7$ and $R^8$ can be taken together to form an optionally substituted 4- to 7-membered heterocyclic ring, which ring may be saturated, unsaturated or aromatic;

$R^9$ is $C_{1-5}$ alkyl, phenyl, naphthyl, or $C_{1-5}$ heterocyclyl;

$R^{21}$ is hydrogen, $C_{1-5}$ alkyl, $C_{3-5}$ alkenyl, phenyl, naphthyl, $C_{1-5}$ heterocyclyl, $C_{2-18}$ acyl, aroyl, $R^{30}OC=O$, $R^{31}R^{32}NC=O$, $R^{30}SO$, $R^{30}SO_2$, or $R^{31}R^{32}NSO_2$;

$R^{22}$ is hydrogen, $C_{1-5}$ alkyl, $C_{3-5}$ alkenyl, phenyl, or $C_{1-5}$ heterocyclyl;
  alternatively, $R^{21}$ and $R^{22}$ can be taken together to form an optionally substituted 4- to 7-membered heterocyclic ring, which ring may be saturated, unsaturated or aromatic;

each of $R^{23}$, $R^{26}$, $R^{27}$, $R^{30}$, $R^{33}$, $R^{44}$, $R^{45}$, and $R^{50}$ is $C_{1-5}$ alkyl, phenyl, naphthyl, or $C_{1-5}$ heterocyclyl;

$R^{24}$ is hydrogen, $C_{1-5}$ alkyl, $C_{3-5}$ alkenyl, phenyl, naphthyl, $C_{1-5}$ heterocyclyl, $C_{2-8}$ acyl, aroyl, $R^{33}OC=O$, $R^{34}R^{35}NC=O$, $R^{33}SO$, $R^{33}SO_2$, or $R^{34}R^{35}NSO_2$;

$R^{25}$ is hydrogen, $C_{1-5}$ alkyl, $C_{3-5}$ alkenyl, phenyl, or $C_{1-5}$ heterocyclyl;
  alternatively, $R^{24}$ and $R^{25}$ can be taken together to form an optionally substituted 4- to 7-membered heterocyclic ring, which ring may be saturated, unsaturated or aromatic;

each of $R^{10}$ and $R^{11}$ is independently hydrogen, $C_{1-5}$ alkyl, $C_{2-5}$ alkenyl, phenyl, or $C_{1-5}$ heterocyclyl;
  alternatively, $R^{10}$ and $R^{11}$ can be taken together to form an optionally substituted 4- to 7-membered heterocyclic ring, which ring may be saturated, unsaturated or aromatic;

each of $R^{28}$, $R^{29}$, $R^{31}$, $R^{32}$, $R^{34}$, $R^{35}$, $R^{46}$, $R^{47}$, $R^{51}$ and $R^{52}$ is independently hydrogen, $C_{1-5}$ alkyl, phenyl, or $C_{1-5}$ heterocyclyl;
  alternatively, $R^{28}$ and $R^{29}$, $R^{31}$ and $R^{32}$, $R^{34}$ and $R^{35}$, $R^{46}$ and $R^{47}$, or $R^{51}$ and $R^{52}$, independently, can be taken together to form an optionally substituted 4- to 7-membered heterocyclic ring, which ring may be saturated, unsaturated or aromatic;

n is 1 or 2;

G represents $C_{3-6}$ alkenediyl or $C_{3-6}$ alkanediyl, optionally substituted with hydroxy, halogen, $C_{1-5}$ alkyl, $C_{1-5}$ alkoxy, oxo, hydroximino, $CO_2R^{60}$, $R^{60}R^{61}NCO_2$, (L)-$C_{1-4}$ alkylene-, (L)-$C_{1-5}$ alkoxy, $N_3$, or [(L)-$C_{1-5}$ alkylene]amino;

each of $R^{60}$ and $R^{61}$ is independently hydrogen, $C_{1-5}$ alkyl, $C_{3-5}$ alkenyl, phenyl, benzyl, phenethyl, or $C_{1-5}$ heterocyclyl; alternatively, $R^{60}$ and $R^{61}$ can be taken together to form an optionally substituted 4- to 7-membered heterocyclic ring, which ring may be saturated, unsaturated or aromatic;

L is amino, mono- or di-$C_{1-15}$ alkylamino, pyrrolidinyl, morpholinyl, piperidinyl, homopiperidinyl, or piperazinyl, where available ring nitrogens may be optionally substituted with $C_{1-5}$ alkyl, benzyl, $C_{2-5}$ acyl, $C_{1-5}$ alkylsulfonyl, or $C_{1-5}$ alkyloxycarbonyl;

X is nitrogen or $R^{12}C$;
Y is nitrogen or $R^{13}C$
Z is nitrogen or $R^{14}C$ $R^{12}$ is hydrogen, halogen, $C_{1-5}$ alkoxy, $C_{1-5}$ alkyl, $C_{2-5}$ alkenyl, cyano, nitro, $R^{21}R^{22}N$, $C_{2-8}$ acyl, $C_{1-5}$ haloalkyl, $C_{1-5}$ heterocyclyl, $(C_{1-5}$ heterocyclyl)$C_{1-5}$ alkylene, $R^{23}OC=O$, $R^{23}O(C=O)NH—$, $R^{23}SO$, $R^{22}NHCO—$, $R^{22}NH(C=O)NH—$, $R^{23}(C_{1-4}$ alkylene)$NHCO—$, $R^{23}SO_2$, or $R^{23}SO_2NH—$;

$R^{13}$ is hydrogen, halogen, $C_{1-5}$ alkoxy, $C_{1-5}$ alkyl, $C_{2-5}$ alkenyl, cyano, nitro, $R^{42}R^{43}N$, $C_{2-8}$ acyl, $C_{1-5}$ haloalkyl, $C_{1-5}$ heterocyclyl, $(C_{1-5}$ heterocyclyl)$C_{1-5}$ alkylene, $R^{44}OC=O$, $R^{44}O(C=O)NH—$, $R^{44}SO$, $R^{43}NHCO—$, $R^{43}NH(C=O)NH—$, $R^{44}(C_{1-4}$ alkylene)$NHCO—$, $R^{44}SO_2$, or $R^{44}SO_2NH—$;

$R^{14}$ is hydrogen, halogen, $C_{1-5}$ alkoxy, $C_{1-5}$ alkyl, $C_{2-5}$ alkenyl, cyano, nitro, $R^{24}R^{25}N$, $C_2$ acyl, $C_{1-5}$ haloalkyl, $C_{1-5}$ heterocyclyl, $(C_{1-5}$ heterocyclyl)$C_{1-5}$ alkylene, $R^{26}OC=O$, $R^{26}O(C=O)NH—$, $R^{26}SO$, $R^{25}NHCO—$, $R^{25}NH(C=O)NH—$, $R^{26}(C_{1-4}$ alkylene)$NHCO—$, $R^{26}SO_2$, or $R^{26}SO_2NH—$;
  alternatively, $R^{12}$ and $R^{13}$ or $R^{12}$ and $R^2$ or $R^{13}$ and $R^{14}$ can be taken together to form an optionally substituted 5- to 6-membered carbocyclic or heterocyclic ring, which ring may be unsaturated or aromatic;

Ar represents a monocyclic or bicyclic aryl or heteroaryl ring, optionally substituted with between 1 and 3 substituents selected from halogen, $C_{1-5}$ alkoxy, $C_{1-5}$ alkyl, $C_{2-5}$ alkenyl, cyano, azido, nitro, $R^{15}R^{16}N$, $R^{17}SO_2$, $R^{17}S$, $R^{17}SO$, $R^{17}OC=O$, $R^{15}R^{16}NC=O$, $C_{1-5}$haloalkyl, $C_{1-5}$ haloalkoxy, $C_{1-5}$haloalkylthio, and $C_{1-5}$ alkylthio;

$R^{15}$ is hydrogen, $C_{1-5}$ alkyl, $C_{3-5}$ alkenyl, phenyl, benzyl, $C_{1-5}$ heterocyclyl, $C_{2-8}$ acyl, aroyl, $R^{53}OC=O$, $R^{54}R^{55}NC=O$, $R^{53}S$, $R^{53}SO$, $R^{53}SO_2$, or $R^{54}R^{55}NSO_2$;

$R^{16}$ is hydrogen, $C_{1-5}$ alkyl, $C_{3-5}$ alkenyl, phenyl, benzyl, or $C_{1-5}$ heterocyclyl;

alternatively, $R^{15}$ and $R^{16}$ can be taken together to form an optionally substituted 4- to 7-membered heterocyclic ring, which ring may be saturated, unsaturated or aromatic;

each of $R^{17}$ and $R^{53}$ is $C_{1-5}$ alkyl, phenyl, or $C_{1-5}$ heterocyclyl;

each of $R^{54}$ and $R^{55}$ is independently hydrogen, $C_{1-5}$ alkyl, $C_{2-5}$ alkenyl, phenyl, benzyl, or $C_{1-5}$ heterocyclyl;

alternatively, $R^{54}$ and $R^{55}$ can be taken together to form an optionally substituted 4- to 7-membered heterocyclic ring, which ring may be saturated, unsaturated or aromatic;

W represents $SO_2$, $C=O$, $CHR^{20}$, or a covalent bond; or W and $R^1$, taken together with the 6-membered ring to which they are both attached, form one of the following two formulae:

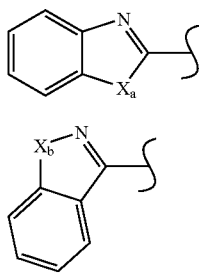

(I)(a)

(I)(b)

wherein $X_a$ is O, S, or N; and $X_b$ is O, S or $SO_2$;

$R^{20}$ is hydrogen, $C_{1-5}$ alkyl, phenyl, benzyl, naphthyl, or $C_{1-5}$ heterocyclyl;

$R^{42}$ is hydrogen, $C_{1-5}$ alkyl, $C_{3-5}$ alkenyl, phenyl, naphthyl, $C_{1-5}$ heterocyclyl, $C_{2-8}$ acyl, aroyl, $R^{45}OC=O$, $R^{46}R^{47}NC=O$, $R^{45}SO$, $R^{45}SO_2$, or $R^{46}R^{47}NSO_2$;

$R^{43}$ is hydrogen, $C_{1-5}$ alkyl, $C_{3-5}$ alkenyl, phenyl, or $C_{1-5}$ heterocyclyl;

alternatively, $R^{42}$ and $R^{43}$ can be taken together to form an optionally substituted 4- to 7-membered heterocyclic ring, which ring may be saturated, unsaturated or aromatic;

$R^{44}$ is $C_{1-5}$ alkyl, $C_{2-5}$ alkenyl, phenyl, naphthyl, or $C_{1-5}$ heterocyclyl;

$R^{48}$ is hydrogen, $C_{1-5}$ alkyl, $C_{3-5}$ alkenyl, phenyl, naphthyl, $C_{1-5}$ heterocyclyl, $C_{2-8}$ acyl, aroyl, $R^{50}OC=O$, $R^{51}R^{52}NC=O$, $R^{50}SO$, $R^{50}SO_2$, or $R^{51}R^{52}NSO_2$;

$R^{49}$ is hydrogen, $C_{1-5}$ alkyl, $C_{3-5}$ alkenyl, phenyl, or $C_{1-5}$ heterocyclyl;

alternatively, $R^{48}$ and $R^{49}$ can be taken together to form an optionally substituted 4- to 7-membered heterocyclic ring, which ring may be saturated, unsaturated or aromatic; and wherein each of the above hydrocarbyl or heterocarbyl groups, unless otherwise indicated, and in addition to any specified substituents, is optionally and independently substituted with between 1 and 3 substituents selected from methyl, halomethyl, hydroxymethyl, halo, hydroxy, amino, nitro, cyano, $C_{1-5}$ alkyl, $C_{1-5}$ alkoxy, —COOH, $C_{2-6}$ acyl, [di($C_{1-4}$ alkyl)amino]$C_{2-5}$ alkylene, [di($C_{1-4}$ alkyl)amino]$C_{2-5}$ alkyl-NH—CO—, and $C_{1-5}$ haloalkoxy;

or a pharmaceutically acceptable salt, ester, or amide thereof, including a stereoisomeric form thereof.

The disclosed compounds are high-affinity inhibitors of the proteolytic activity of human cathepsin S. For use in medicine, the preparation of pharmaceutically acceptable salts of compounds of formula (I) may be desirable.

Certain compounds of the present invention may have one stereogenic atom and may exist as two enantiomers. Certain compounds of the present invention may have two or more stereogenic atoms and may further exist as diastereomers. It is to be understood by those skilled in the art that all such stereoisomers and mixtures thereof in any proportion are encompassed within the scope of the present invention.

Another aspect of the invention provides pharmaceutical compositions comprising a compound of formula (I) and a pharmaceutically acceptable carrier. A further embodiment of the invention is a process for making a pharmaceutical composition comprising mixing a disclosed compound as described above, with a suitable pharmaceutically acceptable carrier.

The invention also contemplates pharmaceutical compositions comprising more than one compound of formula (I) and compositions comprising a compound of formula (I) and another pharmaceutically active agent.

The invention features a method of treating disorders or conditions mediated by the cathepsin S enzyme, in a subject in need thereof, comprising administering to the subject a therapeutically effective amount of any of the compounds or pharmaceutical compositions described above. If more than one active agent is administered, the therapeutically effective amount may be a jointly effective amount. The compounds described herein inhibit the protease activity of human cathepsin S, an enzyme involved in the immune response. In preferred embodiments, cathepsin S inhibition is selective. As such, the disclosed compounds and compositions are useful in the prevention, inhibition, or treatment of autoimmune diseases such as lupus, rheumatoid arthritis, and asthma, and for the prevention, inhibition, or treatment of tissue transplant rejection.

Additional features and advantages of the invention will become apparent from the detailed description below, including examples, and the appended claims.

DETAILED DESCRIPTION OF THE INVENTION

The invention features pyrazole compounds of formula (I), methods of making them, compositions containing them, and methods of using them to treat diseases and conditions, including those mediated by Cathepsin S.

A. TERMS

The following terms are defined below and by their usage throughout this disclosure.

"Alkyl" includes optionally substituted straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl.

"Alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention.

"Alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes an optionally substituted straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridge, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on.

"Heterocyclyl" includes optionally substituted aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 4 and 7 ring atoms, or between 5 and 6 ring atoms; there may be between 1 and 5 heteroatoms or heteroatom moieties in the ring, and preferably between 1 and 3. A heterocyclyl may be saturated, unsaturated, aromatic (e.g., heteroaryl), nonaromatic, or fused.

Heterocyclyl also includes fused, e.g., bicyclic, rings, such as those optionally condensed with an optionally substituted carbocyclic or heterocyclic five- or six-membered aromatic ring. For example, "heteroaryl" includes an optionally substituted six-membered heteroaromatic ring containing 1, 2 or 3 nitrogen atoms condensed with an optionally substituted five- or six-memebered carbocyclic or heterocyclic aromatic ring. Said heterocyclic five- or six-membered aromatic ring condensed with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

Examples of heterocyclyls include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino, and more preferably, piperidyl.

Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl.

"Acyl" refers to a carbonyl moiety attached to either a hydrogen atom (i.e., a formyl group) or to an optionally substituted alkyl or alkenyl chain, or heterocyclyl.

"Halo" or "halogen" includes fluoro, chloro, bromo, and iodo, and preferably chloro or bromo as a substituent.

"Alkanediyl" or "alkylene" represents straight or branched chain optionally substituted bivalent alkane radicals such as, for example, methylene, ethylene, propylene, butylene, pentylene or hexylene.

"Alkenediyl" represents, analogous to the above, straight or branched chain optionally substituted bivalent alkene radicals such as, for example, propenylene, butenylene, pentenylene or hexenylene. In such radicals, the carbon atom linking a nitrogen preferably should not be unsaturated.

"Aroyl" refers to a carbonyl moiety attached to an optionally substituted aryl or heteroaryl group, wherein aryl and heteroaryl have the definitions provided above. In particular, benzoyl is phenylcarbonyl.

As defined herein, two radicals, together with the atom(s) to which they are attached may form an optionally substituted 4- to 7-, 5- to 7-, or a 5- to 6-membered ring carbocyclic or heterocyclic ring, which ring may be saturated, unsaturated or aromatic. Said rings may be as defined above in the Summary of the Invention section. Particular examples of such rings are as follows in the next section.

"Pharmaceutically acceptable salts, esters, and amides" include carboxylate salts (e.g., $C_{1-8}$ alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1-19 which is incorporated herein by reference. Representative pharmaceutically acceptable amides of the invention include those derived from ammonia, primary $C_{1-6}$ alkyl amines and secondary di($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient or subject is a human.

"Composition" includes a product comprising the specified ingredients in the specified amounts as well as any product which results directly or indirectly from combinations of the specified ingredients in the specified amounts.

"Therapeutically effective amount" or "effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Concerning the various radicals in this disclosure and in the claims, three general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is G in formula (I) which links two rings.

Second, radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding divalent radicals such as alkylene, alkenylene, phenylene, and so on. Heterocarbyls include monovalent and divalent radicals containing carbon, hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, perfluoromethyl, and 3-iodocyclopentyl), hydroxyalkyl (such as hydroxymethyl, hydroxyethyl, 2-hydroxypropyl, aminoalkyl (such as aminomethyl, 2-aminoethyl, 3-aminopropyl, and 2-aminopropyl), nitroalkyl, alkylalkyl, and so on. A di($C_{1-6}$ alkyl)amino group includes independently selected alkyl groups, to form, for example, methylpropylamino and isopropylmethylamino, in addition dialkylamino groups having two of the same alkyl group such as dimethyl amino or diethylamino.

Third, only stable compounds are intended. For example, where there is an NR'R" group, and R can be an alkenyl group, the double bond is at least one carbon removed from the nitrogen to avoid enamine formation. Similarly, where a dashed line is an optional $sp^2$ bond, if it is absent, the appropriate hydrogen atom(s) is(are) included.

Preferred substitutions for Ar include methyl, methoxy, fluoromethyl, difluoromethyl, perfluoromethyl (trifluoromethyl), 1-fluoroethyl, 2-fluoroethyl, ethoxy, fluoro, chloro, and bromo, and particularly methyl, bromo, chloro, perfluoromethyl, perfluoromethoxy, methoxy, and fluoro. Preferred substitution patterns for Ar or $Ar_1$ are 4-substituted or 3,4-disubstituted phenyl.

Compounds of the invention are further described in the next section.

B. COMPOUNDS

The invention features compounds of formula (I) as described in the Summary section.

Preferred compounds include those wherein:
(a) $R^1$ is hydrogen, halogen, $C_{1-5}$ alkoxy, hydroxy, $C_{1-5}$ alkyl, cyano, nitro, $R^7R^8N$, $C_{2-8}$ acyl, or $R^{10}R^{11}NSO_2$;
(b) $R^1$ is halogen, cyano, nitro, $R^7R^8N$, or $R^{10}R^{11}NSO_2$;
(c) $R^2$ is hydrogen;
(d) each of $R^3$ and $R^4$ is independently hydrogen or $C_{1-3}$ alkyl;
(e) one of $R^3$ and $R^4$ is hydrogen;
(f) each of $R^3$ and $R^4$ is hydrogen;
(g) one of $R^5$ and $R^6$ is hydrogen and the other is a 5-7 membered carbocyclyl or heterocyclyl, optionally substituted;
(h) $R^5$ and $R^6$ taken together form a six-membered heterocyclyl;
(i) $R^5$ and $R^5$ taken together form pyridinyl, pyrimidinyl, or piperazinyl, optionally N-substituted with $R^{40}O(C=O)$ $(C=O)$—, $R^{40}SO_2$, $R^{40}NHCO_2$, $R^{40}(C=O)$—, or $R^{40}N(C=O)$—;
(j) each of $R^7$, $R^8$, $R^{21}$, $R^{22}$, $R^{24}$, and $R^{25}$ is independently hydrogen or $C_{1-5}$ alkyl; or, independently, each of $R^7$ and $R^8$, $R^{21}$ and $R^{22}$, and $R^{24}$ and $R^{25}$ can be taken together to form an optionally substituted 4- to 7-membered heterocyclic ring, which ring may be saturated, unsaturated or aromatic;
(k) at least one of $R^7$ and $R^8$, $R^{21}$ and $R^{22}$, and $R^{24}$ and $R^{25}$, taken together, is morpholinyl, piperidinyl, or pyrrolidinyl;
(l) $R^9$, $R^{23}$, $R^{26}$, and $R^{27}$ are each independently $C_{1-5}$ alkyl;
(m) G is $C_{3-4}$ alkanediyl, optionally substituted with hydroxy, (L)-$C_{1-5}$ alkyloxy-, or [(L)-$C_{1-5}$ alkylene]amino-;
(n) G is $C_3$ alkanediyl, optionally substituted with hydroxy, (L)-$C_{1-5}$ alkyloxy-, or [(L)-$C_{1-5}$ alkylene]amino-;
(o) X is nitrogen;
(p) Y is $CR^{13}$;
(q) Z is $CR^{14}$;
(r) X is CH;
(s) $R^{12}$ is hydrogen, $R^{23}O(C=O)NH$—, $R^{22}NH(C=O)NH$—, $R^{23}SO_2NH$, $R^{23}SO$, or $R^{23}SO_2$, and $R^{13}$ is hydrogen, $R^{44}O(C=O)NH$—, $R^{43}NH(C=O)NH$—, $R^{44}SO_2NH$, $R^{44}SO$, or $R^{44}SO_2$;
(t) $R^{14}$ is hydrogen, halogen, $C_{1-5}$ alkoxy, $C_{1-5}$ alkyl, cyano, nitro, $R^{26}O(C=O)NH$—, $R^{25}NH(C=O)NH$—, $R^{26}SO_2NH$, or $R^{24}R^{25}N$.
(u) $R^{14}$ is halogen, $R^{26}O(C=O)NH$—, $R^{25}NH(C=O)NH$—, $R^{26}SO_2NH$, or $R^{24}R^{25}N$; Ar represents a monocyclic ring, optionally substituted with between 1 and 2 substituents selected independently from halogen, $C_{1-5}$ alkyl, cyano, nitro, $R^{15}R^{16}N$, $CF_3$, and $OCF_3$;
(v) Ar is a six membered ring substituted with between 1 and 2 substituents selected from halo, $CF_3$, and $OCF_3$, said substitutent or substitutents being at the 4-position or at the 3- and 4-positions, respectively;
(w) W is $SO_2$, C=O, or $CHR^{20}$;
(x) W is a covalent bond;
(y) W and $R^1$ taken together are formula (I)(a);
(z) W and $R^1$ taken together are formula (I)(b);
(aa) one of $R^3$ and $R^4$ is hydrogen; Ar represents a monocyclic ring, optionally substituted with between 1 and 2 substituents selected from halogen, $C_{1-5}$ alkyl, cyano, nitro, $R^{15}R^{16}N$, $CF_3$, and $OCF_3$; $R^{12}$ is hydrogen, $R^{23}SO$, or $R^{23}SO_2$; $R^{13}$ is hydrogen, $R^{44}SO$, or $R^{44}SO_2$; $R^{14}$ is hydrogen, halogen, $C_{1-5}$ alkoxy, $C_{1-5}$ alkyl, cyano, nitro, or $R^{24}R^{25}N$; and G is $C_{3-4}$ alkanediyl, optionally substituted with hydroxy, $C_{1-3}$ alkyl, (L)-$C_{1-5}$ alkyloxy, or [(L)-$C_{1-5}$ alkylene]amino-;

(bb) each of $R^3$ and $R^4$ is hydrogen; Ar represents a six membered ring, optionally substituted with between 1 and 2 substituents selected from halogen, $C_{1-5}$ alkyl, cyano, nitro, $R^{15}R^{16}N$, $CF_3$, and $OCF_3$; $R^{12}$ is hydrogen, $R^{23}SO$, or $R^{23}SO_2$; $R^{13}$ is hydrogen, $R^{44}SO$, or $R^{44}SO_2$; $R^{14}$ is hydrogen, halogen, $C_{1-5}$ alkoxy, $C_{1-5}$ alkyl, cyano, nitro, or $R^{24}R^{25}N$; and G is $C_3$ alkanediyl, optionally substituted with hydroxy, (L)-$C_{1-5}$ alkyloxy-, or (L)-$C_{1-5}$ alkylamino;

(cc) Ar is phenyl; and (dd) combinations of the above.

Specific preferred compounds include the examples herein, such as: 1-[4-(2-Amino-6-chloro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol; 1-[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-3-methyl-urea; 1-[3-Chloro-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-3-methyl-urea; 3-Amino-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-benzoic acid methyl ester; 3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenylamine; 1-[2-(4-{3-[3-(4-Bromo-phenyl)-5-methanesulfonyl-4,5,6,7-tetrahydro-pyrazolo[4,3-c]pyridin-1-yl]-2-hydroxy-propyl}-piperazin-1-yl)-3-chloro-phenyl]-3-methyl-urea; 1-{3-[4-(2-Chloro-6-methanesulfonylamino-phenyl)-piperazin-1-yl]-propyl}-3-(4-trifluoromethyl-phenyl)-1,4,6,7-tetrahydro-pyrazolo[4,3-c]pyridine-5-carboxylic acid amide; [3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-carbamic acid methyl ester; 1-[3-(4-Benzo[d]isothiazol-3-yl-piperazin-1-yl)-propyl]-3-(4-bromo-phenyl)-1,4,6,7-tetrahydro-pyrazolo[4,3-c]pyridine-5-carboxylic acid amide; 2-(4-{3-[5-Acetyl-3-(4-trifluoromethyl-phenyl)-4,5,6,7-tetrahydro-pyrazolo[4,3-c]pyridin-1-yl]-2-hydroxy-propyl}-piperazin-1-yl)-3-nitro-benzoic acid methyl ester; 1-[4-(2-Chloro-6-nitro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol; 2-(4-{2-Hydroxy-3-[3-(4-iodo-phenyl)-5-methanesulfonyl-4,5,6,7-tetrahydro-pyrazolo[4,3-c]pyridin-1-yl]-propyl}-piperazin-1-yl)-benzonitrile; 3-(4-Bromo-phenyl)-1-{3-[4-(2-nitro-phenyl)-piperazin-1-yl]-propyl}-1,4,6,7-tetrahydro-pyrazolo[4,3-c]pyridine-5-carboxylic acid amide; 2-(4-{3-[5-Acetyl-3-(4-iodo-phenyl)-4,5,6,7-tetrahydro-pyrazolo[4,3-c]pyridin-1-yl]-2-hydroxy-propyl}-piperazin-1-yl)-benzonitrile; 2-(4-{3-[3-(4-Chloro-3-methyl-phenyl)-5-methanesulfonyl-4,5,6,7-tetrahydro-pyrazolo[4,3-c]pyridin-1-yl]-2-hydroxy-propyl}-piperazin-1-yl)-benzonitrile; 1-(3-(4-Chloro-3-methyl-phenyl)-1-{3-[4-(2,4-dimethyl-phenyl)-piperazin-1-yl]-2-hydroxy-propyl}-1,4,6,7-tetrahydro-pyrazolo[4,3-c]pyridin-5-yl)-ethanone; 1-{3-[4-(3,5-Dichloro-pyridin-4-yl)-piperazin-1-yl]-propyl}-5-methanesulfonyl-3-(4-trifluoromethyl-phenyl)-4,5,6,7-tetrahydro-1H-pyrazolo[4,3-c]pyridine; 2-(4-{3-[5-Methanesulfonyl-3-(4-trifluoromethyl-phenyl)-4,5,6,7-tetrahydro-pyrazolo[4,3-c]pyridin-1-yl]-propyl}-piperazin-1-yl)-benzonitrile; N-[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-methanesulfonamide; 3-(3,4-Dichloro-phenyl)-1-{3-[4-(2-nitro-phenyl)-piperazin-1-yl]-propyl}-1,4,6,7-tetrahydro-pyrazolo[4,3-c]pyridine-5-carboxylic acid amide; and 3-(4-Chloro-3-methyl-phenyl)-1-{3-[4-(2-cyano-phenyl)-piperazin-1-yl]-2-hydroxy-propyl}-1,4,6,7-tetrahydro-pyrazolo[4,3-c]pyridine-5-carboxylic acid amide.

Furthermore, preferred compounds include those wherein Ar is selected from 4-trifluoromethylphenyl, 4-bromophenyl, 4-chlorophenyl, 4-chloro-3-methylphenyl and 3,4-dichlorophenyl.

More preferred compounds include the compounds in Examples 19, 27, and 33.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{18}F$ for use as a probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, *Protective Groups in Organic Synthesis,* 3rd ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl) ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyidiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(/midazol-1-ylmethyl)bis(4', 4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonate protecting groups include methyl, 9-fluorenylmethyl, ethyl, 2,2,2-trichloroethyl, 2-(trimethylsilyl)ethyl, 2-(phenylsulfonyl)ethyl, 2-(triphenylphosphonio) ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N', N'-tetramethylphosphorodiamidate, N-phenylcarbamate, borate, dimethylphosphinothioyl, and 2,4-dinitrophenylsulfenate.

Sulfonates

Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl) methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-di nitro-4-pyridonyl.

Special—NH Protective Groups

Examples of special NH protective groups include N-Alkyl and N-Aryl Amines N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N—(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or —S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl)imidazoles, N,N'-dimethylimidazolidines, 2,3-dihydro-1,3-benzothiazoles, diethylamine adducts, and methylaluminum bis(2,6-di-t-butyl-4-methylphenoxide)(MAD)complex.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl hydrazides.

C. SYNTHESIS
The compounds of the present invention may be prepared by conventional synthetic organic chemistry and by matrix or combinatorial methods according to Schemes 1 to 11 below, and representative detailed Examples 1 to 24. Those of ordinary skill in the art will be able to modify and adapt the guidance provided herein to make the disclosed compounds.
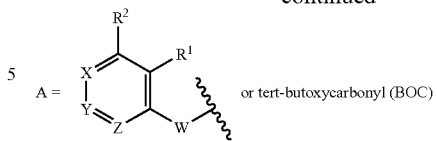
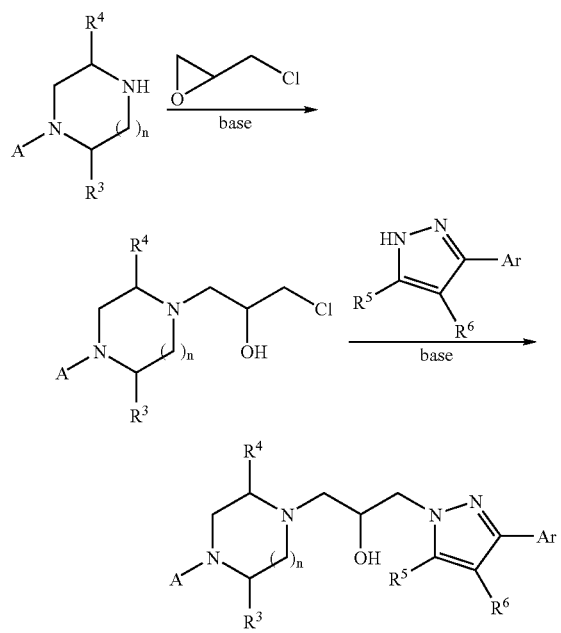
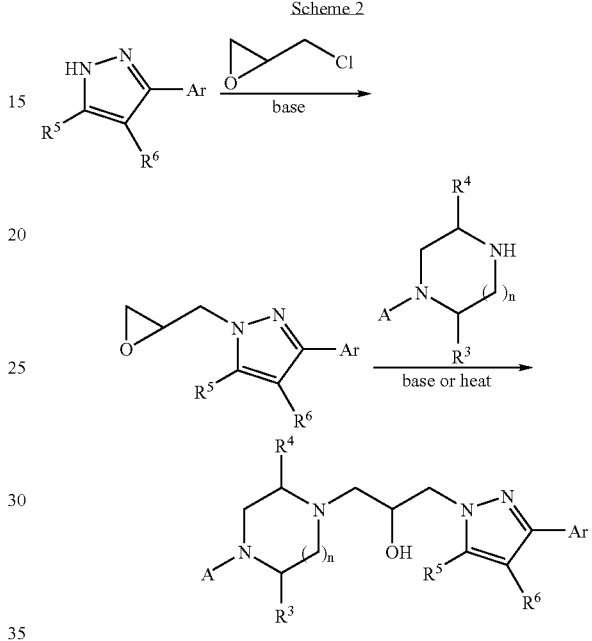
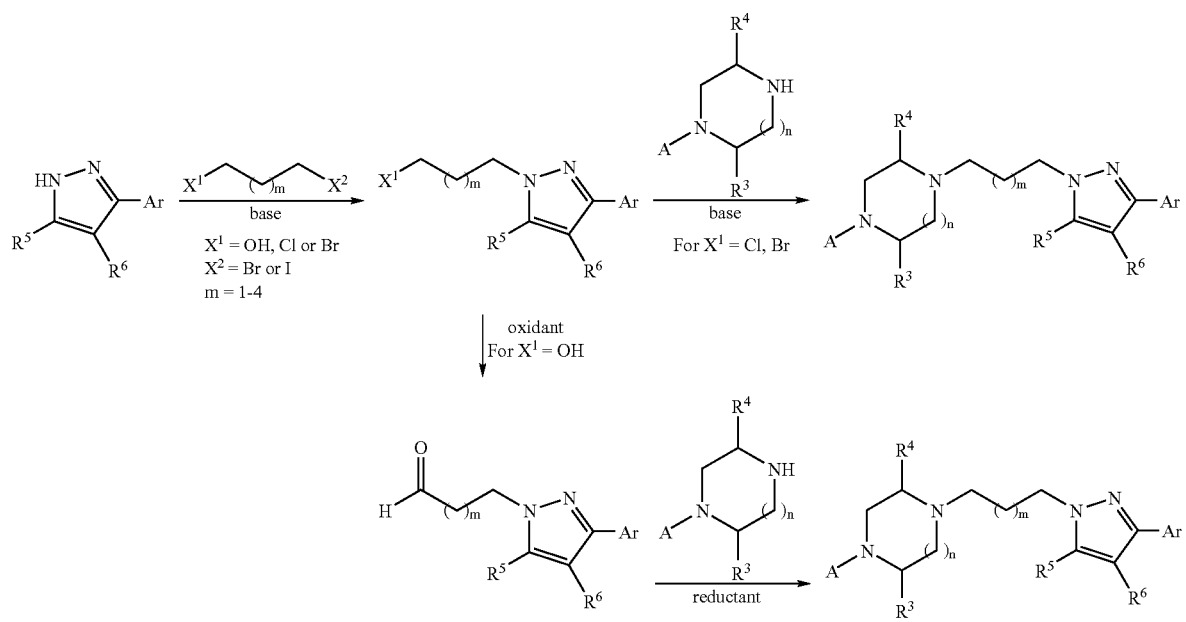

Scheme 4
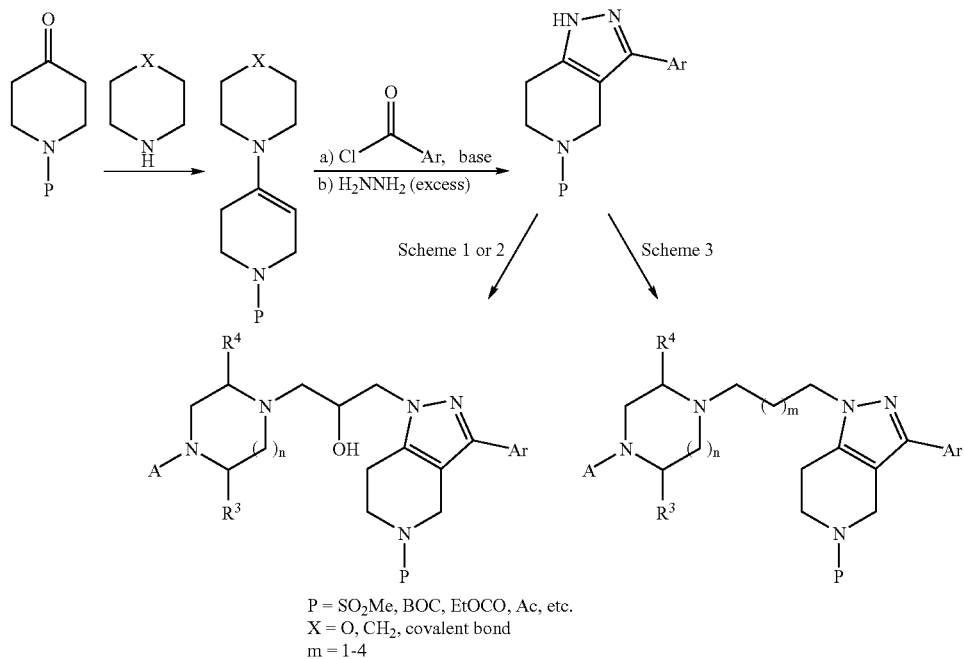
P = SO$_2$Me, BOC, EtOCO, Ac, etc.
X = O, CH$_2$, covalent bond
m = 1-4
Scheme 5
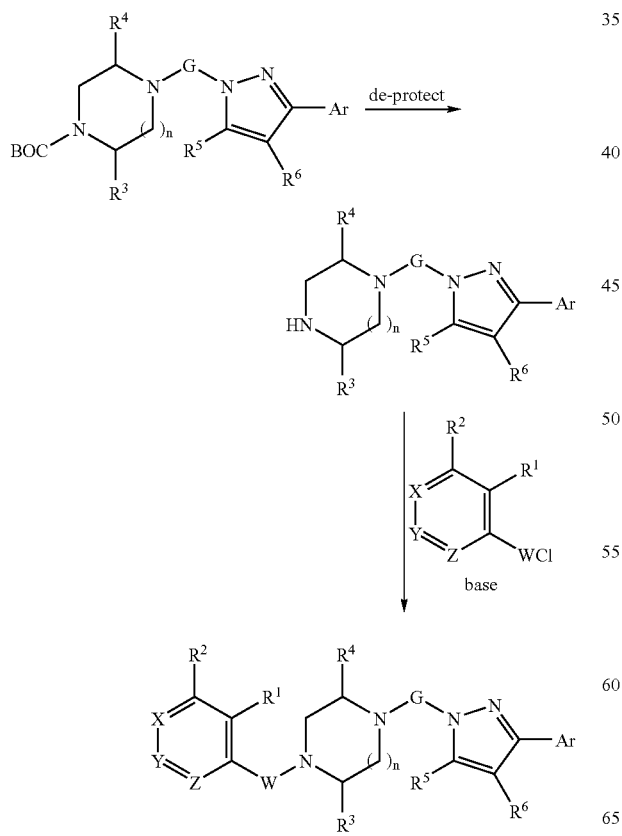

Scheme 6
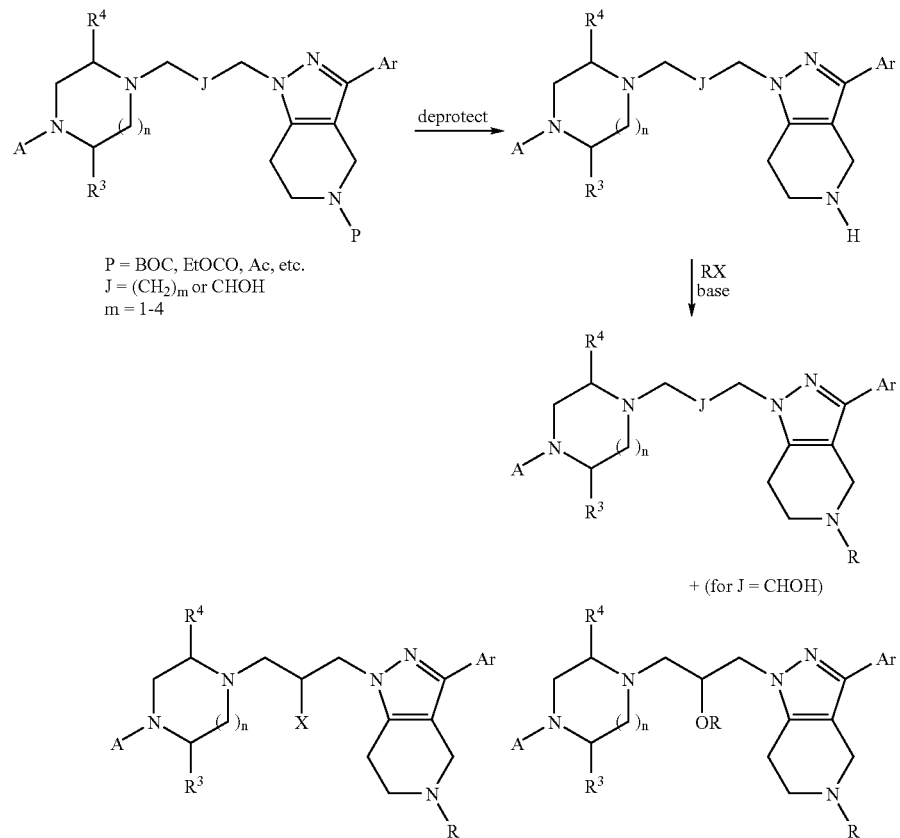
P = BOC, EtOCO, Ac, etc.
J = (CH$_2$)$_m$ or CHOH
m = 1-4
+ (for J = CHOH)
40
Scheme 7
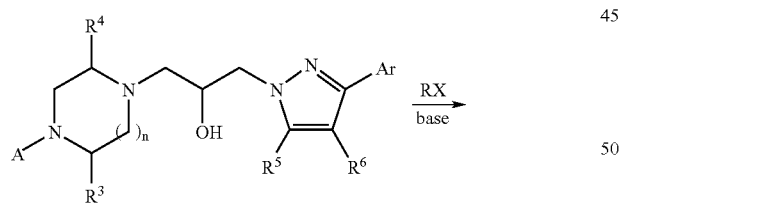
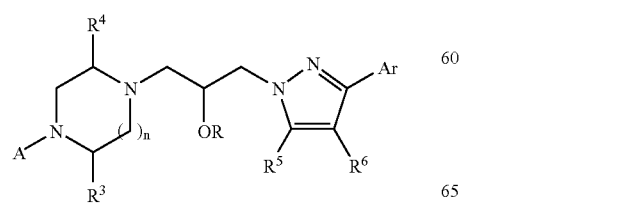

Scheme 8
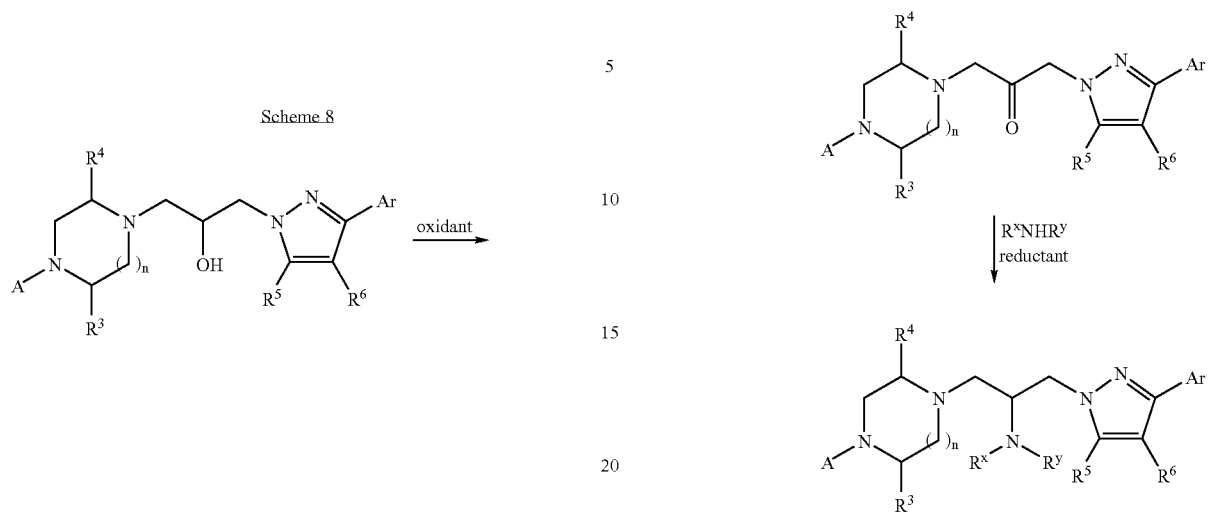
Scheme 9
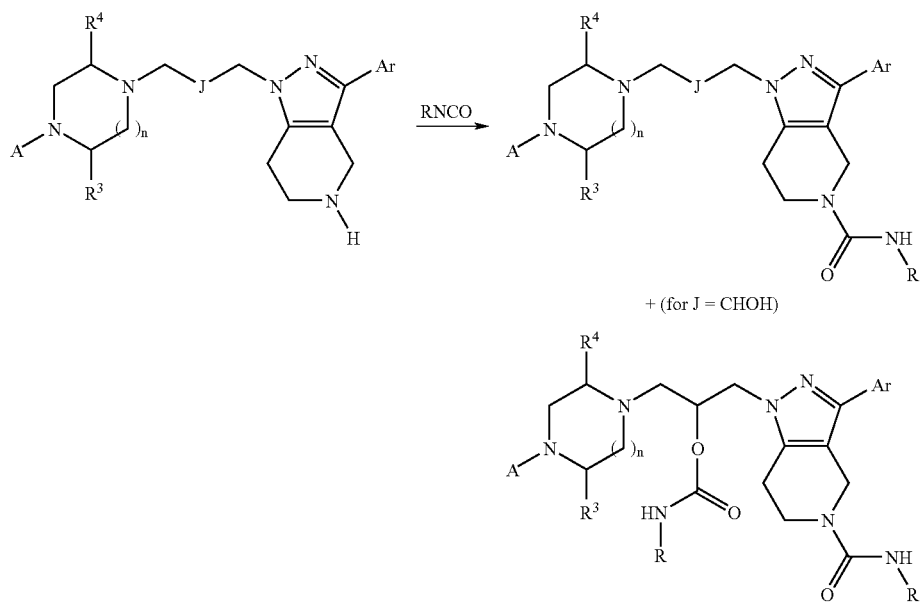
Scheme 10
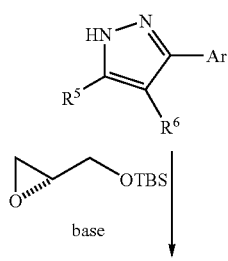
base

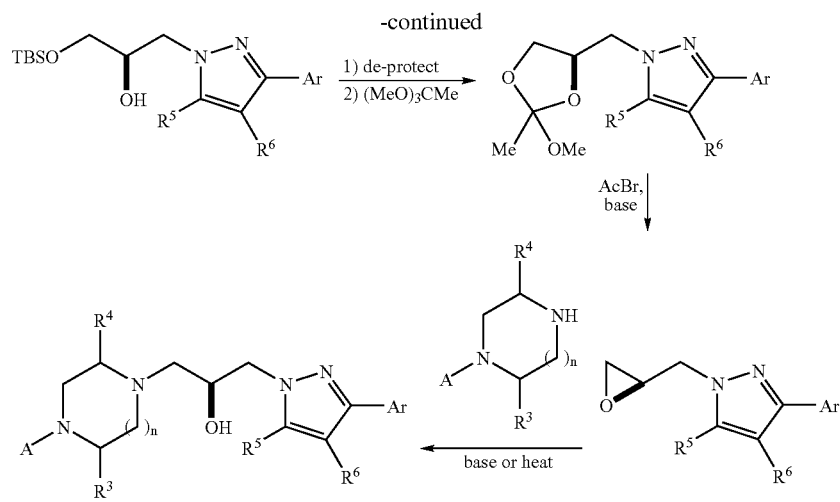

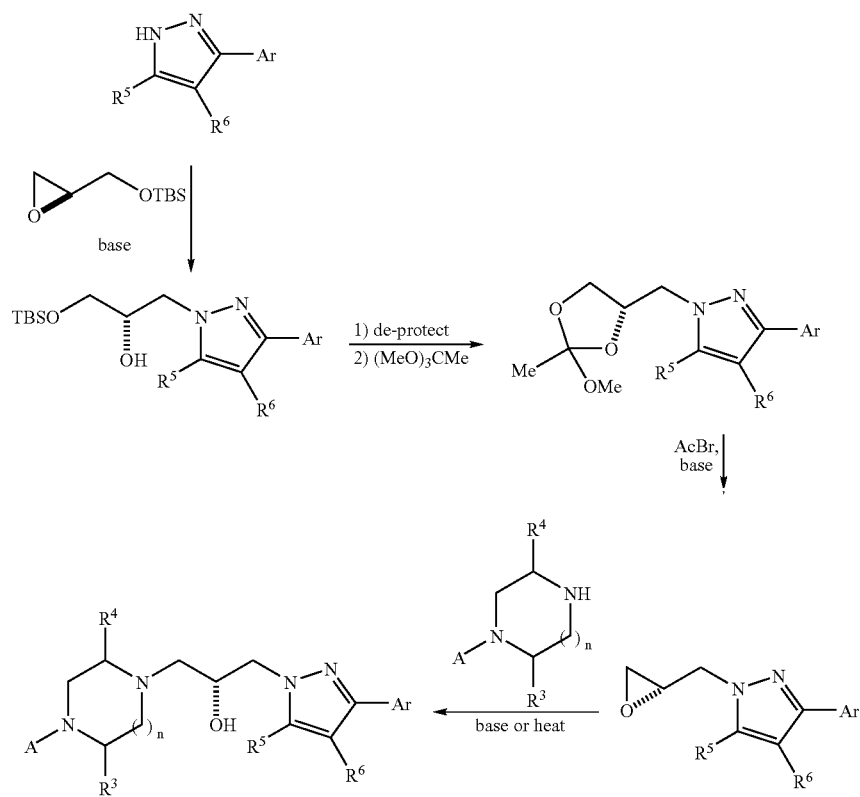

Scheme 11

D. FORMULATION AND ADMINISTRATION

The present compounds inhibit the proteolytic activity of human cathepsin S and therefore are useful as a medicine especially in methods for treating patients suffering from disorders or conditions which are modulated or regulated by the inhibition of cathepsin S activity.

The invention features a method for treating a subject with a condition mediated by cathepsin S, said method comprising administering to the subject a therapeutically effective amount of a pharmaceutical composition comprising a compound of the invention. The invention also provides a method for inhibiting cathepsin S activity in a subject, wherein the method comprises administering to the subject a therapeutically effective amount of a pharmaceutical composition comprising a compound of the invention. A third method is a method for treating an autoimmune disease, or inhibiting the progression of an autoimmune disease, in a subject, said method comprising administering to the subject a therapeutically effective amount of a pharmaceutical composition comprising a disclosed compound. The autoimmune disease can be, for example, lupus, rheumatoid arthritis, or preferably, asthma. The invention also provides a method for treating or inhibiting the progression of tissue transplant rejection in a subject, the method comprising administering to the subject a therapeutically effective amount of a pharmaceutical composition comprising a compound of the invention. The administration step can occur before, during, and/or after a tissue transplant procedure.

In view of their inhibitory effect on the proteolytic activity of human cathepsin S the compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier. A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula (I), due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salt forms which the disclosed compounds are able to form. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates which the disclosed componds, as well as the salts thereof, are able to form. Such solvates are for example hydrates, alcoholates and the like. Conversely the salt form can be converted by treatment with alkali into the free base form.

Stereoisomeric form defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

Those of skill in the treatment of disorders or conditions mediated by the cathepsin S enzyme could easily determine the effective daily amount from the test results presented hereinafter and other information. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the preparation, characterization, and use of the disclosed compounds.

E. EXAMPLES

Example 1

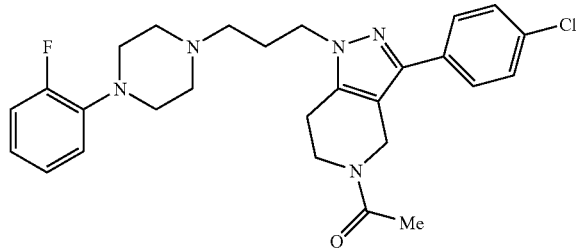

1-(3-(4-Chloro-phenyl)-1-{3-[4-(2-fluoro-phenyl)-piperazin-1-yl]-propyl}-1,4,6,7-tetrahydro-pyrazolo[4,3-c]pyridin-5-yl)-ethanone

A. 1-[3-(4-Chloro-phenyl)-1,4,6,7-tetrahydro-pyrazolo[4,3-c]pyridin-5-yl]-ethanone To a stirred solution of 50 g (0.35 mol) of N-acetyl-4-piperidone and 31 g (0.35 mol) of morpholine in benzene (350 mL) was added a catalytic amount (~0.25 g) of p-toluenesulfonic acid. The mixture was heated to reflux for 10 h with a Dean-Stark trap. The solvent was removed under reduced pressure to give a brown oil. The crude product was diluted with $CH_2Cl_2$ (175 mL) and 50.0 mL (0.35 mol) of $Et_3N$ was added. The mixture was cooled to 0° C. and a solution of 45.0 mL (0.35 mol) of 4-chlorobenzoyl chloride in $CH_2Cl_2$ (50 mL) was added slowly by dropping funnel over 1 h. The mixture was allowed to warm to room temperature and stirred overnight. The reaction was then diluted with 1 N HCl (150 mL) and stirred vigorously for 3 h. The aqueous layer was extracted with $CH_2Cl_2$ (3×250 mL) and the combined extracts were dried over $Na_2SO_4$ and the solvent was removed under reduced pressure. The crude oil was diluted with EtOH (350 mL) and cooled to 0° C. To this stirred solution was slowly added 33.0 mL (1.06 mol) of hydrazine and the mixture was allowed to warm to room temperature and stir overnight during which time a white precipitate formed. The volume of the reaction was reduced to ~150 mL and EtOAc (750 mL) was added to the mixture. The suspension was stirred vigorously for 2 h and was filtered then washed with EtOAc (2×200 mL) and dried under vacuum to afford 41.4 g (42% over 3 steps) of a pale yellow solid. TLC (silica, 5% MeOH/$CH_2Cl_2$): $R_f$=0.3. MS (electrospray), m/z calculated for $C_{14}H_{14}ClN_3O$ $[M+H]^+$ 276.08, observed 276.0. $^1H$ NMR (400 MHz, $CDCl_3$, a mixture of amide rotamers): 7.65 (d, J=8.4 Hz, 2H), 7.64 (d, J=9.3 Hz, 2H), 7.58 (d, J=10.5 Hz, 2H), 7.55 (d, J=8.5 Hz, 2H), 4.94 (s, 2H), 4.78 (s, 2H), 4.08 (t, J=5.9 Hz, 2H), 3.90 (t, J=5.8 Hz, 2H), 3.02 (t, J=5.8 Hz, 2H), 2.96 (t, J=5.9 Hz, 2H), 2.36 (s, 3H), 2.31 (s, 3H).

B. 1-[3-(4-Chloro-phenyl)-1-(3-chloro-propyl)-1,4,6,7-tetrahydro-pyrazolo[4,3-c]pyridin-5-yl]-ethanone $Cs_2CO_3$ (2.66 g, 8.2 mmol) was added to a solution of 1-[3-(4-chloro-phenyl)-1,4,6,7-tetrahydro-pyrazolo[4,3-c]pyridin-5-yl]-ethanone (1.0 g, 5.4 mmol) in DMF (10 mL) and stirred for 15 min. 1-Bromo-3-chloropropane (1.28 g, 8.2 mmol) was added and stirred under $N_2$ at room temperature for 36 h. Water (50 mL) was added to the reaction and stirred for 5 min. The product precipitated out. The aqueous portion was decanted and water was added to the residue and decanted again. The semisolid was taken up in $CH_2Cl_2$ and passed through a short plug of $SiO_2$ (5% MeOH/EtOAc) to obtain 1.06 g (83%) of a pale yellow semisolid. MS (electrospray): exact mass calculated for $C_{17}H_{19}Cl_2N_3O$, 351.09; m/z found, 352.0 $[M+H]^+$. $^1H$ NMR (500 MHz, $CDCl_3$, a mixture of 1:1 rotamers): 7.60 (d, J=8.3 Hz, 1H), 7.53 (d, J=8.3 Hz, 1H), 7.40 (d, J=8.3 Hz, 1H), 7.36 (d, J=8.3 Hz, 1H), 4.77 (s, 1H), 4.61 (s, 1H), 4.20 (t, J=6.2 Hz, 2H), 3.94 (t, J=5.8 Hz, 1H), 3.76 (t, J=5.8 Hz, 1H), 3.52 (q, J=6.1 Hz, 2H), 2.84 (t, J=5.5 Hz, 1H), 2.77 (t, J=5.6 Hz, 1H), 2.37 (sextet, J=6.1 Hz, 2H), 2.21 (s, 1.5H), 2.16 (s, 1.5H).

C. 1-(3-(4-Chloro-phenyl)-1-{3-[4-(2-fluoro-phenyl)-piperazin-1-yl]-propyl}-1,4,6,7-tetrahydro-pyrazolo[4,3-c]pyridin-5-yl)-ethanone 1-[3-(4-Chloro-phenyl)-1-(3-chloro-propyl)-1,4,6,7-tetrahydro-pyrazolo[4,3-c]pyridin-5-yl]-ethanone (0.053 g, 0.15 mmol) was dissolved in $CH_3CN$ (0.5 mL) and a solution of 1-(2-fluorophenyl)piperazine (0.053 g, 0.30 mmol) in $CH_3CN$ (0.5 mL) was added, followed by $K_2CO_3$ (0.031 g, 0.22 mmol) and $Bu_4NI$ (0.018 g, 0.05 mmol). The mixture was stirred at room temperature for 7 d. Preparative TLC (silica, 5% MeOH/EtOAc) afforded 30 mg (41%) of the title compound. MS (electrospray): exact mass calculated for $C_{27}H_{31}ClFN_5O$, 495.22; m/z found, 496.3 $[M+H]^+$. $^1H$ NMR (500 MHz, $CDCl_3$, a mixture of 1:1 rotamers): 7.60 (d, J=8.3 Hz, 1H), 7.54 (d, J=8.3 Hz, 1H), 7.39 (d, J=8.3 Hz, 1H), 7.35 (d, J=8.3 Hz, 1H), 7.06-6.90 (m, 4H), 4.77 (s, 1H), 4.60 (s, 1H), 4.10 (t, J=6.8 Hz, 2H), 3.92 (t, J=5.7 Hz, 1H), 3.74 (t, J=5.7 Hz, 1H), 3.08 (br s, 4H), 2.83 (t, J=5.6 Hz, 1H), 2.77 (t, J=5.7 Hz, 1H), 2.58 (br s, 4H), 2.41-2.38 (m, 2H), 2.19 (s, 1.5H), 2.13 (s, 1.5H), 2.10-2.07 (m, 2H).

Example 2

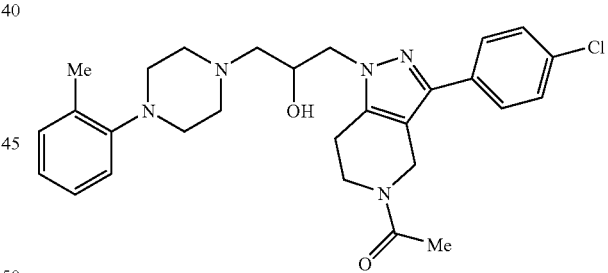

1-{3-(4-Chloro-phenyl)-1-[2-hydroxy-3-(4-o-tolyl-piperazin-1-yl)-propyl]-1,4,6,7-tetrahydro-pyrazolo[4,3-c]pyridin-5-yl}-ethanone

A. 1-[3-(4-Chloro-phenyl)-1-oxiranylmethyl-1,4,6,7-tetrahydro-pyrazolo[4,3-c]pyridin-5-yl]-ethanone To a stirred solution of 1.00 g (3.63 mmol) of 1-[3-(4-chloro-phenyl)-1,4,6,7-tetrahydro-pyrazolo[4,3-c]pyridin-5-yl]-ethanone and 2.85 mL (36.3 mmol) of epichlorohydrin was added 1.30 g (3.99 mmol) of solid $Cs_2CO_3$. The reaction was stirred for 48 h and the solvent was removed under reduced pressure. The residue was then diluted with $H_2O$ (50 mL) and EtOAc (50 mL). The layers were separated, and the organic layer was washed with $H_2O$ (25 mL) and brine (25 mL), dried over Na$_2$SO$_4$ and the solvent was removed under reduced pressure. Purification by flash chromatography (silica, 0-15% acetone/CH$_2$Cl$_2$) afforded 0.72 g (60%) of a white solid. TLC (silica, 5% MeOH/CH$_2$Cl$_2$): R$_f$=0.5. MS (electrospray): m/z calculated for C$_{17}$H$_{18}$ClN$_3$O$_2$ [M+H]$^+$, 332.11, observed 332.0. $^1$H NMR (400 MHz, CDCl$_3$, a mixture of amide rotamers): 7.60 (d, J=8.6 Hz, 2H), 7.54 (d, J=8.4 Hz, 2H), 7.40 (d, J=8.6 Hz, 2H), 7.36 (d, J=8.4 Hz, 2H), 4.80 and 4.73 (A and B of AB quartet, J$_{ab}$=15.8 Hz, 2H), 4.60 (s, 2H), 4.47 (dd, J=15.3, 2.5 Hz, 1H), 4.42 (dd, J=15.0, 2.7 Hz, 1H), 4.11 (dd, J=5.3, 2.5 Hz, 1H), 4.08 (dd, J=5.1, 3.3 Hz, 1H), 3.99-3.85 (m, 2H), 3.73 (dt, J=5.9, 1.8 Hz, 2H), 3.37 (m, 2H), 2.87-2.80 (m, 3H), 2.80-2.69 (m, 3H), 2.53 (dd, J=4.7, 2.5 Hz, 1H), 2.48 (dd, J=4.6, 2.6, 1H), 2.19 (s, 3H), 2.15 (s, 3H).

B. 1-{3-(4-Chloro-phenyl)-1-[2-hydroxy-3-(4-o-tolyl-piperazin-1-yl)-propyl]-1,4,6,7-tetrahydro-pyrazolo[4,3-c]pyridin-5-yl}-ethanone A solution of of 1-[3-(4-chloro-phenyl)-1-oxiranylmethyl-1,4,6,7-tetrahydro-pyrazolo[4,3-c]pyridin-5-yl]-ethanone (0.8 g, 2.42 mmol) in CH$_2$Cl$_2$ (12 mL) was treated with ytterbium(III) triflate (0.15 g, 0.24 mmol) and 1-(O-tolyl)-piperazine (0.51 g, 2.90 mmol) at 25° C. The reaction mixture was stirred for 24 h and diluted with EtOAc (100 mL) and H$_2$O (50 mL). The organic layer was separated, washed with H$_2$O (2×50 mL), dried over Na$_2$SO$_4$, and concentrated. Column chromatography (silica, 5% MeOH/CH$_2$Cl$_2$) afforded 1.08 g (88%) of the target compound, a white powder. TLC (silica, 10% MeOH/CH$_2$Cl$_2$): R$_f$=0.38. MS (electrospray): m/z 508.3 ([M+H]$^+$, C$_{28}$H$_{34}$ClN$_5$O$_2$ requires 507.2). $^1$H NMR (CDCl$_3$, 400 MHz, a mixture of two rotamers): 7.60 and 7.37 (AB pattern, J$_{ab}$=8.8 Hz, 2H), 7.54 and 7.40 (AB pattern, J$_{ab}$=8.8 Hz, 2H), 7.18-7.14 (m, 2H), 7.00-6.97 (m, 2H), 4.85 and 4.73 (AB pattern, J$_{ab}$=15.5 Hz, 1H), 4.62 (s, 1H), 4.20-4.11 (m, 2H), 4.06-4.01 (m, 1H), 3.88-3.70 (m, 2H), 2.97-2.87 (m, 6H), 2.85-2.75 (m, 2H), 2.65-2.55 (m, 2H), 2.51-2.48 (m, 2H), 2.29 (s, 3H), 2.21 (s, 1.5H), 2.17 (s, 1.5H).

Example 3

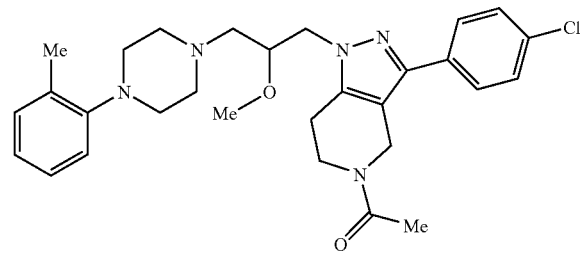

1-{3-(4-Chloro-phenyl)-1-[2-methoxy-3-(4-o-tolyl-piperazin-1-yl)-propyl]-1,4,6,7-tetrahydro-pyrazolo[4,3-c]pyridin-5-yl}-ethanone A stirred solution of 1-{3-(4-chloro-phenyl)-1-[2-hydroxy-3-(4-o-tolyl-piperazin-1-yl)-propyl]-1,4,6,7-tetrahydro-pyrazolo[4,3-c]pyridin-5-yl}-ethanone (25 mg, 0.05 mmol) in THF (0.2 mL) was treated with NaH (1.42 mg, 0.06 mmol) at 25° C. After 20 min, methyl iodide (3.7 μL, 0.06 mmol) was added and the reaction mixture was stirred for an additional 2 h. Preparative TLC (silica, 5% MeOH/CH$_2$Cl$_2$) afforded 14.6 mg (56%) of a colorless film. TLC (silica, 10% MeOH/CH$_2$Cl$_2$): R$_f$=0.38. MS (electrospray): m/z 522.2 ([M+H]$^+$, C$_{29}$H$_{36}$ClN$_5$O$_2$ requires 521.3). $^1$H NMR (CDCl$_3$, 400 MHz, a mixture of two rotamers): 7.62 and 7.37 (AB pattern, J$_{ab}$=8.8 Hz, 2H), 7.55 and 7.40 (AB pattern, J$_{ab}$=8.8 Hz, 2H), 7.18-7.14 (m, 2H), 7.02-6.95 (m, 2H), 4.82 and 4.75 (AB pattern, J$_{ab}$=15.5 Hz, 1H), 4.62 (s, 1H), 4.30-4.25 (m, 1H), 4.09-3.73 (m, 4H), 3.29 (s, 1.5H), 3.27 (s, 1.5H), 2.93-2.55 (m, 12H), 2.30 (s, 3H), 2.21 (s, 1.5H), 2.16 (s, 1.5H).

Example 4

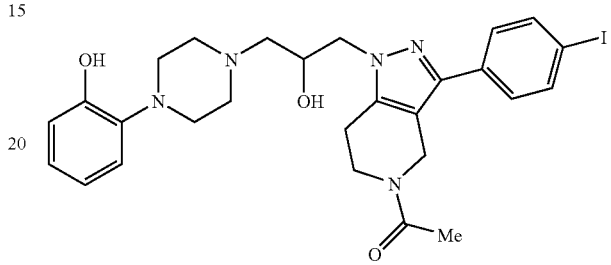

1-[1-{2-Hydroxy-3-[4-(2-hydroxy-phenyl)-piperazin-1-yl]-propyl}-3-(4-iodo-phenyl)-1,4,6,7-tetrahydro-pyrazolo[4,3-c]pyridin-5-yl]-ethanone A. 1-[3-(4-Iodo-phenyl)-1,4,6,7-tetrahydro-pyrazolo[4,3-c]pyridin-5-yl]-ethanone A flask equipped with a Dean-Stark trap was charged with N-acetyl-4-piperidone (27.29 g, 137 mmol), piperidine (16.5 mL, 129 mmol), p-toluene-sulfonic acid (0.5 g) and benzene (150 mL). The mixture was heated to 125° C. After 8 h the mixture was allowed to cool, and concentrated in vacuo to give the corresponding enamine (35 g). A solution of p-iodobenzoyl chloride (9.28 g, 34.8 mmol) in CH$_2$Cl$_2$ (40 mL) was added dropwise to a 0° C. solution of the enamine (11.0 g, ca. 41 mmol) in CH$_2$Cl$_2$ (80 mL) over 2 h. The mixture was then allowed to warm to room temperature and stirred for an additional 17 h. The solution was treated with 1 N HCl (200 mL) and stirred vigorously for 5 h. The layers were separated and the aqueous layer was extracted with CH$_2$Cl$_2$ (3×150 mL). The combined extracts were dried over Na$_2$SO$_4$ and concentrated. The residue was dissolved in EtOH (200 mL) and treated with NH$_2$NH$_2$ (16.0 mL, 51 mmol). The mixture was stirred for 17 h and H$_2$O (300 mL) was added. The precipitate formed was collected by filtration and air dried to give 8.82 g (59%) of 1-[3-(4-iodo-phenyl)-1,4,6,7-tetrahydro-pyrazolo[4,3-c]pyridin-5-yl]-ethanone which was suitable for use without further purification. TLC (silica, 5% MeOH/CH$_2$Cl$_2$): R$_f$=0.3. MS (electrospray): m/z calculated for C$_{14}$H$_{15}$IN$_3$O [M+H]$^+$368.03, found 368.0. $^1$H NMR (CD$_3$OD/CDCl$_3$, 500 MHz, a mixture of amide rotamers): 7.72 (d, J=8.2 Hz, 2H), 7.69 (d, J=8.3 Hz, 2H), 7.24 (d, J=8.2 Hz, 2H), 7.20 (d, J=8.3 Hz, 2H), 4.69 (s, 2H), 4.56 (s, 2H), 3.83 (t, J=6.0 Hz, 2H), 3.69 (t, J=5.8 Hz, 2H), 2.79, (t, J=5.7 Hz, 2H), 2.72, (t, J=5.8 Hz, 2H), 2.13 (s, 3H), 2.08 (s, 3H).

B. 1-[3-(4-Iodo-phenyl)-1-oxiranylmethyl-1,4,6,7-tetrahydro-pyrazolo[4,3-c]pyridin-5-yl]-ethanone Cs$_2$CO$_3$ (1.30 g, 4.01 mmol) was added to a solution of 1-[3-(4-iodo-phenyl)-1,4,6,7-tetrahydro-pyrazolo[4,3-c]pyridin-5-yl]-ethanone (1.34 g, 3.65 mmol) and epichlorohydrin (2.85 mL, 36.4 mmol) in DMF (10.0 mL). The mixture was stirred for 17 h then partitioned between EtOAc (400 mL) and saturated NaHCO$_3$ (150 mL). The NaHCO$_3$ layer was extracted with EtOAc (2×150 mL). The combined extracts were washed with H$_2$O (2×150 mL), brine (150 mL), dried over Na$_2$SO$_4$ and concentrated. The residue was purified by column chromatography (silica, 10-25% acetone/CH$_2$Cl$_2$) to give 890 mg (58%) of the title compound. HPLC, $t_R$=5.53 min. (Reverse phase conditions: HP 1100 LCMS, Phenomenex luna 2.1×150 mm column, 60% MeOH/H$_2$O (0.5% AcOH) to 90% MeOH/H$_2$O (0.5% AcOH), held at initial conditions for 2 min then ramped to final conditions over 5 min.) MS (electrospray), m/z calculated for C$_{17}$H$_{18}$IN$_3$O$_2$Na [M+Na]$^+$445.04, found 445.95. $^1$H NMR (CDCl$_3$, 500 MHz, a mixture of amide rotamers): 7.76 (d, J=8.3 Hz, 2H), 7.75 (d, J=8.3 Hz, 2H), 7.42 (d, J=8.2 Hz, 2H), 7.35 (d, J=8.2 Hz, 2H), 4.80 and 4.73 (A and B of AB quartet, J$_{ab}$=15.6 Hz, 2H), 4.60 (s, 2H), 4.84 (dd, J=15.1, 2.1 Hz, 1H), 4.42 (dd, J=15.0, 2.1 Hz, 1H), 4.11 (t, J=5.0, Hz, 1H), 4.08 (t, J=5.0 Hz, 1H), 3.98-3.87 (m, 2H), 3.74 (m, 2H), 3.34 (m, 2H), 2.87-2.72 (m, 6H), 2.52 (dd, J=4.6, 2.6 Hz, 1H), 2.48 (dd, J=4.5, 2.6 Hz, 1H), 2.20 (s, 3H), 2.14 (s, 3H).

C. 1-[1-[2-Hydroxy-3-[4-(2-hydroxy-phenyl)-piperazin-1-yl]-propyl]-3-(4-iodo-phenyl)-1,4,6,7-tetrahydro-pyrazolo[4,3-c]pyridin-5-yl]-ethanone 1-[3-(4-Iodo-phenyl)-1-oxiranylmethyl-1,4,6,7-tetrahydro-pyrazolo[4,3-c]pyridin-5-yl]-ethanone (62 mg, 0.15 mmol) and 4-(2-hydroxyphenyl)-piperazine (34 mg, 0.19 mmol) were combined in CH$_2$Cl$_2$ (0.5 mL) and the solution treated with Yb(OTf)$_3$.H$_2$O (44 mg, 0.071 mmol). The mixture was shaken for 72 h then diluted with CH$_2$Cl$_2$ (1 mL). Purification by preparative TLC (silica, 10% MeOH/CH$_2$Cl$_2$) gave 45 mg (51%) of an off-white powder. TLC (silica, 8% MeOH/CH$_2$Cl$_2$): R$_f$=0.2. MS (electrospray): m/z calculated for C$_{27}$H$_{33}$IN$_5$O$_3$ [M+H]$^+$602.15, found 602.2. $^1$H NMR (CDCl$_3$, 500 MHz, a mixture of amide rotamers): 7.76 (d, J=8.6 Hz, 1H), 7.72 (d, J=8.6 Hz, 1H), 7.42 (d, J=8.5 Hz, 1H), 7.34 (d, J=8.5 Hz, 1H), 7.14 (m, 1H), 7.80 (t, J=7.7 Hz, 1H), 6.94 (d, J=8.1 Hz, 1H), 6.86 (t, J=7.7 Hz, 1H), 4.83 and 4.72 (A and B of AB quartet, J$_{ab}$=15.6 Hz, 1H), 4.61 (s, 1H), 4.22-4.15 (m, 2H), 4.02 (m, 2H), 3.88 (m, 1H), 3.76 (m, 3H), 3.00-2.49 (m, 11H), 2.20 (s, 1.5H), 2.15 (s, 1.5H).

Example 5

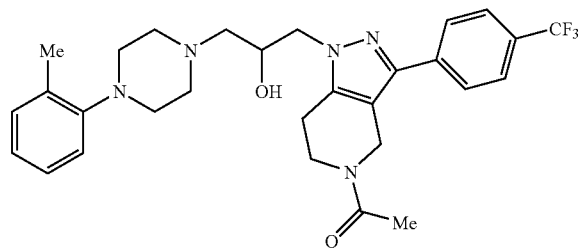

1-[1-[2-Hydroxy-3-(4-o-tolyl-piperazin-1-yl)-propyl]-3-(4-trifluoromethyl-phenyl)-1,4,6,7-tetrahydro-pyrazolo[4,3-c]pyridin-5-yl]-ethanone A. 1-[3-(4-Trifluoromethyl-phenyl)-1,4,6,7-tetrahydro-pyrazolo[4,3-c]pyridin-5-yl]-ethanone A solution of N-acetyl-4-piperidone (2.82 g, 20 mmol), morpholine (1.93 mL, 22 mmol) and p-toluenesulfonic acid (5 mg) in benzene (8.5 mL) was refluxed for 8 h in a Dean-Stark apparatus. The solvent was removed and the residue dissolved in CH$_2$Cl$_2$ (20 mL). Triethylamine (3.1 mL) was added and p-trifluoromethylbenzoyl chloride (3.27 mL, 22 mmol) in CH$_2$Cl$_2$ (4 mL) was added dropwise into the solution at 0° C. The reaction mixture was stirred at 25° C. for 24 h and diluted with aqueous HCl (5%, 25 mL). After stirring for another 30 min, the organic layer was separated, washed with H$_2$O (20 mL), dried (Na$_2$SO$_4$), and concentrated. The residue was dissolved in EtOH (95%, 18 mL) and treated at 0° C. with hydrazine (2.9 mL, 60 mmol). The mixture was stirred at 25° C. for 3 h and H$_2$O (4 mL) was added. Most of the volatiles were removed and the residue extracted with CH$_2$Cl$_2$ (50 mL). The organic layer was separated, washed with H$_2$O (20 mL), dried over Na$_2$SO$_4$, and concentrated. Column chromatography (silica, 5% MeOH/CH$_2$Cl$_2$) provided 5.1 g (83%) of a white powder. TLC (silica, 10% MeOH/CH$_2$Cl$_2$): R$_f$=0.30. MS (electrospray): m/z 332.0 ([M+Na]$^+$, C$_{15}$H$_{14}$F$_3$N$_3$O requires 309.1). $^1$H NMR (CDCl$_3$, 400 MHz, a mixture of two rotamers): 7.73-7.67 (m, 4H), 4.85 (s, 1.2H), 4.68 (s, 0.8H), 3.96 (t, J=4.5 Hz, 0.8H), 3.78 (t, J=4.5 Hz, 1.2H), 2.89 (t, J=4.5 Hz, 1.2H), 2.83 (t, J=4.5 Hz, 0.8H), 2.23 (s, 1.8H), 2.18 (s, 1.2H).

B. 1-[1-Oxiranylmethyl-3-(4-trifluoromethyl-phenyl)-1,4,6,7-tetrahydro-pyrazolo[4,3-c]pyridin-5-yl]-ethanone A solution of 1-[3-(4-trifluoromethyl-phenyl)-1,4,6,7-tetrahydro-pyrazolo[4,3-c]pyridin-5-yl]-ethanone (2.4 g, 7.77 mmol) in DMF (15 mL) was treated with cesium carbonate (5.05 g, 15.5 mmol) and epichlorohydrin (6.1 mL, 77.7 mmol) at 25° C. and stirred for 24 h before it was diluted with EtOAc (100 mL) and H$_2$O (50 mL). The organic layer was separated, washed with H$_2$O (2×50 mL), brine (50 mL), dried over Na$_2$SO$_4$, and concentrated. Column chromatography (silica, 10% acetone/CH$_2$Cl$_2$) provided 2.30 g (81%) of a white powder. TLC (silica, 10% MeOH/CH$_2$Cl$_2$): R$_f$=0.35. MS (electrospray): m/z 388.0 ([M+Na]$^+$, C$_{18}$H$_{18}$F$_3$N$_3$O$_2$ requires 365.1). $^1$H NMR (CDCl$_3$, 400 MHz, a mixture of two rotamers): 7.77 and 7.63 (AB pattern, J$_{ab}$=8.2 Hz, 2H), 7.71 and 7.67 (AB pattern, J$_{ab}$=8.4 Hz, 2H), 4.82 and 4.76 (AB pattern, J$_{ab}$=15.5 Hz, 1.2H), 4.58 (s, 0.8H), 4.45-4.35 (m, 1H), 4.08-4.02 (m, 1H), 3.92-3.80 (m, 1H), 3.70-3.63 (m, 1H), 3.30 (m, 1H), 2.80-2.67 (m, 3H), 2.48-2.42 (m, 1H), 2.13 (s, 1.3H), 2.08 (s, 1.7H).

C. 1-[1-[2-Hydroxy-3-(4-o-tolyl-piperazin-1-yl)-propyl]-3-(4-trifluoromethyl-phenyl)-1,4,6,7-tetrahydro-pyrazolo[4,3-c]pyridin-5-yl-ethanone A solution of 1-[1-oxiranylmethyl-3-(4-trifluoromethyl-phenyl)-1,4,6,7-tetrahydro-pyrazolo[4,3-c]pyridin-5-yl]-ethanone (1.16 g, 3.20 mmol) in CH$_2$Cl$_2$ (15 mL) was treated with ytterbium(III) triflate (0.40 g, 0.64 mmol) and 1-(O-tolyl)-piperazine (0.84 g, 4.77 mmol) at 25° C. and stirred for 48 h before it was diluted with CH$_2$Cl$_2$ (100 mL) and H$_2$O (50 mL). The organic layer was separated, washed with H$_2$O (2×50 mL), dried over Na$_2$SO$_4$, and concentrated. Column chromatography (silica, 5% MeOH/CH$_2$Cl$_2$) afforded 1.54 g (89%) of a white powder. TLC (silica, 10% MeOH/CH$_2$Cl$_2$): R$_f$=0.35. MS (electrospray): m/z 542.3 ([M+H]$^+$, C$_{29}$H$_{34}$F$_3$N$_5$O$_2$ requires 541.3). $^1$H NMR (CDCl$_3$, 400 MHz, a mixture of two rotamers): 7.82 and 7.65 (AB pattern, J$_{ab}$=8.2 Hz, 2H), 7.72 and 7.68 (AB pattern, J$_{ab}$=8.4 Hz, 2H), 7.18-6.97 (m, 4H), 4.88 and 4.76 (AB pattern, J$_{ab}$=16 Hz, 0.9H), 4.65 (s, 1.1H), 4.23-4.12 (m, 2H), 4.08-4.00 (m, 2H), 3.88-3.70 (m, 2H), 3.02-2.85 (m, 6H), 2.85-2.75 (m, 2H), 2.65-2.55 (m, 2H), 2.53-2.45 (m, 2H), 2.29 (s, 3H), 2.21 (s, 1.8H), 2.17 (s, 1.2H).

Example 6

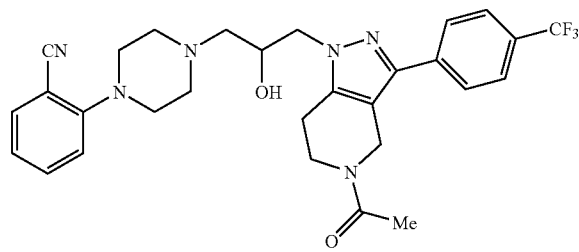

2-(4-{3-[5-Acetyl-3-(4-trifluoromethyl-phenyl)-4,5,6,7-tetrahydro-pyrazolo[4,3-c]pyridin-1-yl]-2-hydroxy-propyl}-piperazin-1-yl)-benzonitrile A solution of 1-[1-oxiranylmethyl-3-(4-trifluoromethyl-phenyl)-1,4,6,7-tetrahydro-pyrazolo[4,3-c]pyridin-5-yl]-ethanone (0.84 g, 2.30 mmol) in $CH_2Cl_2$ (10 mL) was treated with ytterbium(III) triflate (0.29 g, 0.46 mmol) and 1-(2-cyanophenyl)-piperazine (0.75 g, 3.5 mmol) at 25° C. and stirred for 48 h before it was diluted with $CH_2Cl_2$ (100 mL) and $H_2O$ (50 mL). The organic layer was separated, washed with $H_2O$ (2×50 mL), dried over $Na_2SO_4$, and concentrated. Column chromatography (silica, 5% $MeOH/CH_2Cl_2$) afforded 1.15 g (90%) of light yellow crystals. TLC (silica, 10% $MeOH/CH_2Cl_2$): $R_f$=0.30. MS (electrospray): m/z 553.3 ([M+H]$^+$, $C_{29}H_{31}F_3N_6O_2$ requires 552.3). $^1$H NMR ($CDCl_3$, 400 MHz, a mixture of two rotamers): 7.82 and 7.68 (AB pattern, $J_{ab}$=8.2 Hz, 2H), 7.76 and 7.72 (AB pattern, $J_{ab}$=8.4 Hz, 2H), 7.60-7.48 (m, 2H), 7.05-7.00 (m, 2H), 4.90 and 4.78 (AB pattern, $J_{ab}$=16 Hz, 1H), 4.69 (s, 1H), 4.30-3.71 (m, 6H), 3.25 (m, 4H), 3.02-2.75 (m, 4H), 2.70-2.65 (m, 2H), 2.60-2.53 (m, 2H), 2.23 (s, 1.5H), 2.18 (s, 1.5H).

Example 7

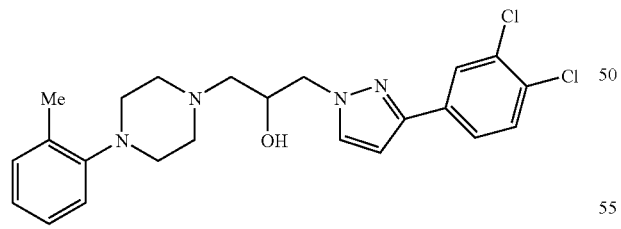

1-[3-(3,4-Dichloro-phenyl)-pyrazol-1-yl]-3-(4-o-tolyl-piperazin-1-yl)-propan-2-ol

A. 3-(3,4-Dichloro-phenyl)-1-oxiranylmethyl-1H-pyrazole

A stirred solution of 3-(3,4-dichlorophenyl)pyrazole (300 mg, 1.4 mmol) in DMF (5 mL) was treated with cesium carbonate (550 mg, 1.69 mmol) and epichlorohydrin (1.1 mL, 14.0 mmol) at room temperature for 18 h. The crude reaction mixture was then partitioned between EtOAc (50 mL) and water (35 mL). The aqueous phase was further extracted (2×50 mL) and the combined organic layers were washed with brine, dried ($Na_2SO_4$), filtered and concentrated under reduced pressure to yield crude product. Purification by column chromatography (silica, 25% EtOAc/hexanes) afforded 308 mg (82%) of the title compound. $^1$NMR (400 MHz, $CDCl_3$): 7.83 (d, J=2 Hz, 1H), 7.54 (dd, J=2, 8 Hz, 1H), 7.44 (d, J=2 Hz, 1H), 7.38 (d, J=8 Hz, 1H), 6.48 (d, J=2 Hz, 1H), 4.45 (dd, J=3, 9.7 Hz, 1H), 4.12 (dd, J=6, 15 Hz, 1H), 3.31 (m, 1H), 2.81 (dd, J=4.0, 4.6 Hz, 1H), 2.47 (dd, J=2.6, 4.7 Hz, 1H).

B. 1-[3-(3,4-Dichloro-phenyl)-pyrazol-1-yl]-3-(4-o-tolyl-piperazin-1-yl)-propan-2-ol A solution of 3-(3,4-dichloro-phenyl)-1-oxiranylmethyl-1H-pyrazole (30 mg, 0.11 mmol) and 1-(2-methylphenyl)-piperazine (22 mg, 0.12 mmol) in EtOH (1 mL) was heated to 80° C. overnight. Removal of solvent and purification by column chromatography (silica, 0-5% acetone/$CH_2Cl_2$) afforded 35 mg (70%) of the title compound. $^1$H NMR (400 MHz, $CDCl_3$): 7.89 (d, J=2 Hz, 1H), 7.61 (dd, J=2, 8.7 Hz, 1H), 7.57 (d, J=2 Hz, 1H), 7.45 (d, J=8.4 Hz, 1H), 7.16 (m, 2H), 6.99 (m, 2H), 6.54 (d, J=2.3 Hz, 1H), 4.31 (m, 1H), 4.18 (m, 2H), 2.93 (m, 4H), 2.60 (m, 2H), 2.47 (m, 3H), 2.88 (s, 3H).

Example 8

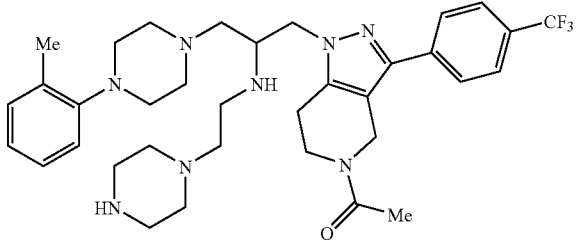

1-[1-[2-(2-Piperazin-1-yl-ethylamino)-3-(4-o-tolyl-piperazin-1-yl)-propyl]-3-(4-trifluoromethyl-phenyl)-1,4,6,7-tetrahydro-pyrazolo[4,3-c]pyridin-5-yl]-ethanone

A. 1-[5-Acetyl-3-(4-trifluoromethyl-phenyl)-4,5,6,7-tetrahydro-pyrazolo[4,3-c]pyridin-1-yl]-3-(4-o-tolyl-piperazin-yl)-propan-2-one A solution of DMSO (3.55 mL, 50 mmol) in $CH_2Cl_2$ (7 mL) was treated with oxalyl chloride (2.90 mL, 33 mmol) at −78° C. and stirred for 30 min. A solution of 1-[1-[2-hydroxy-3-(4-o-tolyl-piperazin-1-yl)-propyl]-3-(4-trifluoromethyl-phenyl)-1,4,6,7-tetrahydro-pyrazolo[4,3-c]pyridin-5-yl]-ethanone (1.8 g, 3.3 mmol) in $CH_2Cl_2$ (7 mL) was then slowly added and the reaction mixture was stirred for an additional 30 min before it was quenched with addition of triethylamine (18.4 mL, 132 mmol). The reaction mixture was slowly warmed to 25° C. and diluted with EtOAc (50 mL) and sat. $NaHCO_3$ (30 mL). The organic layer was separated, washed with $H_2O$ (2×50 mL), dried over $Na_2SO_4$, and concentrated. Column chromatography (silica, 2-5% $MeOH/CH_2Cl_2$)

afforded 1.50 g (83%) of a light yellow powder. TLC (silica, 10% MeOH/CH$_2$Cl$_2$): R$_f$=0.35. MS (electrospray): m/z 540.3 ([M+H]$^+$, C$_{29}$H$_{32}$F$_3$N$_5$O$_2$ requires 539.3). $^1$H NMR (CDCl$_3$, 400 MHz, a mixture of two rotamers): 7.78 and 7.62 (AB pattern, J$_{ab}$=8.2 Hz, 2H), 7.70 and 7.64 (AB pattern, J$_{ab}$=8.4 Hz, 2H), 7.18-6.95 (m, 4H), 5.10 (s, 1H), 5.07 (s, 1H), 4.84 (s, 1H), 4.68 (s, 1H), 3.96 (t, J=4.4 Hz, 1H), 3.78 (t, J=4.4 Hz, 1H), 3.47 (3.47 (s, 4H), 3.34 (s, 2H), 2.74-2.65 (m, 6H), 2.29 (s, 3H), 2.20 (s, 1.5H), 2.17 (s, 1.5H).

B. 1-1-[2-(2-piperazin-1-yl-ethylamino)-3-(4-o-tolyl-piperazin-1-yl)-propyl]-3-(4-trifluoromethyl-phenyl)-1,4,6,7-tetrahydro-pyrazolo[4,3-c]pyridin-5-yl]-ethanone A solution of 1-[5-acetyl-3-(4-trifluoromethyl-phenyl)-4,5,6,7-tetrahydro-pyrazolo[4,3-c]pyridin-1-yl]-3-(4-o-tolyl-piperazin-1-yl)-propan-2-one (54 mg, 0.1 mmol) in 1,2-dichloroethane (0.5 mL) was treated with 1-(2-aminoethyl)piperazine (26 μL, 0.2 mmol) and glacial acetic acid (34 μL, 0.6 mmol) at 25° C. and stirred for 30 min. Sodium triacetoxyborohydride (63.6 mg, 0.3 mmol) was added and the reaction mixture was stirred for an additional 4 h before it was quenched with CH$_2$Cl$_2$ (5 mL) and sat. NaHCO$_3$ (5 mL). The organic layer was separated, washed with H$_2$O (2×5 mL), dried over Na$_2$SO$_4$, and concentrated. Preparative TLC (silica, 10% MeOH/CH$_2$Cl$_2$) afforded 22 mg (35%) of a light yellow film. TLC (10% MeOH/CH$_2$Cl$_2$): R$_f$=0.2. MS (electrospray): m/z 653.3 ([M+H]$^+$, C$_{35}$H$_{47}$F$_3$N$_8$O requires 652.4). $^1$H NMR (CDCl$_3$, 400 MHz, a mixture of two rotamers): 7.78-7.60 (m, 4H), 7.18-6.82 (m, 4H), 4.88-4.30 (m, 2H), 4.23-3.90 (m, 2H), 3.85-3.70 (m, 2H), 3.22-2.85 (m, 10H), 2.85-2.30 (m, 15H), 2.30 (s, 3H), 2.21 (s, 1.5H), 2.17 (s, 1.5H).

Example 9

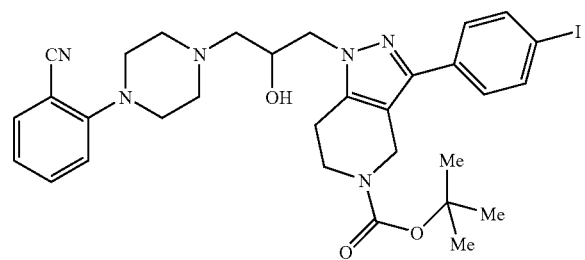

1-{3-[4-(2-Cyano-phenyl)-piperazin-1-yl]-2-hydroxy-propyl}-3-(4-iodo-phenyl)-1,4,6,7-tetrahydro-pyrazolo[4,3-c]pyridine-5-carboxylic acid tert-butyl ester

A. 3-(4-Iodo-phenyl)-1,4,6,7-tetrahydro-pyrazolo[4,3-c]pyridine-5-carboxylic acid tert-butyl ester p-Toluenesulfonic acid (0.055 g. 0.29 mmol) and morpholine (4.76 mL, 54 mmol) were added to a solution of tert-butyl 4-oxo-1-piperidinecarboxylate (10.3 g. 52 mmol) in benzene (22 mL). The reaction mixture was heated in a flask equipped with a condenser and a Dean-Stark trap at reflux for 20 h. The reaction mixture was cooled and concentrated in vacuo to give the enamine which was used without further purification. The enamine was dissolved in CH$_2$Cl$_2$ (60 mL) and cooled to 0° C. Triethylamine (8.67 mL, 62 mmol) was added, followed by dropwise addition of 4-iodobenzoyl chloride (13.8 g, 52 mmol) dissolved in CH$_2$Cl$_2$ (10 mL). The reaction mixture was allowed to warm to room temperature and stirred for 72 h. The reaction mixture was poured over water (200 mL) and the CH$_2$Cl$_2$ layer was separated, dried (Na$_2$SO$_4$), and concentrated. The resulting oil was taken up in EtOH (200 mL) and treated with hydrazine (4.88 mL, 155 mmol) at 0° C. The reaction mixture was allowed to warm to room temperature and stirred for 17 h. The mixture was concentrated and the resulting material was triturated with EtOAc to afford 9.52 g (43%) of a white solid. TLC (silica, 10% acetone/CH$_2$Cl$_2$): R$_f$=0.18. MS (electrospray): m/z 426.0 (426.1 calculated for C$_{17}$H$_{20}$IN$_3$O$_2$, [M+H]$^+$). $^1$H NMR (400 MHz, CDCl$_3$): 7.74 (br s, 2H), 7.31 (br d, J=8.0 Hz, 2H), 4.63 (br s, 2H), 3.73 (br s, 2H), 2.77 (br s, 2H), 1.49 (s, 9H).

B. 3-(4-Iodo-phenyl)-1-oxiranylmethyl-1,4,6,7-tetrahydro-pyrazolo[4,3-c]pyridine-5-carboxylic acid tert-butyl ester Cesium carbonate (1.84 g, 5.65 mmol) was added to a solution of epichlorohydrin (3.68 mL, 47.05 mmol) and 3-(4-iodo-phenyl)-1,4,6,7-tetrahydro-pyrazolo[4,3-c]pyridine-5-carboxylic acid tert-butyl ester (2.0 g, 4.71 mmol) in DMF (10 mL). The reaction mixture was allowed to stir for 24 h, then partitioned between aqueous NaHCO$_3$ and EtOAc. The aqueous layer was extracted with EtOAc and the combined organic layers were washed with water and brine, dried (Na$_2$SO$_4$), and concentrated. Purification by column chromatography (silica, 0-10% acetone/CH$_2$Cl$_2$) afforded 2.26 g (69%) of a white foam. TLC (silica, 10% acetone/CH$_2$Cl$_2$): R$_f$=0.44. MS (electrospray): m/z 482.0 (482.1 calculated for C$_{20}$H$_{24}$IN$_3$O$_3$, [M+H]$^+$). $^1$H NMR (400 MHz, CDCl$_3$): 7.60 (br s, 2H), 7.28 (br d, J=8.2 Hz, 2H), 4.48 (br s, 2H), 4.32 (br d, J=14.8 Hz, 1H), 3.99 (dd, J=15.0, 5.4 Hz, 1H), 3.61 (br s, 1H), 3.26-3.20 (m, 1H), 2.72 (t, J=4.4 Hz, 1H), 2.65-2.58 (m, 2H), 2.40 (br s, 1H), 1.36 (s, 9H).

C. 1-{3-[4-(2-Cyano-phenyl)-piperazin-1-yl]-2-hydroxy-propyl}-3-(4-iodo-phenyl)-1,4,6,7-tetrahydropyrazolo[4,3-c]pyridine-5-carboxylic acid tert-butyl ester Ytterbium (III) trifluoromethanesulfonate hydrate (0.193 g, 0.311 mmol) and 1-(2-cyanophenyl)-piperazine (0.292 g, 1.56 mmol) were dissolved in CH$_2$Cl$_2$ (2 mL) and added to a solution of 3-(4-iodo-phenyl)-1-oxiranylmethyl-1,4,6,7-tetrahydro-pyrazolo[4,3-c]pyridine-5-carboxylic acid tert-butyl ester in CH$_2$Cl$_2$ (5 mL). The reaction mixture was allowed to stir for 48 h at 25° C. Purification by flash chromatography (silica, 0-15% acetone/CH$_2$Cl$_2$) afforded 392 mg (56%) of a white foam. TLC (silica, 10% acetone/CH$_2$Cl$_2$): R$_f$=0.41. MS (electrospray): m/z 669.2 (669.2 calculated for C$_{31}$H$_{37}$IN$_6$O$_3$, [M+H]$^+$). $^1$H NMR (400 MHz, CDCl$_3$): 7.73 (br s, 2H), 7.58-7.56 (m, 1H), 7.52-7.48 (m, 1H), 7.39 (br d, J=7.1 Hz, 2H), 7.04-7.00 (m, 2H), 4.60 (br s, 2H), 4.06-4.04 (m, 2H), 4.06-4.04 (m, 1H), 3.76-3.70 (m, 2H), 3.26 (br s, 4H), 2.84-2.38 (m, 7H), 1.56-1.53 (m, 2H), 1.48 (s, 9H).

Example 10

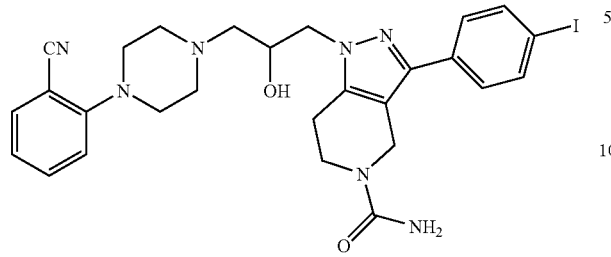

1-{3-[4-(2-Cyano-phenyl)-piperazin-1-yl]-2-hydroxy-propyl}-3-(4-iodo-phenyl)-1,4,6,7-tetrahydro-pyrazolo[4,3-c]pyridine-5-carboxylic acid amide

A. 2-(4-{2-Hydroxy-3-[3-(4-iodo-phenyl)-4,5,6,7-tetrahydro-pyrazolo[4,3-c]pyridin-1-yl]-propyl}-piperazin-1-yl)-benzonitrile Trifluoroacetic acid (3 mL) was added to a solution of 1-{3-[4-(2-cyano-phenyl)-piperazin-1-yl]-2-hydroxy-propyl}-3-(4-iodo-phenyl)-1,4,6,7-tetrahydro-pyrazolo[4,3-c]pyridine-5-carboxylic acid tert-butyl ester (0.402 g, 0.601 mmol) in $CH_2Cl_2$ (3 mL) and the reaction mixture was stirred for 2 h. The mixture was concentrated, then diluted with EtOAc. The organic layer was washed with aqueous $NaHCO_3$ and brine, dried ($Na_2SO_4$), and concentrated to afford the amine (0.342 g, 100%) as a yellowish foam. TLC (silica, 10% acetone/$CH_2Cl_2$): $R_f$=0.14. MS (electrospray): m/z 569.2 (569.1, calculated for $C_{26}H_{29}IN_6O$, [M+H]$^+$). $^1$H NMR (400 MHz, $CDCl_3$:$CD_3OD$(6:1)): 7.73 (d, J=8.6 Hz, 2H), 7.56 (dd, J=7.6, 1.8 Hz, 1H), 7.52 (t, J=8.0 Hz, 1H), 7.25 (d, J=8.6 Hz, 2H), 7.09 (t, J=7.6 Hz, 1H), 7.02 (dd, J=8.4 Hz, 1H), 4.43-4.36 (m, 1H), 4.31 (s, 2H), 4.21 (dd, J=14.1, 4.5 Hz, 1H), 4.11 (dd, J=14.5, 6.3 Hz, 1H), 3.54-3.49 (m, 2H), 3.40-3.24 (m, 8H), 3.18-3.06 (m, 3H), 3.03-2.95 (m, 3H).

B. 1-{3-[4-(2-Cyano-phenyl)-piperazin-1-yl]-2-hydroxy-propyl}-3-(4-iodo-phenyl)-1,4,6,7-tetrahydro-pyrazolo[4,3-c]pyridine-5-carboxylic acid amide Diisopropylethylamine (0.531 mL, 3.05 mmol), DMAP (5 mg), and trimethylsilyl isocyanate (0.413 mL, 3.05 mmol) were added to a solution of 2-(4-{2-hydroxy-3-[3-(4-iodo-phenyl)-4,5,6,7-tetrahydro-pyrazolo[4,3-c]pyridin-1-yl]-propyl}-piperazin-1-yl)-benzonitrile in pyridine (3 mL) and $CH_2Cl_2$ (6 mL). The reaction mixture was stirred for 20 h, then partitioned between aqueous $NaHCO_3$ and $CH_2Cl_2$. The $CH_2Cl_2$ layer was washed with brine, dried ($Na_2SO_4$), and concentrated. The resulting product was dissolved in $CH_2Cl_2$ (5 mL) and treated with 21 wt % sodium ethoxide in EtOH (0.5 mL) for 3 h. The reaction mixture was washed with brine, dried ($Na_2SO_4$), and concentrated. Purification by column chromatography (silica, 0-10% MeOH/$CH_2Cl_2$) afforded 290 mg (78%) of the title compound. HPLC (reverse phase conditions), $t_R$=4.21 min. MS (electrospray): m/z 612.2 (612.5, calculated for $C_{27}H_{30}IN_7O_2$, M$^+$+H). $^1$H NMR (400 MHz, $CDCl_3$): 7.73 (d, J=8.6 Hz, 2H), 7.57 (dd, J=7.6, 1.6 Hz, 1H), 7.50 (t, J=7.8 Hz, 1H), 7.36 (d, J=8.6 Hz, 2H), 7.05 (t, J=7.6 Hz, 1H), 7.00 (d, J=8.4 Hz, 1H), 4.64 (br s, 2H), 4.57 (br s, 2H), 4.30 (br s, 1H), 4.20 (dd, J=14.1, 3.3 Hz, 1H), 4.06 (dd, J=14.1, 6.3 Hz, 1H), 3.82-3.65 (m, 2H), 3.29-3.20 (m, 4H), 3.04-2.80 (m, 6H), 2.68 (br s, 2H).

Example 11

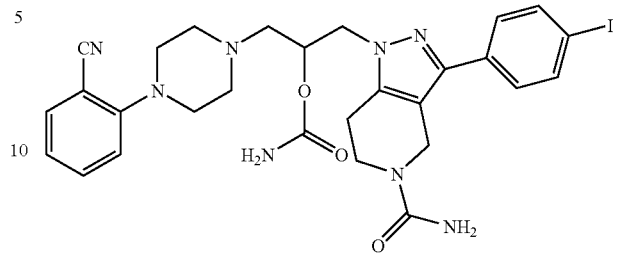

Carbamic acid 1-[5-carbamoyl-3-(4-iodo-phenyl)-4,5,6,7-tetrahydro-pyrazolo[4,3-c]pyridin-1-ylmethyl]-2-[4-(2-cyano-phenyl)-piperazin-1-yl]-ethyl ester The title compound (13 mg, 3%) was obtained along with 1-{3-[4-(2-cyano-phenyl)-piperazin-1-yl]-2-hydroxy-propyl}-3-(4-iodo-phenyl)-1,4,6,7-tetrahydro-pyrazolo[4,3-c]pyridine-5-carboxylic acid as described in example 10. MS (electrospray): m/z 655.2 (655.2, calculated for $C_{28}H_{31}IN_8O_3$, [M+H]$^+$). HPLC (reverse phase conditions): $t_R$=6.29 min. $^1$H NMR (400 MHz, $CDCl_3$): 7.69 (d, J=8.1 Hz, 2H), 7.50 (d, J=7.52, 1H), 7.43 (t, J=8.1 Hz, 1H), 7.31 (d, J=8.1 Hz, 2H), 6.96 (t, J=9.0 Hz, 2H), 4.64 (br s, 2H), 4.08 (d, J=16.8 Hz, 2H), 3.96 (dd, J=14.0, 6.6 Hz, 1H), 3.80-3.69 (m, 2H), 3.10-2.80 (m, 4H), 2.66 (br s, 2H), 2.50 (br s, 2H).

Example 12

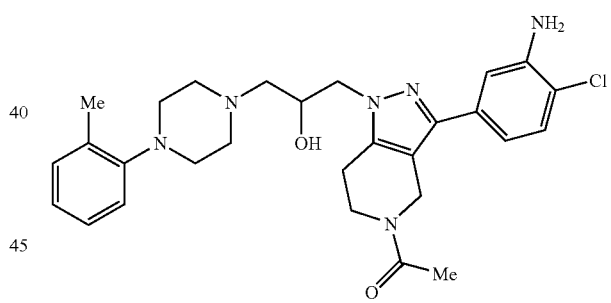

1-{3-(3-Amino-4-chloro-phenyl)-1-[2-hydroxy-3-(4-o-tolyl-piperazin-1-yl)-propyl]-1,4,6,7-tetrahydro-pyrazolo[4,3-c]pyridin-5-yl}-ethanone

A. 1-[3-(4-Chloro-3-nitro-Phenyl)-1,4,6,7-tetrahydro-pyrazolo[4,3-c]pyridin-5-yl]-ethanone A flask equipped with a Dean-Stark trap was charged with N-acetyl-4-piperidone (27.29 g, 137 mmol), piperidine (16.5 mL, 129 mmol), p-toluene-sulfonic acid (0.5 g) and benzene (150 mL). The mixture was heated to 125° C. After 8 h the mixture was allowed to cool, and concentrated in vacuo to give the corresponding enamine (35 g). A solution of the enamine (3.87 g, 20.0 mmol) in dichloromethane (24 mL) was treated with triethylamine (3.07 mL, 22.0 mmol) and 4-chloro-3-nitrobenzoyl chloride (4.84 g, 22.0 mmol). The reaction mixture was stirred at 0° C. for 1 h and then at room temperature for 16 h. Hydrazine (1.88 mL, 60 mmol) was added to the reaction mixture. This solution was stirred at room temperature for an additional 16 h. The solvents were removed under reduced pressure. Ethyl acetate (100 mL) was added to the residue to form a suspension. This suspension was filtered and dried to afford 6.4 g (100%) of a yellow solid. MS (electrospray): m/z 321.0 (321.0, calculated for $C_{14}H_{13}ClN_4O_3$, [M+H]$^+$). $^1$H NMR (CDCl$_3$, 400 MHz, a mixture of two rotamers): 8.10-8.00 (m, 3H), 4.90 (s, 0.8H), 4.85 (s, 1.2H), 3.96 (m, 2H), 2.95 (m, 2H), 2.20 (s, 3H).

B. 1-[3-(4-Chloro-3-nitro-phenyl)-1-oxiranyl methyl-1,4,6,7-tetrahydro-pyrazolo[4,3-c]pyridin-5-yl]-ethanone A solution of 1-[3-(4-chloro-3-nitro-phenyl)-1,4,6,7-tetrahydro-pyrazolo[4,3-c]pyridin-5-yl]-ethanone (6.4 g, 20.0 mmol) in DMF (60 mL) was treated with cesium carbonate (13.0 g, 40 mmol) and epichlorohydrin (15.6 mL, 200.0 mmol) at room temperature. The reaction mixture was stirred at room temperature for an additional 24 h before it was diluted with ethyl acetate (350 mL) and water (50 mL). The organic layer was separated, washed with water (2×50 mL), brine (50 mL), dried over sodium sulfate, and concentrated under reduced pressure. The residue was purified by column chromatography (silica, 10% acetone/CH$_2$Cl$_2$) to provide 7.5 g (83%) of a light yellow powder. MS (electrospray): m/z 377.0 (377.0, calculated for $C_{17}H_{17}ClN_4O_4$, [M+H]$^+$). $^1$H NMR (CDCl$_3$, 400 MHz, a mixture of two rotamers): 8.15-8.05 (m, 1H), 7.75-7.65 (m, 1H), 7.55-7.45 (m, 1H), 4.80-4.65 (m, 1.2H), 4.60 (s, 0.8H), 4.45-4.35 (m, 1H), 4.08-4.02 (m, 1H), 3.92-3.80 (m, 1H), 3.70-3.63 (m, 1H), 3.30-3.20 (m, 1H), 2.90-2.67 (m, 3H), 2.55-2.48 (m, 1H), 2.15 (s, 1.7H), 2.10 (s, 1.3H).

C. 1-{3-(4-Chloro-3-nitro-phenyl)-1-[2-hydroxy-3-(4-o-tolyl-piperazin-1-yl)-propyl]-1,4,6,7-tetrahydro-pyrazolo[4,3-c]pyridin-5-yl}-ethanone A solution of 1-[3-(4-chloro-3-nitro-phenyl)-1-oxiranylmethyl-1,4,6,7-tetrahydro-pyrazolo[4,3-c]pyridin-5-yl]-ethanone (0.754 g, 2.0 mmol) in dichloromethane (10 mL) was treated with ytterbium(III) triflate (0.25 g, 0.40 mmol) and 1-(2-methylphenyl)-piperazine (0.705 g, 4.0 mmol) at room temperature. The reaction mixture was stirred at room temperature for 16 h and diluted with dichloromethane (100 mL) and water (50 mL). The organic layer was separated, washed with water (2×50 mL), dried over sodium sulfate and concentrated under reduced pressure. The residue was purified by column chromatography (silica, 5% MeOH/CH$_2$Cl$_2$) to afford 0.98 g (90%) of the desired product as a light yellow solid. MS (electrospray): m/z 553.2 (553.2, calculated for $C_{28}H_{33}ClN_6O_4$, [M+H]$^+$). $^1$H NMR (CDCl$_3$, 400 MHz, a mixture of two rotamers): 8.25-8.15 (m, 1H), 7.75-7.70 (m, 1H), 7.63-7.55 (m, 1H) 7.20-7.10 (m, 2H), 7.05-6.95 (m, 2H), 4.90-4.70 (m, 1H), 4.65 (s, 1H), 4.30-4.15 (m, 2H), 4.10-3.70 (m, 4H), 3.00-2.40 (m, 12H), 2.20 (s, 3H), 2.15 (s, 1.5H), 2.10 (s, 1.5H).

D. 1-{3-(3-amino-4-chloro-phenyl)-1-[2-hydroxy-3-(4-o-tolyl-piperazin-1-yl)-propyl]-1,4,6,7-tetrahydro-pyrazolo[4,3-c]pyridin-5-yl}-ethanone To a solution of sodium hydrosulfite (1.28 g, 7.3 mmol) in 30 mL water was added 1-{3-(4-chloro-3-nitro-phenyl)-1-[2-hydroxy-3-(4-o-tolyl-piperazin-1-yl)-propyl]-1,4,6,7-tetrahydro-pyrazolo[4,3-c]pyridin-5-yl}-ethanone (810 mg, 1.5 mmol) in 15 mL THF. The reaction mixture was stirred at room temperature for 5 min. The color of the solution changed from light yellow to colorless. Hydrochloride solution (1 N, 10 mL) was added to the reaction mixture. This solution was stirred at room temperature for 30 min, and treated with saturated sodium bicarbonate until the pH of the solution between 7 to 8. The product was extracted with dichloromethane (3×80 mL). The organic phases were combined, dried over sodium sulfate, and concentrated under reduced pressure to a residue. This residue was purified by column chromatography (silica, 5-20% MeOH/CH$_2$Cl$_2$) to afford 644 mg (84.1%) of the title compound. MS (electrospray): m/z 523.3 (523.3, calculated for $C_{28}H_{35}ClN_6O_2$, [M+H]$^+$). $^1$H NMR (CDCl$_3$, 400 MHz, a mixture of two rotamers): 7.30-6.70 (m, 7H), 4.80-4.60 (m, 1H), 4.55 (s, 1H), 4.20-4.05 (m, 4H), 3.95-3.90 (m, 2H), 3.80-3.60 (m, 2H), 2.90-2.30 (m, 9H), 2.20 (s, 3H), 2.15 (s, 1.5H), 2.10 (s, 1.5H).

Example 13

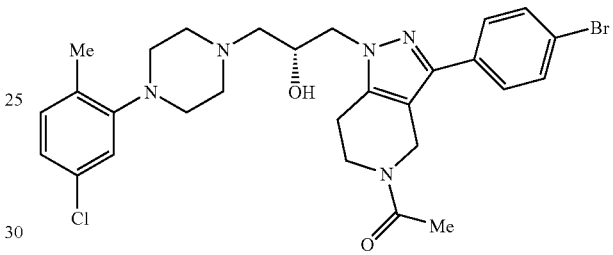

(R)-1-(3-(4-Bromo-phenyl)-1-{3-[4-(5-chloro-2-methyl-phenyl)-piperazin-1-yl]-2-hydroxy-propyl}-1,4,6,7-tetrahydro-pyrazolo[4,3-c]pyridin-5-yl)-ethanone A. (2S)-1-tert-Butyldimethylsilylglycidol tert-Butylchlorodimethylsilane (9.41 g, 62.4 mmol) followed by Et$_3$N (13.5 mL, 96.8 mmol) was added to a 0° C. solution of R-(+)-glycidol (3.88 g, 52.4 mmol) in CH$_2$Cl$_2$ (100 mL). The solution was allowed to warm to 23° C. with stirring over 17 h. The resulting pink solution was diluted with Et$_2$O (250 mL) and stirred an additional 30 min. The solution was partitioned between Et$_2$O (800 mL) and sat. aqueous NaHCO$_3$ (200 mL). The Et$_2$O layer was washed with sat. aqueous NaHCO$_3$ (250 mL), H$_2$O (3×200 mL), brine (100 mL), dried over Na$_2$SO$_4$ and concentrated. Purification of the residue by column chromatography (silica, 5-10% Et$_2$O/hexanes) provided 8.21 g (84%) of the title compound. TLC (silica, 10% Et$_2$O/hexanes): R$_f$ 0.5. $^1$H NMR (CDCl$_3$, 400 MHz): 3.85 (dd, J=11.9, 3.2 Hz, 1H), 3.66 (dd, J=11.9, 4.8 Hz, 1H), 3.09 (m, 1H), 2.77 (dd, J=5.0, 4.2 Hz, 1H), 2.64 (dd, J=5.2, 2.7 Hz, 1H), 0.90 (s, 9H), 0.08 (s, 3H), 0.07 (s, 3H).

B. 1-[3-(4-Bromo-phenyl)-1,4,6,7-tetrahydro-pyrazolo[4,3-c]pyridin-5-yl]-ethanone A flask equipped with a Dean-Stark trap was charged with N-acetyl-4-piperidone (100.1 g, 709 mmol), piperidine (68 mL, 779 mmol), pTsOH (3.7 g) and benzene (500 mL). The mixture was heated to 125° C. After 17 h the mixture was allowed to cool and divided into two portions. A solution of p-bromobenzoyl chloride (70.0 g, 319 mmol) in CH$_2$Cl$_2$ (400 mL) was added dropwise to a 0° C. solution of the enamine (ca. 355 mmol) in CH$_2$Cl$_2$ (320 mL) over 15 h. The mixture was then allowed to warm to 23° C. and stirred for an additional 5 h. The solution was treated with 1 N HCl (500 mL) and stirred vigorously for 1.5 h. The layers were separated and the aqueous layer was extracted with CH$_2$Cl$_2$ (2×300 mL). The combined extracts were washed with sat. aqueous NaHCO$_3$ (300 mL), H$_2$O (300 mL), brine (300 mL), dried over Na$_2$SO$_4$ and concentrated. The residue was dissolved in MeOH (300 mL) and treated with NH$_2$NH$_2$ (50.0 mL, 1.59 mol). The mixture was stirred for 17 h before the precipitate formed was collected by filtration and air dried to give 52 g (50%) of the title compound which was suitable for use without further purification. TLC (silica, 5% MeOH/CH$_2$Cl$_2$): R$_f$=0.3. MS (electrospray): m/z calculated for C$_{14}$H$_{15}$$^{79}$BrN$_3$O [M+H]$^+$, 320.04, found 320. $^1$H NMR (CD$_3$OD/CDCl$_3$, 400 MHz, a mixture of amide rotamers): 7.53 and 7.35 (A and B of AA'BB', J=8.5 Hz, 2H), 7.51 and 7.39 (A and B of AA'BB', J=8.6 Hz, 2H), 4.72 (s, 2H), 4.58 (s, 2H), 3.85 (t, J=5.9 Hz, 2H), 3.71 (t, J=5.8 Hz, 2H), 2.81, (t, J=5.8 Hz, 2H), 2.74, (t, J=5.8 Hz, 2H), 2.16 (s, 3H), 2.11 (s, 3H).

C. (S)-1-[3-(4-Bromo-phenyl)-1-oxiranylmethyl-1,4, 6,7-tetrahydro-pyrazolo[4,3-c]pyridin-5-yl]-ethanone A solution of KHMDS in toluene (0.5 M, 3.7 mL, 1.85 mmol) was added to a 0° C. solution of 1-[3-(4-bromo-phenyl)-1,4,6,7-tetrahydro-pyrazolo[4,3-c]pyridin-5-yl]-ethanone (492 mg, 1.54 mmol) in DMF (4.0 mL). The mixture was stirred for 1 h before (2S)-1-tert-butyldimethylsilylglycidol (870 mg, 4.62 mmol) was added neat via syringe. The mixture was stirred an additional 48 h and partitioned between EtOAc (300 mL) and sat. aqueous NaHCO$_3$ (100 mL). The aqueous layer was extracted with EtOAc (2×100 mL). The combined extracts were washed with H$_2$O (2×100 mL), brine (100 mL), dried over Na$_2$SO$_4$ and concentrated. The residue was dissolved in MeOH (50 mL) and treated with CSA (97 mg). The mixture was stirred for 17 h and concentrated to dryness. The residue was suspended in MeC(OMe)$_3$ (50 mL) and stirred for an additional 17 h. The mixture was diluted with EtOAc (400 mL) and washed with saturated aqueous NaHCO$_3$ (50 mL), H$_2$O (2×50 mL), brine (50 mL), dried over Na$_2$SO$_4$ and concentrated. The crude orthoester was dissolved in CH$_2$Cl$_2$ (5 mL), cooled to 0° C., and treated with AcBr (0.18 mL, 2.4 mmol). The mixture was allowed to warm with stirring over 4 h before being worked up as described above. The crude acetyl-bromide obtained was dissolved in MeOH (50 mL), treated with K$_2$CO$_3$ (207 mg, 1.50 mmol) and stirred for 4 h. The reaction mixture was diluted with EtOAc (400 mL) and washed with saturated aqueous NH$_4$Cl (100 mL). The EtOAc layer was washed with H$_2$O (2×100 mL), brine (100 mL), dried over Na$_2$SO$_4$ and concentrated. The crude product was purified by column chromatography (silica, 10-40% acetone/CH$_2$Cl$_2$) to afford 158 mg (27%) of the title compound. Chiral HPLC (Daicel OD, 0.5% Et$_2$NH/MeOH) analysis indicated >95% optical purity. HPLC (reverse phase conditions): t$_R$=4.90 min. MS (electrospray): m/z calculated for C$_{17}$H$_{19}$$^{79}$BrN$_3$O$_2$ [M$^+$+H], 376.07, found 376.0. $^1$H NMR (CDCl$_3$, 400 MHz, a mixture of amide rotamers): 7.47 (d with fine splittings (partially obscured), J=8.5, Hz, 2H), 7.44 (m, 4H), 7.38 (d with fine splittings, J=8.5, Hz, 2H), 4.71 and 4.64 (A and B of AB quartet, J$_{ab}$=15.7 Hz, 2H), 4.51 (s, 2H), 4.39 (dd, J=15.1, 2.5 Hz, 1H), 4.34 (dd, J=15.0, 2.9 Hz, 1H), 4.02 (dd, J=5.2, 3.9 Hz, 1H), 3.98 (dd, J=5.3, 3.7 Hz, 1H), 3.83 (m, 2H), 3.64 (m, 2H), 3.25 (br m, 2H), 2.80-2.60 (m, 6H), 2.46 (dd, J=4.6, 2.6 Hz, 1H), 2.38 (dd, J=4.6, 2.6 Hz, 1H), 2.10 (s, 3H), 2.06 (s, 3H).

D. (R)-1-(3-(4-Bromo-phenyl)-1-{3-[4-(5-chloro-2-methyl-phenyl)-piperazin-1-yl]-2-hydroxy-propyl}-1,4,6,7-tetrahydro-pyrazolo[4,3-c]pyridin-5-yl)-ethanone (S)-1-[3-(4-Bromo-phenyl)-1-oxiranylmethyl-1,4,6,7-tetrahydro-pyrazolo[4,3-c]pyridin-5-yl]-ethanone (37 mg, 0.98 mmol) and 4-(2-methyl-5-chlorophenyl)piperazine (36 mg, 0.17 mmol) were combined in EtOH (0.4 mL) and heated to 70° C. After 18 h the mixture was allowed to cool, diluted with CH$_2$Cl$_2$ and purified by preparative TLC (silica, 8% MeOH/CH$_2$Cl$_2$) to give 35 mg (61%) the title compound. HPLC (reverse phase conditions): t$_R$=4.41 min. MS (electrospray): m/z calculated for C$_{28}$H$_{34}$$^{35}$Cl$^{79}$BrN$_5$O$_2$ [M$^+$+H], 586.16, found 586.2. $^1$H NMR (CDCl$_3$, 400 MHz, a mixture of amide rotamers): 7.56 (d (partially obscured), J=8.5, Hz, 2H), 7.53 (s, 4H), 7.48 (d, J=8.5 Hz, 2H), 7.08 (br d, J=8.5 Hz, 1H), 6.95 (m, 2H), 4.85 and 4.73 (A and B of AB quartet, J$_{ab}$=15.6 Hz, 1H), 4.62 (s, 1H), 4.20 (m, 2H), 4.04 (m, 2H), 3.90-3.71 (m, 2H), 2.92-2.53 (m, 11H), 2.21 (s, 1.5H), 2.16 (s, 1.5H).

Example 14

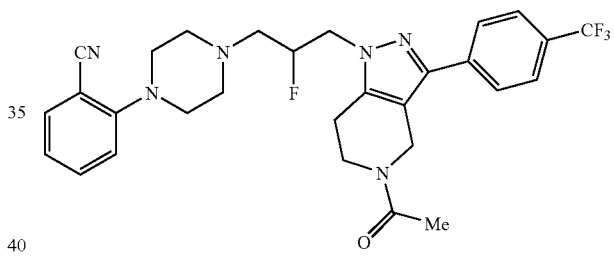

2-(4-{3-[5-Acetyl-3-(4-trifluoromethyl-phenyl)-4,5, 6,7-tetrahydro-pyrazolo[4,3-c]pyridin-1-yl]-2-fluoro-propyl}-piperazin-1-yl)-benzonitrile A solution of 2-(4-{3-[5-acetyl-3-(4-trifluoromethyl-phenyl)-4,5,6,7-tetrahydro-pyrazolo[4,3-c]pyridin-1-yl]-2-hydroxy-propyl}-piperazin-1-yl)-benzonitrile (150 mg, 0.27 mmol) in CH$_2$Cl$_2$ (1 mL) was treated with DAST (Et$_2$NSF$_3$, 7 µL, 0.60 mmol) at −78° C. The reaction mixture was slowly warmed to 25° C. for 1 h and then to 60° C. for an additional 2 h. Preparative TLC (silica, 5% MeOH/CH$_2$Cl$_2$) provided 75 mg (50%) of the title compound as a light yellow powder. TLC (5% MeOH/CH$_2$Cl$_2$): R$_f$=0.28. MS (electrospray): m/z 555.2 ([M+H]$^+$, C$_{29}$H$_{30}$F$_4$N$_6$O requires 554.2). $^1$H NMR (CDCl$_3$, 400 MHz, a mixture of two rotamers): 7.71 and 7.59 (AB pattern, J$_{ab}$=8.2 Hz, 2H), 7.66 and 7.62 (AB pattern, J$_{ab}$=8.4 Hz, 2H), 7.50-7.38 (m, 2H), 6.96-6.92 (m, 2H), 5.01 (dp, J=49.0, 3.0 Hz, 1H), 4.77 and 4.73 (AB pattern, J$_{ab}$=15.7 Hz, 1.1H), 4.59 (s, 0.9H), 4.41-4.18 (m, 2H), 3.95-3.80 (m, 1H), 3.69 (dd, J=5.5, 5.5 Hz, 1H), 3.18 (m, 4H), 2.83-2.65 (m, 8H), 2.14 (s, 1.6H), 2.10 (s, 1.4H).

Example 15

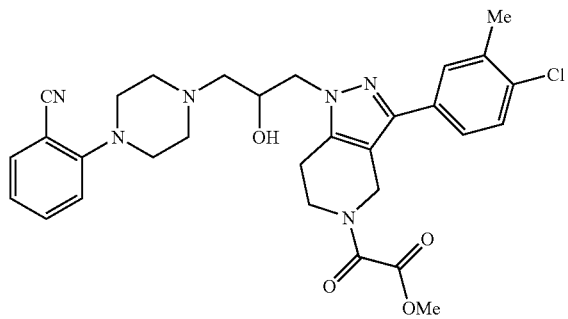

(3-(4-Chloro-3-methyl-phenyl)-1-{3-[4-(2-cyano-phenyl)-piperazin-1-yl]-2-hydroxy-propyl}-1,4,6,7-tetrahydro-pyrazolo[4,3-c]pyridin-5-yl)-oxo-acetic acid methyl ester

A. 4-Chloro-3-methyl-benzoyl chloride

To a suspension of 52.55 g (0.31 mol) of 4-chloro-3-methyl-benzoic acid in $CH_2Cl_2$ (1.2 L) with DMF (1 mL) at 0° C. under $N_2$ with an outlet sparging through 2.5 N sodium hydroxide was added 29.56 mL (0.339 mol) of oxalyl chloride. The mixture was allowed to warm to room temperature over a 3 h period. The reaction mixture was concentrated and taken forward crude.

B. 3-(4-Chloro-3-methyl-phenyl)-1,4,6,7-tetrahydro-pyrazolo[4,3-c]pyridine-5-carboxylic acid tert-butyl ester To a stirred solution of 55.8 g (0.28 mol) of 4-oxo-piperidine-1-carboxylic acid tert-butyl ester and 25.7 g (0.29 mol) of morpholine in benzene (125 mL) was added a catalytic amount (~0.25 g) of p-toluenesulfonic acid. The mixture was heated to reflux for 10 h under a Dean-Stark trap. The solvent was removed under reduced pressure to give a brown oil. The crude product was diluted with $CH_2Cl_2$ (400 mL), and 46.83 mL (0.34 mol) of $Et_3N$ was added. The mixture was cooled to 0° C., and a solution of 4-chloro-3-methyl-benzoyl chloride (0.35 mol) in $CH_2Cl_2$ (200 mL) was added slowly by dropping funnel over 2 h. The reaction mixture was poured over water (400 mL) and the $CH_2Cl_2$ layer was separated, dried ($Na_2SO_4$), and concentrated. The resulting oil was taken up in EtOH (400 mL) and treated with 35 mL of hydrazine at 0° C. The reaction mixture was allowed to warm to room temperature and stirred for 17 h, during which time a white precipitate formed. The volume of the reaction mixture was reduced to ~150 mL, and $Et_2O$ (750 mL) was added. The suspension was stirred vigorously for 2 h and was filtered then washed with $Et_2O$ (2×200 mL) and dried under vacuum to afford 50.74 g (52% over 3 steps) of 3-(4-chloro-3-methyl-phenyl)-1,4,6,7-tetrahydro-pyrazolo[4,3-c]pyridine-5-carboxylic acid tert-butyl ester as a pale orange solid. MS (electrospray): exact mass calculated for $C_{18}H_{22}ClN_3O_2$, 347.1; m/z found, 348.1 [M+H]$^+$. $^1$H NMR (400 MHz, CDCl$_3$): 7.26-7.43 (m, 4H), 4.65 (br s, 2H), 3.73 (br s, 2H), 2.77 (br s, 2H), 2.34 (s, 3H), 1.49 (s, 9H).

C. 3-(4-Chloro-3-methyl-phenyl)-1-oxiranylmethyl-1,4,6,7-tetrahydro-pyrazolo[4,3-c]pyridine-5-carboxylic acid tert-butyl ester To a solution of 3-(4-chloro-3-methyl-phenyl)-1,4,6,7-tetrahydro-pyrazolo[4,3-c]pyridine-5-carboxylic acid tert-butyl ester (18.26 g, 53 mmol) and epichlorohydrin (41.12 mL, 526 mmol) in DMF (100 mL) was added cesium carbonate (20.56 g, 63 mmol). The reaction mixture was allowed to stir for 72 h, diluted with EtOAc (200 mL) and washed with saturated $NaHCO_3$ and brine. The organic layer was dried over $Na_2SO_4$, concentrated and purified by column chromatography (silica, 20% acetone/$CH_2Cl_2$) to afford 3-(4-chloro-3-methyl-phenyl)-1-oxiranylmethyl-1,4,6,7-tetrahydro-pyrazolo[4,3-c]pyridine-5-carboxylic acid tert-butyl ester (12.0 g, 57%). TLC (silica, 20% acetone/$CH_2Cl_2$): $R_f$=0.68. MS (electrospray) m/z 491.2 (491.2, calculated for $C_{27}H_{31}ClN_6O$, [M+H]$^+$). $^1$H NMR (400 MHz, CDCl$_3$) 7.55 (s, 1H), 7.36 (m, 2H), 4.61 (m, 2H), 4.38-4.47 (m, 1H), 4.11 (dd, J=14.3, 5.7 Hz, 1H), 3.67-3.79 (m, 2H), 3.34 (m, 1H), 2.83 (t, J=4.5 Hz, 1H), 2.75 (m, 2H), 2.51 (m, 1H), 2.41 (s, 3H), 1.48 (s, 9H).

D. 3-(4-Chloro-3-methyl-phenyl)-1-{3-[4-(2-cyano-phenyl)-piperazin-1-yl]-2-hydroxy-propyl}-1,4,6,7-tetrahydro-pyrazolo[4,3-c]pyridine-5-carboxylic acid tert-butyl ester 3-(4-Chloro-3-methyl-phenyl)-1-oxiranylmethyl-1,4,6,7-tetrahydro-pyrazolo[4,3-c]pyridine-5-carboxylic acid tert-butyl ester (5.33 g, 13.2 mmol) and 1-(2-cyanophenyl)-piperazine (2.97 g, 15.86 mmol) were partially dissolved in EtOH (50 mL) and triethylamine (2 mL). The reaction mixture was heated to 80° C. for 18 h. The mixture was concentrated and purified by column chromatography (silica, 20% acetone/$CH_2Cl_2$) to give 3-(4-chloro-3-methyl-phenyl)-1-{3-[4-(2-cyano-phenyl)-piperazin-1-yl]-2-hydroxy-propyl}-1,4,6,7-tetrahydro-pyrazolo[4,3-c]pyridine-5-carboxylic acid tert-butyl ester (6.51 g, 83%) as a yellow solid. TLC (silica, 20% acetone/$CH_2Cl_2$): $R_f$=0.35. MS (electrospray): m/z 591.3 (591.3, calculated for $C_{32}H_{39}ClN_6O_3$, [M+H]$^+$).

E. 2-(4-{3-[3-(4-Chloro-3-methyl-phenyl)-4,5,6,7-tetrahydro-pyrazolo[4,3-c]pyridin-1-yl]-2-hydroxy-propyl}-piperazin-1-yl)-benzonitrile 3-(4-Chloro-3-methyl-phenyl)-1-{3-[4-(2-cyano-phenyl)-piperazin-1-yl]-2-hydroxy-propyl}-1,4,6,7-tetrahydro-pyrazolo[4,3-c]pyridine-5-carboxylic acid tert-butyl ester (1.26 g, 2.13 mmol) was dissolved in trifluoroacetic acid (3 mL) and $CH_2Cl_2$ (3 mL) and allowed to stir for 2 h. The reaction mixture was concentrated, taken up in EtOAc (50 mL) and washed with aqueous $NaHCO_3$ (2×25 mL). The EtOAc layer was dried over $Na_2SO_4$ and concentrated to give 2-(4-{3-[3-(4-chloro-3-methyl-phenyl)-4,5,6,7-tetrahydro-pyrazolo[4,3-c]pyridin-1-yl]-2-hydroxy-propyl}-piperazin-1-yl)-benzonitrile (1.05 g, 99%) as a yellow foam. TLC (silica, 10% MeOH/$CH_2Cl_2$): $R_f$=0.27. MS (electrospray): m/z 491.2 (491.2, calculated for $C_{27}H_{31}ClN_6O$, [M+H]$^+$). $^1$H NMR (400 MHz, CDCl$_3$): 9.8 (br s, 1H), 7.55 (d, J=7.6 Hz, 1H), 7.50 (t, J=8.2 Hz, 1H), 7.38 (s, 1H), 7.31 (d, J=8.2 Hz, 1H), 7.20 (d, J=8.2 Hz, 1H), 7.11 (t, J=8.2 Hz, 1H), 6.98 (d, J=8.2 Hz, 1H), 4.56 (br s, 1H), 4.12-4.32 (m, 4H), 2.98-3.51 (m, 13H), 2.35 (s, 3H).

F. (3-(4-Chloro-3-methyl-phenyl)-1-{3-[4-(2-cyano-phenyl)-piperazin-1-yl]-2-hydroxy-propyl}-1,4,6,7-tetrahydro-pyrazolo[4,3-c]pyridin-5-yl)-oxo-acetic acid methyl ester 2-(4-{3-[3-(4-Chloro-3-methyl-phenyl)-4,5,6,7-tetrahydro-pyrazolo[4,3-c]pyridin-1-yl]-2-hydroxy-propyl}-piperazin-1-yl)-benzonitrile (58 mg, 0.118 mmol) was dissolved in $CH_2Cl_2$ (0.59 mL) and treated with methyl chlorooxoacetate (16 mg, 0.129 mmol). The reaction mixture was allowed to stir for 18 h at room temperature. Column chromatography (silica, 2-10% MeOH/CH$_2$Cl$_2$) gave (3-(4-chloro-3-methyl-phenyl)-1-{3-[4-(2-cyano-phenyl)-piperazin-1-yl]-2-hydroxy-propyl}-1,4,6,7-tetrahydro-pyrazolo[4,3-c]pyridin-5-yl)-oxo-acetic acid methyl ester (54 mg, 79%) as a white solid. MS (electrospray): m/z 577.3 (577.2, calculated for C$_{30}$H$_{33}$ClN$_6$O$_4$, [M+H]$^+$). $^1$H NMR (400 MHz, CDCl$_3$): 7.32-7.62 (m, 5H), 7.14 (t, J=7.6 Hz, 1H), 7.05 (d, J=8.2 Hz, 1H), 4.59-4.80 (m, 3H), 4.12-4.28 (m, 2H), 3.92 (s, 3H), 3.78-3.86 (m, 2H), 3.44-3.60 (m, 5H), 3.15-3.40 (m, 4H), 2.83-3.05 (m, 2H), 2.41 (s, 3H).

Example 16

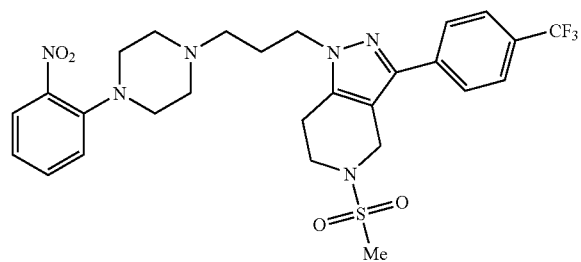

5-Methanesulfonyl-1-{3-[4-(2-nitro-phenyl)-piperazin-1-yl]-propyl}-3-(4-trifluoromethyl-phenyl)-4,5,6,7-tetrahydro-1H-pyrazolo[4,3-c]pyridine A. 1-Methanesulfonyl-piperidin-4-one Potassium carbonate (324 g, 2340 mmol) was added to a solution of 4-piperidone monohydrate hydrochloride (90 g, 586 mmol) in chloroform (300 mL) and water (300 mL). The slurry was cooled to 0° C. and treated with methylsulfonyl chloride (136 mL, 1760 mmol) by dropwise addition over a 1 h period (gas evolution was observed). The reaction mixture was allowed to shake for 72 h and was partitioned between CH$_2$Cl$_2$ (500 mL) and saturated aqueous NaHCO$_3$ (500 mL). The aqueous layer was extracted with CH$_2$Cl$_2$ (3×200 mL). The organic layer was washed with 1% KHSO$_4$ (250 mL), dried (Na$_2$SO$_4$), and concentrated to afford 90.5 g (87%) of a white solid. MS (electrospray): exact mass calculated for C$_6$H$_{11}$NO$_3$S, 177.1; m/z found, 178.1 [M+H]$^+$. HPLC (reverse phase conditions): t$_R$=2.19 min. $^1$H NMR (400 MHz, CDCl$_3$): 3.60 (t, J=6.5 Hz, 4H), 2.89 (s, 3H), 2.59 (t, J=6.3 Hz, 4H).

B. 5-Methanesulfonyl-3-(4-trifluoromethyl-phenyl)-4,5,6,7-tetrahydro-1H-pyrazolo[4,3-c]pyridine p-Toluenesulfonic acid (1.34 g, 7.0 mmol) and morpholine (25.83 mL, 296 mmol) were added to a solution of 1-methanesulfonyl-piperidin-4-one (50.0 g, 282 mmol) in benzene (282 mL). The reaction mixture was heated in a flask equipped with a condenser and a Dean-Stark trap at reflux for 15 h. The reaction mixture was cooled and concentrated in vacuo to give the enamine which was used without further purification. The enamine was dissolved in CH$_2$Cl$_2$ (200 mL) and cooled to 0° C. To this was added triethylamine (47.2 mL, 339 mmol) followed by dropwise addition of 4-trifluoromethylbenzoyl chloride (42.3 mL, 285 mmol) dissolved in CH$_2$Cl$_2$ (82 mL). The reaction mixture was allowed to warm to room temperature and stirred for 20 h. The reaction mixture was washed with 1 N aqueous HCl (250 mL) and the CH$_2$Cl$_2$ layer was separated, dried (Na$_2$SO$_4$), and concentrated. The resulting oil was taken up in EtOH (300 mL) and treated with hydrazine (44.3 mL, 1.41 mol) at 0° C. The reaction mixture was allowed to warm to room temperature and stirred for 24 h. The mixture was concentrated and the resulting solid was filtered with EtOH wash and dried in vacuo to afford 70 g (72%) of 5-methanesulfonyl-3-(4-trifluoromethyl-phenyl)-4,5,6,7-tetrahydro-1H-pyrazolo[4,3-c]pyridine as a white solid. MS (electrospray): exact mass calculated for C$_{14}$H$_{14}$F$_3$N$_3$O$_2$S, 345.0; m/z found, 346.0 [M+H]$^+$. HPLC (reverse phase conditions): t$_R$=6.33 min. $^1$H NMR (400 MHz, CDCl$_3$): 7.72 (s, 4H), 4.58 (s, 2H), 3.69 (t, J=5.7 Hz, 2H), 2.99 (t, J=5.7 Hz, 2H), 2.92 (s, 3H).

C. 3-[5-Methanesulfonyl-3-(4-trifluoromethyl-phenyl)-4,5,6,7-tetrahydro-pyrazolo[4,3-c]pyridin-1-yl]-propan-1-ol Cs$_2$CO$_3$ (33.74 g, 103.5 mmol) was added to a solution of 5-methanesulfonyl-3-(4-trifluoromethyl-phenyl)-4,5,6,7-tetrahydro-1H-pyrazolo[4,3-c]pyridine (29.8 g, 86.3 mmol) in anhydrous DMF (70 mL) and stirred for 25 min. 3-Bromo-1-propanol (8.6 mL, 13.2 g, 94.9 mmol) was added and stirred under N$_2$ at room temperature for 18 h. Water (500 mL) was added to the reaction and stirred for 5 min. The precipitated material was filtered out and washed with water (4×100 mL) and dried in a Freeze Drying System. The crude material (31.0 g) was taken up in anhydrous DMF (65 mL) and Cs$_2$CO$_3$ (33.74 g, 103.5 mmol) was added, and stirred for 10 min. 3-Bromo-1-propanol (8.6 mL, 13.2 g, 94.9 mmol) and MeOH (6.0 mL, 4.75 g, 148 mmol) were added and stirring continued under N$_2$ at room temperature for 15 h. Water (500 mL) was added to the reaction and stirred for 10 min. The precipitated material was filtered and washed with water (3×100 mL). The filter cake was dissolved in CH$_2$Cl$_2$ (200 mL) and washed with brine (50 mL), dried (Na$_2$SO$_4$), and concentrated. The solid was triturated with Et$_2$O (200 mL), filtered, washed with Et$_2$O, and dried to furnish 16.0 g of the desired compound. The mother liquor was chromatographed (silica, 0-10% acetone/EtOAc) to obtain an additional 3.0 g of the title compound. The combined yield was 54.6%. MS (electrospray): calculated for C$_{17}$H$_{20}$F$_3$N$_3$O$_3$S, 403.12; m/z found, 404.0 [M+H]$^+$, 426.0 [M+Na]$^+$. $^1$H NMR (400 MHz, CDCl$_3$): 7.71 (d, J=8.2 Hz, 2H), 7.66 (d, J=8.5 Hz, 2H), 4.55 (s, 2H), 4.23 (t, J=6.5 Hz, 2H), 3.70-3.63 (m, 4H), 2.90 (s, 3H), 2.90 (t, J=5.1 Hz, 2H), 2.62 (t, J=5.9 Hz, 1H), 2.06 (q, J=6.1 Hz, 2H).

D. 3-[5-Methanesulfonyl-3-(4-trifluoromethyl-phenyl)-4,5,6,7-tetrahydro-pyrazolo[4,3-c]pyridin-1-yl]-Propionaldehyde Dess-Martin periodinane (3.45 g, 8.2 mmol) was added to a solution of 3-[5-methanesulfonyl-3-(4-trifluoromethyl-phenyl)-4,5,6,7-tetrahydro-pyrazolo[4,3-c]pyridin-1-yl]-propan-1-ol (3.0 g, 7.4 mmol) in CH$_2$Cl$_2$ (20 mL) at 0° C. under N$_2$. After 15 min, the reaction was allowed to warm to room temperature and stirred for another 1.5 h. The reaction was diluted with Et$_2$O (60 mL) and 20% aq. NaHCO$_3$ (35 mL) was added slowly. Then Na$_2$S$_2$O$_3$ was added and stirred at room temperature for 30 min. The layers were separated and the aqueous portion was extracted with Et$_2$O (2×30 mL). The combined organic extracts were washed with brine, dried (Na$_2$SO$_4$) and concentrated. MPLC (1-10% MeOH/CH$_2$Cl$_2$) afforded 2.53 g of the desired aldehyde in 85% yield. MS (electrospray): calculated for $C_{17}H_{18}F_3N_3O_3S$, 401.11; m/z found, 402.1 [M+H], 434.1 [M+MeOH+H]. $^1$H NMR (400 MHz, CDCl$_3$): 9.82 (s, 1H), 7.63 (d, J=8.4 Hz, 2H), 7.58 (d, J=8.4 Hz, 2H), 4.68 (s, 2H), 4.25 (t, J=6.1 Hz, 2H), 3.63 (t, J=5.8 Hz, 4H), 3.14 (t, J=6.1 Hz, 2H), 2.92 (t, J=5.8 Hz, 2H), 2.81 (s, 3H).

E. 5-Methanesulfonyl-[1-3-[4-(2-nitro-phenyl)-piperazin-1-yl]-propyl]-3-(4-trifluoromethyl-phenyl)-4,5,6,7-tetrahydro-1H-pyrazolo[4,3-c]pyridine To a stirred solution of 3-[5-methanesulfonyl-3-(4-trifluoromethyl-phenyl)-4,5,6,7-tetrahydro-pyrazolo[4,3-c]pyridin-1-yl]-propionaldehyde (0.060 g, 0.15 mmol) and 1-(2-nitro-phenyl)-piperazine (0.032 g, 0.157 mmol) in CH$_2$Cl$_2$ (0.5 mL), glacial AcOH (8.5 µL, 0.15 mmol) was added and stirred for 15 min at room temperature. NaBH(OAc)$_3$ (0.041 g, 0.19 mmol) was added and stirred under nitrogen overnight. Saturated NaHCO$_3$ (0.5 mL) was then added and stirred for 15 min. The layers separated and the aqueous layer was extracted with CH$_2$Cl$_2$ (0.5 mL). MPLC purification (silica, 2-15% MeOH/CH$_2$Cl$_2$) afforded the desired product as a white solid (0.063 g, 71%). TLC (silica, 12% MeOH/CH$_2$Cl$_2$): R$_f$=0.67. MS (electrospray): exact mass calculated for $C_{27}H_{31}F_3N_6O_4S$, 592.21; m/z found, 593.2 [M+H]$^+$. $^1$H NMR (400 MHz, CDCl$_3$): 7.80 (dd, J=1.6, 8.2 Hz, 1H), 7.77 (d, J=8.3 Hz, 2H), 7.70 (d, J=8.3 Hz, 2H), 7.52 (ddd, J=1.6, 7.3, 8.3 Hz, 1H), 7.19 (dd, J=1.2, 8.3 Hz, 1H), 7.09 (m, 1H), 4.59 (s, 2H), 4.17 (t, J=6.9 Hz, 2H), 3.71 (t, J=5.8 Hz, 2H), 3.13 (br t, J=4.8 Hz, 4H), 2.96 (t, J=5.6 Hz, 2H), 2.95 (s, 3H), 2.66 (br t, J=4.4 Hz, 4H), 2.51 (t, J=7.0 Hz, 2H), 2.17 (q, J=6.9 Hz, 2H).

Example 17

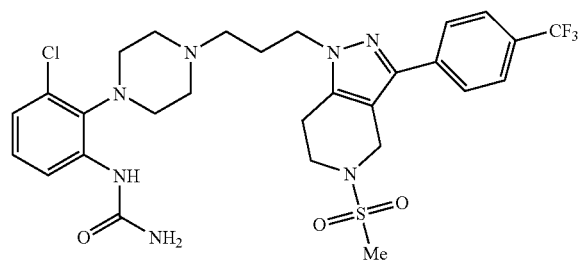

1-[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-3-methyl-urea A. 4-(2-chloro-6-nitro-phenyl)-piperazine-1-carboxylic acid tert-butyl ester To a stirred solution of 1,2-dichloro-3-nitrobenzene (0.96 g, 5.0 mmol) and piperazine-1-carboxylic acid tert-butyl ester (0.93 g, 5.0 mmol) in acetonitrile (5 mL) was added of K$_2$CO$_3$ (1.38 g, 10 mmol). The mixture was heated at reflux for 48 h. The solvent was removed under reduced pressure. The crude material was partitoned between EtOAc (100 mL) and H$_2$O (20 mL). The organic layer was washed with H$_2$O (2×20 mL), dried over Na$_2$SO$_4$ and concentrated. Column chromatography (silica, 10-20% EtOAc/hexanes) provided 4-(2-chloro-6-nitro-phenyl)-piperazine-1-carboxylic acid tert-butyl ester (1.2 g, 70%). TLC (silica, 20% EtOAc/hexanes): R$_f$=0.45. MS (electrospray): exact mass calculated for $C_{15}H_{20}ClN_3O_4$, 341.1; m/z found, 364.1 [M+Na]$^+$. $^1$H NMR (400 MHz, CDCl$_3$) 7.56 (dd, J=8.2, 1.4 Hz, 1H), 7.50 (dd, J=8.2, 1.4 Hz, 1H), 7.13 (t, J=8.2 Hz, 1H), 3.38-3.56 (m, 4H), 3.06 (m, 4H), 1.48 (s, 9H).

B. 1-(2-chloro-6-nitro-phenyl)-piperazine 4-(2-Chloro-6-nitro-phenyl)-piperazine-1-carboxylic acid tert-butyl ester (1.87 g, 5.47 mmol) was dissolved in trifluoroacetic acid (5.0 mL) and CH$_2$Cl$_2$ (5.0 mL) and allowed to stir for 2 h. The reaction mixture was concentrated, diluted with EtOAc, and washed with saturated aq. NaHCO$_3$. The organic layer was dried over Na$_2$SO$_4$, concentrated and purified by column chromatography (silica, 100% CH$_2$Cl$_2$) to afford 1-(2-chloro-6-nitro-phenyl)-piperazine (1.26 g, 95%). MS (electrospray): exact mass calculated for $C_{10}H_{12}ClN_3O_2$, 241.1; m/z found, 242.1 [M+H]$^+$. $^1$H NMR (400 MHz, CDCl$_3$): 7.54 (dd, J=8.2, 1.6 Hz, 1H), 7.49 (dd, J=8.2, 1.6 Hz, 1H), 7.10 (t, J=8.2 Hz, 1H), 3.08 (br s, 4H), 2.99 (br s, 4H), 2.07-2.12 (m, 1H).

C. 1-{3-[4-(2-Chloro-6-nitro-phenyl)-piperazin-1-yl]-propyl}-5-methanesulfonyl-3-(4-trifluoromethyl-phenyl)-4,5,6,7-tetrahydro-1H-pyrazolo[4,3-c]pyridine To a stirred solution of 3-[5-methanesulfonyl-3-(4-trifluoromethyl-phenyl)-4,5,6,7-tetrahydro-pyrazolo[4,3-c]pyridin-1-yl]-propionaldehyde (0.5 g, 1.25 mmol) and 1-(2-chloro-6-nitrophenyl)-piperazine (0.301 g, 1.25 mmol) in CH$_2$Cl$_2$ (6 mL) was added sodium sulfate (0.354 g, 2.50 mmol) and sodium triacetoxyborohydride (0.396 g, 1.87 mmol). The mixture was allowed to stir at room temperature overnight. The mixture was diluted with CH$_2$Cl$_2$ and washed with water. The CH$_2$Cl$_2$ layer was dried over Na$_2$SO$_4$, and the solvent was removed under reduced pressure. The residue was purified by column chromatography (silica, 10% acetone/CH$_2$Cl$_2$) to afford of 1-{3-[4-(2-chloro-6-nitro-phenyl)-piperazin-1-yl]-propyl}-5-methanesulfonyl-3-(4-trifluoromethyl-phenyl)-4,5,6,7-tetrahydro-1H-pyrazolo[4,3-c]pyridine (0.380 g, 49%). MS (electrospray): exact mass calculated for $C_{27}H_{30}ClF_3N_6O_4S$, 626.2; m/z found, 627.2 [M+H]$^+$. $^1$H NMR (400 MHz, CDCl$_3$): 7.73 (d, J=8.2 Hz, 2H), 7.66 (d, J=8.2 Hz, 2H), 7.54 (dd, J=8.2, 1.2 Hz, 1H), 7.49 (dd, J=8.2, 1.2 Hz, 1H), 7.10 (t, J=8.2 Hz, 1H), 4.58 (s, 2H), 4.13 (t, J=6.5 Hz, 2H), 3.71 (t, J=5.9 Hz, 2H), 3.01-3.11 (m, 4H), 2.95 (t, J=5.9 Hz, 2H), 2.92 (s, 3H), 2.42-2.53 (m, 4H), 2.40 (t, J=6.5 Hz, 2H), 2.12 (q, J=6.5 Hz, 2H).

D. 3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenylamine To a stirred solution of 1-{3-[4-(2-chloro-6-nitro-phenyl)-piperazin-1-yl]-propyl}-5-methanesulfonyl-3-(4-trifluoromethyl-phenyl)-4,5,6,7-tetrahydro-1H-pyrazolo[4,3-c]pyridine (0.153 g, 0.244 mmol) in EtOH (2.44 mL) was added zinc dust (0.80 mg, 1.22 mmol) and slow addition of acetic acid (0.70 mL). After 15 min the yellow solution became colorless and the access zinc dust was filtered through a plug of celite. The filtrate was concentrated and the residue was purified by column chromatography (silica, 0-10% MeOH/CH$_2$Cl$_2$) to afford 3-chloro-2-(4-{3-[5-methanesulfonyl-3-(4-trifluoromethyl-phenyl)-4,5,6,7-tetrahydro-pyrazolo[4,3- c]pyridin-1-yl]-propyl}-piperazin-1-yl)-phenylamine (0.146 g, 100%). MS (electrospray): exact mass calculated for $C_{27}H_{32}ClF_3N_6O_2S$, 596.2; m/z found, 597.2 [M+H]$^+$. $^1$H NMR (400 MHz, CDCl$_3$): 7.73 (d, J=8.2 Hz, 2H), 7.66 (d, J=8.2 Hz, 2H), 6.88 (t, J=8.2 Hz, 1H), 6.63 (t, J=7.6 Hz, 2H), 4.55 (s, 2H), 4.36 (s, 2H), 4.15 (t, J=6.5 Hz, 2H), 3.60-3.70 (m, 4H), 2.97 (t, J=5.3 Hz, 2H), 2.90 (s, 3H), 2.83 (d, J=10.8 Hz, 2H), 2.74 (d, J=11.5 Hz, 2H), 2.37 (t, J=6.6 Hz, 2H), 2.11-2.20 (m, 4H).

E. 1-[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl-3-methyl-urea To a stirred solution of 3-chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenylamine (0.062 g, 0.104 mmol) in CH$_2$Cl$_2$ (0.52 mL) was added trimethylsilyl isocyanate (0.017 mL, 0.125 mmol). The reaction mixture was allowed to stir for 48 h at room temperature. The reaction had not gone to completion, so an additional 0.017 mL (0.125 mmol) of trimethylsilyl isocyanate was added and the reaction was heated to 45° C. for 10 h. Column chromatography (silica, 3-10% MeOH/CH$_2$Cl$_2$) afforded 1-[3-chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-3-methyl-urea (0.015 g, 22%). MS (electrospray): exact mass calculated for $C_{28}H_{33}ClF_3N_7O_3S$, 639.2; m/z found, 640.2 [M+H]$^+$. $^1$H NMR (400 MHz, CDCl$_3$): 8.26 (br s, 1H), 8.05 (d, J=8.2 Hz, 1H), 7.73 (d, J=8.2 Hz, 2H), 7.66 (d, J=8.2 Hz, 2H), 7.09 (t, J=8.2 Hz, 1H), 6.92 (d, J=8.2 Hz, 1H), 4.65 (s, 2H), 4.55 (s, 2H), 4.15 (t, J=6.7 Hz, 2H), 3.65-3.73 (m, 4H), 2.96 (t, J=5.6 Hz, 2H), 2.87-2.92 (m, 2H), 2.91 (s, 3H), 2.70 (d, J=11.4 Hz, 2H), 2.40 (t, J=6.7 Hz, 2H), 2.09-2.22 (m, 4H).

Example 18

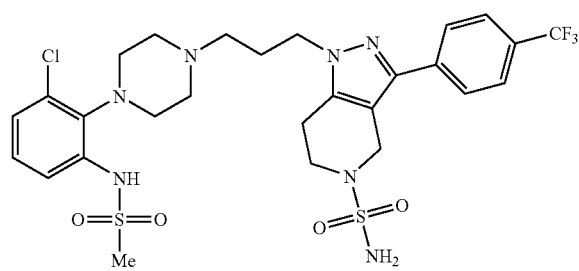

1-{3-[4-(2-Chloro-6-methanesulfonylamino-phenyl)-piperazin-1-yl]-propyl}-3-(4-trifluoromethyl-phenyl)-1,4,6,7-tetrahydro-pyrazolo[4,3-c]pyridine-5-sulfonic acid amide

A. 3-(4-Trifluoromethyl-phenyl)-1,4,6,7-tetrahydro-pyrazolo[4,3-c]pyridine-5-carboxylic acid tert-butyl ester To a stirred solution of 500 g (2.51 mol) of 1-tert-butoxycarbonyl-4-piperidone and 87.1 g (2.76 mol) of morpholine in benzene (1.25 L) was added a catalytic amount (~0.25 g) of p-TsOH. The mixture was heated to reflux for 36 h with a Dean-Stark trap. One half of the solvent was removed under reduced pressure and the resulting solution was cooled and filtered. The filtrate was then concentrated to yield 630 g (94%) of an orange red oil. The eneamine was divided and 320 g (1.19 mol) was diluted with CH$_2$Cl$_2$ (1.0 L) and 165.0 mL (1.19 mol) of Et$_3$N was added. The mixture was cooled to 0° C. and a solution of 225 g (1.08 mol) of 4-trifluoromethylbenzoyl chloride in CH$_2$Cl$_2$ (0.5 L) was added slowly by dropping funnel over 1 h. The mixture was allowed to warm to rt and stir overnight. The reaction was then diluted with 1 N HCl (450 mL) and stirred vigorously for 3 h. The aqueous layer was extracted with CH$_2$Cl$_2$ (3×500 mL) and the combined extracts were dried over Na$_2$SO$_4$ and the solvent was removed under reduced pressure. The crude oil was diluted with EtOH (1 L) and cooled to 0° C. To this stirred solution was slowly added 115 g (3.57 mol) of hydrazine and the mixture was allowed to warm to rt and stir overnight during which time a white precipitate formed. The volume of the reaction was reduced to ~500 mL and cooled. The precipitate was collected to afford 285 g (72% from eneamine) of a white solid. $^1$H NMR (400 MHz, CDCl$_3$): 7.63-7.55 (m, 4H), 4.58 (br s, 2H), 3.69-3.62 (br m, 2H), 2.74-2.68 (br m, 2H), 1.47 (s, 9H).

B. 1-(2-Methoxycarbonyl-ethyl)-3-(4-trifluoromethyl-Phenyl)-1,4,6,7-tetrahydro-pyrazolo[4,3-c]pyridine-5-carboxylic acid tert-butyl ester 3-(4-Trifluoromethyl-phenyl)-1,4,6,7-tetrahydro-pyrazolo[4,3-c]pyridine-5-carboxylic acid tert-butyl ester (1.85 g, 5.04 mmol) and methyl acrylate (0.50 mL, 5.6 mmol) were combined in toluene (30 mL) and heated to 75° C. The resulting mixture was treated with t-BuONa (100 mg), and heating continued for 48 h. The mixture was allowed to cool and partitioned between EtOAc (300 mL) and NaHCO$_3$ (75 mL). The aqueous layer was extracted with EtOAc (3×75 mL). The combined extracts were dried over Na$_2$SO$_4$ and concentrated. Column chromatography (silica, 30-60% EtOAc/hexanes) afforded 343 mg (15%) of the title compound. TLC (silica, 50% EtOAc/hexanes): R$_f$=0.4. MS (electrospray): m/z calculated for $C_{22}H_{27}F_3N_3O_4$ [M$^+$+H] 454.20, found 454.1. $^1$H NMR (CDCl$_3$, 400 MHz): 7.75 (br d, J=8.1 Hz, 2H), 7.64 (br s, 2H), 4.63 (br s, 2H), 4.30 (t, J=6.6 Hz, 2H), 3.75 (br s, 2H), 3.68 (s, 3H), 2.98 (t, J=6.6 Hz, 2H), 2.79 (br t, J=5.6 Hz, 2H), 1.48 (s, 9H).

C. 1-(3-Hydroxy-propyl)-3-(4-trifluoromethyl-phenyl)-1,4,6,7-tetrahydro-pyrazolo[4,3-c]pyridine-5-carboxylic acid tert-butyl ester A solution of LiBH$_4$ (26 mg, 1.2 mmol) in THF (0.5 mL) was added to a 0° C. solution of 1-(2-methoxycarbonyl-ethyl)-3-(4-trifluoromethyl-phenyl)-1,4,6,7-tetrahydro-pyrazolo[4,3-c]pyridine-5-carboxylic acid tert-butyl ester (317 mg, 0.70 mmol) in THF (4.0 mL). The mixture was stirred for 5 min then additional LiBH$_4$ (15 mg) was added and stirring continued for 17 h. The mixture was partitioned between EtOAc (80 mL) and saturated aqueous NaHCO$_3$ (20 mL). The aqueous layer was extracted with EtOAc (2×20 mL). The combined extracts were dried over Na$_2$SO$_4$ and concentrated. Column chromatography (silica, 0-8% MeOH/CH$_2$Cl$_2$) afforded 268 mg (95%) of the title compound. HPLC (reverse phase conditions), t$_R$=6.82 min. MS (electrospray): m/z calculated for $C_{21}H_{26}F_3N_3O_3$ [M$^+$+Na] 448.18, found 448.10. $^1$H NMR (CDCl$_3$, 400 MHz): 7.73 (br d, J=8.2 Hz, 2H), 7.65 (br s, 2H), 4.64 (br s, 2H), 4.21 (t, J=6.4 Hz, 2H), 3.76 (br s, 2H), 3.66 (t, J=5.7 Hz, 2H), 2.73 (br t, J=5.4 Hz, 2H), 2.04 (q, J=6.1 Hz, 2H), 1.48 (s, 9H).

D. 1-(3-Oxo-propyl)-3-(4-trifluoromethyl-phenyl)-1,4,6,7-tetrahydro-pyrazolo[4,3-c]pyridine-5-carboxylic acid tert-butyl ester Dess-Martin periodinane (1.43 g, 3.36 mmol) was added portion wise to a stirred solution of 1-(3-hydroxy-propyl)-3-(4-trifluoromethyl-phenyl)-1,4,6,7-tetrahydropyrazolo[4,3-c]pyridine-5-carboxylic acid tert-butyl ester (1.30 g, 3.05 mmol) in $CH_2Cl_2$ (15 mL) at 0° C. under $N_2$. Then the reaction was stirred at 0° C. for 15 min and allowed to warm to room temperature. After stirring at room temperature for 1.5 h the reaction was diluted with $Et_2O$ (50 mL) and saturated $NaHCO_3$ (15 mL) was added slowly (caution! gas evolution). Then $Na_2S_2O_3.5H_2O$ (5.31 g, 21.4 mmol) was added and stirred for 30 min. The layers were separated and the aqueous layer was extracted with $Et_2O$ (2×30 mL). The combined extracts were washed with brine, dried ($Na_2SO_4$) and concentrated. MPLC (1-10% MeOH/$CH_2Cl_2$) afforded the aldehyde in 79% yield (1.02 g). TLC (silica, 10% MeOH/$CH_2Cl_2$): $R_f$=0.67. MS (electrospray) calculated for $C_{21}H_{24}F_3N_3O_3$, 424.2 ([M+H]$^+$), m/z found, 424.2. $^1$H NMR (400 MHz, $CDCl_3$): 9.82 (s, 1H), 7.65 (br d, J=8.0 Hz, 2H), 7.54 (br s, 2H), 4.53 (s, 2H), 4.21 (t, J=6.2 Hz, 2H), 3.68 (br s, 2H), 3.04 (t, J=6.2 Hz, 2H), 2.70 (t, J=5.6 Hz, 2H), 1.39 (s, 9H).

E. 4-(2-Chloro-6-nitro-phenyl)-piperazine-1-carboxylic acid tert-butyl ester To a stirred solution of 0.96 g (5.0 mmol) of 1,2-dichloro-3-nitrobenzene and 0.93 g (5.0 mmol, 1 eq) of 1-tert-butyloxycarbonylpiperazine in acetonitrile (5 mL) was added 1.38 g (10 mmol, 2 eq) of $K_2CO_3$. The mixture was heated to reflux for 48 h. The solvent was removed under reduced pressure. The crude product was partitioned between EtOAc (100 mL) and 20 mL of $H_2O$. The organic layer was washed with $H_2O$ (2×20 mL), dried over $Na_2SO_4$ and concentrated. Column chromatography (silica, 10-20% EtOAc/hexanes) provided 1.2 g (70%) of 4-(2-chloro-6-nitro-phenyl)-piperazine-1-carboxylic acid tert-butyl ester. TLC (silica, 20% EtOAc/hexanes): $R_f$=0.45. $^1$H NMR (400 MHz, $CDCl_3$): 7.56 (dd, J=8.2, 1.4 Hz, 1H), 7.50 (dd, J=8.2, 1.4 Hz, 1H), 7.13 (t, J=8.2 Hz, 1H), 3.56-3.38 (m, 4H), 3.10-3.00 (m, 4H), 1.48 (s, 9H).

F. 1-{3-[4-(2-Chloro-6-nitro-phenyl)-piperazin-1-yl]-propyl}-3-(4-trifluoromethyl-phenyl)-1,4,6,7-tetrahydro-pyrazolo[4,3-c]pyridine-5-carboxylic acid tert-butyl ester 4-(2-Chloro-6-nitro-phenyl)-piperazine-1-carboxylic acid tert-butyl ester (940 mg, 2.75 mmol) in 10 mL of $CH_2Cl_2$ was treated with 5 mL of trifluoroacetic acid and stirred at 25° C. for 1 h. The volatiles were then removed. The residue was taken up in $CH_2Cl_2$ (60 mL) and KOH (4 N, 20 mL). The organic layer was separated, dried over $Na_2SO_4$, and concentrated. The yellow oil was dissolved in $CH_2Cl_2$ and added into the 996 mg (2.35 mmol) of 1-(3-oxo-propyl)-3-(4-trifluoromethyl-phenyl)-1,4,6,7-tetrahydro-pyrazolo[4,3-c]pyridine-5-carboxylic acid tert-butyl ester. The yellow solution was treated with glacial acetic acid (0.8 mL, 6 eq) and stirred at 25° C. for 1 h. NaBH(OAc)$_3$ (1.5 g, 7.05 mmol) was added and stirred under nitrogen for 2 h. Then saturated $NaHCO_3$ (20 mL) was added and stirred for 30 min, and the layers were separated. The organic extract was washed with brine, dried over $Na_2SO_4$, and concentrated under reduced pressure. Column chromatography (silica, 2-5% MeOH/$CH_2Cl_2$) afforded 1-{3-[4-(2-chloro-6-nitro-phenyl)-piperazin-1-yl]-propyl}-3-(4-trifluoromethyl-phenyl)-1,4,6,7-tetrahydro-pyrazolo[4,3-c]pyridine-5-carboxylic acid tert-butyl ester as a white solid (1.40 g, 92%). TLC (silica, 5% MeOH/$CH_2Cl_2$): $R_f$=0.3. MS (electrospray): exact mass calculated for $C_{31}H_{36}ClF_3N_6O_4$, 648.24; m/z found 649.3 [M+H]$^+$. $^1$H NMR (400 MHz, $CDCl_3$): 7.69 (d, J=8.2 Hz, 1H), 7.60-7.50 (m, 1H), 7.45-7.37 (m, 4H), 7.02 (t, J=8.2 Hz, 1H), 4.58 (br s, 2H), 4.04 (t, J=6.7 Hz, 2H), 3.73-3.65 (m, 2H), 3.05-2.95 (m, 4H), 2.71 (t, J=5.6 Hz, 2H), 2.50-2.35 (m, 4H), 2.30 (t, J=6.8 Hz, 2H), 2.05-1.95 (m, 2H), 1.41 (s, 9H).

G. 1-{3-[4-(2-Amino-6-chloro-phenyl)-piperazin-1-yl]-propyl}-3-(4-trifluoromethyl-phenyl)-1,4,6,7-tetrahydro-pyrazolo[4,3-c]pyridine-5-carboxylic acid tert-butyl ester A solution of 360 mg (0.56 mmol) of 1-{3-[4-(2-chloro-6-nitro-phenyl)-piperazin-1-yl]-propyl}-3-(4-trifluoromethyl-phenyl)-1,4,6,7-tetrahydro-pyrazolo[4,3-c]pyridine-5-carboxylic acid tert-butyl ester in 4 mL of MeOH was treated with 182 mg (5 eq) of zinc dust and glacial acetic acid (1.57 mL, 50 eq) at 25° C. The reaction mixture was stirred at 25° C. for 1 h. The reaction mixture was then filtered through a pad of celite and concentrated to obtain a thick oil. The residue was taken up in $CH_2Cl_2$ (50 mL) and sat. $NaHCO_3$ (20 mL). The organic layer was separated, washed with $H_2O$ (2×10 mL), dried over $Na_2SO_4$, and concentrated to afford 1-{3-[4-(2-amino-6-chloro-phenyl)-piperazin-1-yl]-propyl}-3-(4-trifluoromethyl-phenyl)-1,4,6,7-tetrahydro-pyrazolo[4,3-c]pyridine-5-carboxylic acid tert-butyl ester. TLC (silica, 10% MeOH/$CH_2Cl_2$): $R_f$=0.3. MS (electrospray): exact mass calculated for $C_{31}H_{38}ClF_3N_6O_2$, 618.27; m/z found, 619.3 [M+H]$^+$.

H. 1-{3-[4-(2-Chloro-6-methanesulfonylamino-phenyl)-piperazin-1-yl]-propyl}-3-(4-trifluoromethyl-phenyl)-1,4,6,7-tetrahydro-pyrazolo[4,3-c]pyridine-5-carboxylic acid tert-butyl ester A solution of 1-{3-[4-(2-amino-6-chloro-phenyl)-piperazin-1-yl]-propyl}-3-(4-trifluoromethyl-phenyl)-1,4,6,7-tetrahydro-pyrazolo[4,3-c]pyridine-5-carboxylic acid tert-butyl ester (257 mg, 0.42 mmol) in 4 mL of $CH_2Cl_2$ was treated with 32 μL (0.42 mmol, 1.0 eq) of methanesulfonyl chloride and 116 μL (0.83 mmol, 2 eq) of triethylamine and the reaction mixture stirred at 25° C. for 1 h. EtOAc (40 mL) and sat. $NaHCO_3$ (20 mL) were added. The organic layer was separated and washed with $H_2O$ (20 mL), brine (20 mL), dried over $Na_2SO_4$, and concentrated to afford the crude 1-{3-[4-(2-chloro-6-methanesulfonylamino-phenyl)-piperazin-1-yl]-propyl}-3-(4-trifluoromethyl-phenyl)-1,4,6,7-tetrahydro-pyrazolo[4,3-c]pyridine-5-carboxylic acid tert-butyl ester. TLC (silica, 10% MeOH/$CH_2Cl_2$): $R_f$=0.3. MS (electrospray): exact mass calculated for $C_{32}H_{40}ClF_3N_6O_4S$, 696.25; m/z found, 697.2 [M+H]$^+$.

I. 1-{3-[4-(2-Chloro-6-methanesulfonylamino-phenyl)-piperazin-1-yl]-propyl}-3-(4-trifluoromethyl-phenyl)-1,4,6,7-tetrahydro-pyrazolo[4,3-c]pyridine-5-tert-butoxycarbonyl-sulfonic acid amide A solution of 97 mg (0.14 mmol) of 1-{3-[4-(2-chloro-6-methanesulfonylamino-phenyl)-piperazin-1-yl]-propyl}-3-(4-trifluoromethyl-phenyl)-1,4,6,7-tetrahydro-pyrazolo[4,3-c]pyridine-5-carboxylic acid tert-butyl ester in 3 mL of $CH_2Cl_2$ was treated with 1.5 mL of trifluoroacetic acid. The reaction mixture was stirred at 25° C. for 1 h before all volatiles were removed. To this crude material in 0.5 mL of CH₂Cl₂ was added dropwise a premixed solution of chlorosulfonyl isocyanate (18 μL, 0.209 mmol) and 2-methyl-2-propanol (20 μL, 0.209 mmol) in CH₂Cl₂ (0.150 mL). The reaction mixture was allowed to stir at 25° C. overnight. Preparative TLC (silica, 2-10% MeOH/CH₂Cl₂) provided the title compound (84 mg, 78%). TLC (silica, 10% MeOH/CH₂Cl₂): $R_f$=0.3. MS (electrospray): exact mass calculated for $C_{32}H_{41}ClF_3N_7O_6S_2$, 775.22; m/z found, 776.2 [M+H]⁺.

J. 1-{3-[4-(2-Chloro-6-methanesulfonylamino-phenyl)-piperazin-1-yl]-propyl}-3-(4-trifluoromethyl-phenyl)-1,4,6,7-tetrahydro-pyrazolo[4,3-c]pyridine-5-sulfonic acid amide 1-{3-[4-(2-Chloro-6-methanesulfonylamino-phenyl)-piperazin-1-yl]-propyl}-3-(4-trifluoromethyl-phenyl)-1,4,6,7-tetrahydro-pyrazolo[4,3-c]pyridine-5-tert-butoxycarbonyl-sulfonic acid amide (84 mg, 0.11 mmol) was dissolved in trifluoroacetic acid (0.75 mL) and CH₂Cl₂ (0.75 mL). The reaction mixture was allowed to stir at 25° C. for 2 h. Removal of volatiles under a stream of nitrogen provided 1-{3-[4-(2-chloro-6-methanesulfonylamino-phenyl)-piperazin-1-yl]-propyl}-3-(4-trifluoromethyl-phenyl)-1,4,6,7-tetrahydro-pyrazolo[4,3-c]pyridine-5-sulfonic acid amide in quantitative yield as a trifluoroacetic acid salt. MS (electrospray): exact mass calculated for $C_{27}H_{33}ClF_3N_7O_4S_2$, 675.17; m/z found, 676.2 [M+H]⁺. ¹H NMR (400 MHz, CDCl₃): 7.73 and 7.63 (AB pattern, J=8.2 Hz, 4H), 7.37 (d, J=7.8 Hz, 1H), 7.13 (t, J=7.8 Hz, 1H), 7.04 (d, J=7.8 Hz, 1H), 4.32 (s, 2H), 4.20 (t, J=6.3 Hz, 2H), 3.87-3.80 (m, 2H), 3.80-3.75 (m, 4H), 3.70-3.25 (m, 7H), 3.00-2.75 (m, 4H), 2.25-2.15 (m, 2H).

Example 19

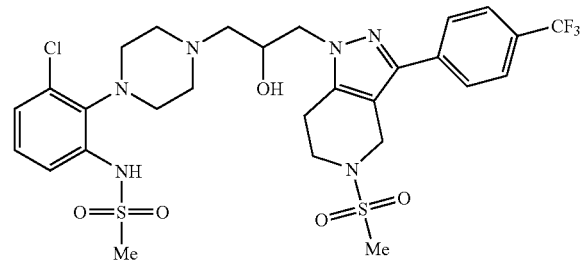

N-[3-Chloro-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-methanesulfonamide A. 5-Methanesulfonyl-1-oxiranylmethyl-3-(4-trifluoromethyl-phenyl)-4,5,6,7-tetrahydro-1H-pyrazolo[4,3-c]pyridine 5-Methanesulfonyl-3-(4-trifluoromethyl-phenyl)-4,5,6,7-tetrahydro-1H-pyrazolo[4,3-c]pyridine (10.0 g, 29.0 mmol) and epichlorohydrin (24 mL, 307 mmol) were set stirring in DMF (150 mL) containing Cs₂CO₃ (10.4 g, 31.9 mmol). After stirring at room temperature for 4 days the mixture was evaporated, brought up in EtOAc and washed with water. The organics were dried (MgSO₄) and evaporated to give a light yellow solid. Column chromatography (silica, 5% acetone/CH₂Cl₂) gave 4.1 g (35%) of a white solid. TLC (silica, 5% acetone/CH₂Cl₂): $R_f$=0.28. MS (electrospray): exact mass calculated for $C_{17}H_{18}F_3N_3O_3S$, 401.10; m/z found, 402.1 [M+H]⁺. ¹H NMR (400 MHz, CDCl₃): 7.84 (d, J=8.3 Hz, 2H), 7.79 (d, J=8.3 Hz, 2H), 4.70-4.62 (m, 3H), 4.25 (d, J=5.4 Hz, 1H), 3.90-3.70 (m, 2H), 3.47 (m, 1H), 3.10-2.9 (m, 6H), 2.65-2.60 (m, 1H).

B. 4-(2-Chloro-6-nitro-phenyl)-piperazine-1-carboxylic acid tert-butyl ester

To a stirred solution of 0.96 g (5.0 mmol) of 1,2-dichloro-3-nitrobenzene and 0.93 g (5.0 mmol, 1 eq) of 1-tert-butyloxycarbonylpiperazine in acetonitrile (5 mL) was added 1.38 g (10 mmol, 2 eq) of K₂CO₃. The mixture was heated to reflux for 48 h. The solvent was removed under reduced pressure. The crude product was partitioned between EtOAc (100 mL) and 20 mL of H₂O. The organic layer was washed with H₂O (2×20 mL), dried over Na₂SO₄ and concentrated. Column chromatography (silica, 10-20% EtOAc/hexanes) provided 1.2 g (70%) of 4-(2-chloro-6-nitro-phenyl)-piperazine-1-carboxylic acid tert-butyl ester. TLC (silica, 20% EtOAc/hexanes): $R_f$=0.45. ¹H NMR (400 MHz, CDCl₃): 7.56 (dd, J=8.2, 1.4 Hz, 1H), 7.50 (dd, J=8.2, 1.4 Hz, 1H), 7.13 (t, J=8.2 Hz, 1H), 3.56-3.38 (m, 4H), 3.10-3.00 (m, 4H), 1.48 (s, 9H).

C. 4-(2-Amino-6-chloro-phenyl)-piperazine-1-carboxylic acid tert-butyl ester

A solution of 342 mg (1 mmol) of 4-(2-chloro-6-nitro-phenyl)-piperazine-1-carboxylic acid tert-butyl ester in 5.0 mL of MeOH was treated with 630 mg (10 mmol, 10 eq) of ammonium formate and a catalytic amount of 10% Pd—C (34 mg). The reaction mixture was stirred at 65° C. for 30 min. The reaction mixture was then filtered through a pad of celite and concentrated to obtain a yellow solid. TLC (silica, 5% acetone/CH₂Cl₂): $R_f$=0.40. MS (electrospray): exact mass calculated for $C_{15}H_{22}ClN_3O_2$, 311.14; m/z found, 312.1 [M+H]⁺.

D. 4-(2-Chloro-6-methanesulfonylamino-phenyl)-piperazine-1-carboxylic acid tert-butyl ester 4-(2-Amino-6-chloro-phenyl)-piperazine-1-carboxylic acid tert-butyl ester (163 mg, 0.53 mmol) in CH₂Cl₂ was treated with 62 μL (0.80 mmol, 1.5 eq) of methanesulfonyl chloride and 148 μL (1.06 mmol, 2 eq) of triethylamine and the reaction mixture stirred at 25° C. for 1 h. EtOAc (40 mL) and sat. NaHCO₃ (20 mL) were added. The organic layer was separated and washed with H₂O (20 mL), brine (20 mL), dried over Na₂SO₄, and concentrated. Column chromatography (silica, 0-5% acetone/CH₂Cl₂) provided 145 mg (70%) of 4-(2-chloro-6-methanesulfonylamino-phenyl)-piperazine-1-carboxylic acid tert-butyl ester. TLC (silica, 5% acetone/CH₂Cl₂): $R_f$=0.35. MS (electrospray): exact mass calculated for $C_{16}H_{24}ClN_3O_4S$, 389.12; m/z found, 388.1 (negative). ¹H NMR (400 MHz, CDCl₃): 7.41 (dd, J=8.2, 1.6 Hz, 1H), 7.11 (t, J=8.2 Hz, 1H), 6.99 (dd, J=8.2, 1.6 Hz, 1H), 4.25-3.91 (m, 2H), 3.66-3.52 (m, 2H), 3.01 (s, 3H), 3.01-2.84 (m, 2H), 2.70-2.56 (m, 2H), 2.55-2.43 (m, 2H), 1.44 (s, 9H).

E. N-[3-Chloro-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-methanesulfonamide 4-(2-Chloro-6-methanesulfonylamino-phenyl)-piperazine-1-carboxylic acid tert-butyl ester (145 mg, 0.37 mmol)

was dissolved in 3 mL of $CH_2Cl_2$ and treated with 1.5 mL of trifluoroacetic acid. The reaction mixture was stirred at 25° C. for 1 h before all volatiles were removed. The solid was treated with $CH_2Cl_2$ (20 mL) and aqueous KOH (4 N, 10 mL). The organic layer was separated, dried over $Na_2SO_4$, and concentrated. The crude oil (90 mg) was dissolved in absolute EtOH (1.0 mL) and treated with 96 mg (0.24 mmol) of 5-methanesulfonyl-1-oxiranylmethyl-3-(4-trifluoromethyl-phenyl)-4,5,6,7-tetrahydro-1H-pyrazolo[4,3-c]pyridine. The reaction mixture was refluxed at 85° C. for 3 h and then the solvent was removed. Column chromatography (silica, 0-5% MeOH/$CH_2Cl_2$) provided 138 mg (20% over 4 steps) of N-[3-chloro-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-methanesulfonamide. TLC (silica, 5% MeOH/$CH_2Cl_2$): $R_f$=0.45. MS (electrospray): exact mass calculated for $C_{28}H_{34}ClF_3N_6O_5S_2$, 690.17; m/z found, 691.2 [M+H]$^+$. $^1$H NMR (400 MHz, $CDCl_3$): 8.28 (s, 1H), 7.65 and 7.59 (AB pattern, J=8.4 Hz, 4H), 7.36 (d, J=8.1 Hz, 1H), 7.07 (t, J=8.2 Hz, 1H), 6.95 (d, J=8.2 Hz, 1H), 4.54-4.44 (m, 2H), 4.21-3.94 (m, 3H), 3.77-3.52 (m, 4H), 3.41 (m, 2H), 2.96 (s, 3H), 2.81 (s, 3H), 3.05-2.73 (m, 4H), 2.66-2.20 (m, 4H).

Example 20

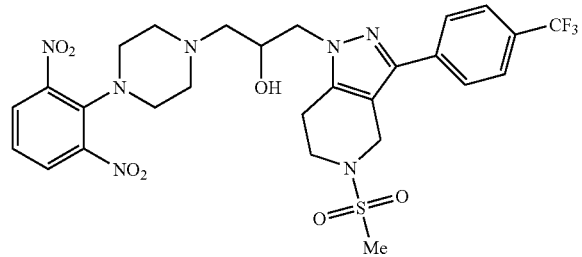

1-[4-(2,6-Dinitro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol A. 4-(2,6-Dinitro-phenyl)-piperazine-1-carboxylic acid tert-butyl ester To a stirred solution of 1.01 g (5.0 mmol) of 1-chloro-2,6-dinitrobenzene and 0.93 g (5.0 mmol) of 1-tert-butyloxycarbonylpiperazine in acetonitrile (5 mL) was added 1.38 g (10 mmol) of $K_2CO_3$. The mixture was heated to reflux for 48 h. The solvent was removed under reduced pressure. The crude product was partitioned between EtOAc (100 mL) and 20 mL of $H_2O$. The organic layer was washed with $H_2O$ (2×20 mL), dried over $Na_2SO_4$ and concentrated. Column chromatography (silica, 10-20% EtOAc/hexanes) provided 1.31 g (85%) of 4-(2,6-dinitro-phenyl)-piperazine-1-carboxylic acid tert-butyl ester TLC (silica, 20% EtOAc/hexanes): $R_f$=0.35. $^1$H NMR (400 MHz, $CDCl_3$): 7.75 (d, J=8.2 Hz, 2H), 7.25 (t, J=8.2 Hz, 1H), 3.30 (m, 4H), 2.95 (m, 2H), 1.44 (s, 9H).

B. 1-[4-(2,6-Dinitro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol 4-(2,6-Dinitro-phenyl)-piperazine-1-carboxylic acid tert-butyl ester (220 mg, 0.63 mmol) was dissolved in 5.0 mL of $CH_2Cl_2$ and treated with 3.0 mL of trifluoroacetic acid. The reaction mixture was stirred at 25° C. for 1 h before all volatiles were removed. The solid was treated with $CH_2Cl_2$ (20 mL) and aqueous KOH (4 N, 10 mL). The organic layer was separated, dried over $Na_2SO_4$, and concentrated. The crude oil (67 mg) was dissolved in absolute EtOH (1.2 mL) and treated with 141 mg (0.35 mmol, 1.3 eq) of 5-methanesulfonyl-1-oxiranylmethyl-3-(4-trifluoromethyl-phenyl)-4,5,6,7-tetrahydro-1H-pyrazolo[4,3-c]pyridine. The reaction mixture was refluxed at 85° C. for 3 h and then the solvent was removed. Column chromatography purification (silica, 10-20% acetone/$CH_2Cl_2$) provided 150 mg (85%) of 1-[4-(2,6-dinitro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol. TLC (silica, 10% acetone/$CH_2Cl_2$): $R_f$=0.3. MS (electrospray): exact mass calculated for $C_{27}H_{30}F_3N_7O_7S$, 653.19; m/z found, 654.2 [M+H]$^+$. $^1$H NMR (400 MHz, $CDCl_3$): 7.71 (d, J=8.2 Hz, 2H), 7.64 and 7.58 (AB pattern, J=8.4 Hz, 4H), 7.20 (t, J=8.2 Hz, 1H), 4.54 (s, 2H), 4.29-4.12 (m, 2H), 3.66 (t, J=5.3 Hz, 2H), 3.70-2.95 (m, 9H), 2.91 (s, 3H), 2.67-2.32 (m, 4H).

Example 21

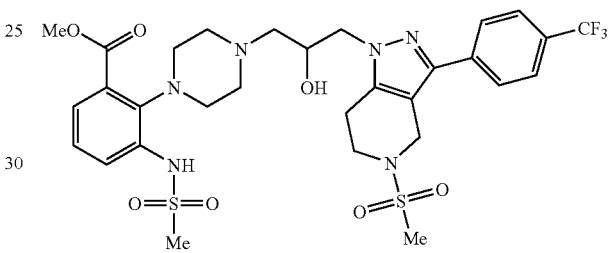

2-(4-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-3-methanesulfonylamino-benzoic acid methyl ester A. 4-(2-Methoxycarbonyl-6-nitro-phenyl)-piperazine-1-carboxylic acid tert-butyl ester To a stirred solution of 736 mg (2.83 mmol) of ethyl 2-bromo-3-nitrobenzoate and 579 mg (3.1 mmol, 1.1 eq) of 1-tert-butyloxycarbonylpiperazine in n-butanol (6 mL) was added 330 mg (3.1 mmol, 1.1 eq) of $Na_2CO_3$. The mixture was heated to reflux for 4 h. The solvent was removed under reduced pressure. The crude product was partitioned between EtOAc (100 mL) and 20 mL of $H_2O$. The organic layer was washed with $H_2O$ (2×20 mL), dried over $Na_2SO_4$ and concentrated. Column chromatography (silica, 10-20% EtOAc/hexanes) provided 744 mg (72%) of 4-(2-methoxycarbonyl-6-nitro-phenyl)-piperazine-1-carboxylic acid tert-butyl ester. TLC (silica, 20% EtOAc/hexanes): $R_f$=0.5. $^1$H NMR (400 MHz, $CDCl_3$): 7.67 (dd, J=8.2, 1.4 Hz, 1H), 7.62 (dd, J=8.2, 1.4 Hz, 1H), 7.16 (t, J=8.2 Hz, 1H), 3.86 (s, 3H), 3.44-3.36 (m, 4H), 3.03-2.95 (m, 4H), 1.48 (s, 9H).

B. 2-(4-{2-Hydroxy-3-[5-methanesulfonyl-3-(4-trifluoromethyl-Phenyl)-4,5,6,7-tetrahydro-pyrazolo[4,3-c]pyridin-1-yl]-propyl}-piperazin-1-yl)-3-methanesulfonylamino-benzoic acid methyl ester A solution of 1.0 g (2.73 mmol) of 4-(2-methoxycarbonyl-6-nitro-phenyl)-piperazine-1-carboxylic acid tert-butyl ester in 18 mL of MeOH was treated with 893 mg (13.7 mmol, 5 eq)

of zinc dust and glacial acetic acid (8 mL). The reaction mixture was stirred at 25° C. for 1 h. The reaction mixture was then filtered through a pad of celite and concentrated to obtain a thick oil. The residue was taken up in EtOAc (200 mL) and sat. NaHCO$_3$ (100 mL). The organic layer was separated, washed with H$_2$O (2×50 mL), dried over Na$_2$SO$_4$, and concentrated. Column chromatography (silica, 10-30% EtOAc/hexanes) provided the desired amine (844 mg, 92%). The amine (42 mg, 0.13 mmol) in CH$_2$Cl$_2$ (0.5 mL) was treated with 9.7 µL (0.13 mmol, 1.0 eq) of methanesulfonyl chloride and 34.9 µL (0.25 mmol, 2 eq) of triethylamine and the reaction mixture stirred at 25° C. for 1 h. EtOAc (20 mL) and sat. NaHCO$_3$ (10 mL) were added. The organic layer was separated and washed with H$_2$O (10 mL), brine (20 mL), dried over Na$_2$SO$_4$, and concentrated. The crude oil was dissolved in 2 mL of CH$_2$Cl$_2$ and treated with 0.5 mL of trifluoroacetic acid. The reaction mixture was stirred at 25° C. for 1 h before all volatiles were removed. The crude oil was dissolved in absolute EtOH (1.0 mL) and treated with 40 mg (0.1 mmol) of 5-methanesulfonyl-1-oxiranylmethyl-3-(4-trifluoromethyl-phenyl)-4,5,6,7-tetrahydro-1H-pyrazolo[4,3-c]pyridine and 200 µL of triethylamine. The reaction mixture was refluxed at 85° C. for 4 h and then the solvent was removed. Preparative TLC (silica, 7% MeOH/CH$_2$Cl$_2$) provided 35 mg (49% over 3 steps) of the title compound. TLC (silica, 5% MeOH/CH$_2$Cl$_2$): R$_f$=0.30. MS (electrospray): exact mass calculated for C$_{30}$H$_{37}$F$_3$N$_6$O$_7$S$_2$, 714.21; m/z found, 715.2 [M+H]$^+$. $^1$H NMR (400 MHz, CDCl$_3$): 8.11 (s, 1H), 7.74-7.59 (m, 5H), 7.30 (d, J=8.1 Hz, 1H), 7.21 (t, J=8.2 Hz, 1H), 4.62-4.49 (m, 2H), 4.25-3.99 (m, 3H), 3.90 (s, 3H), 3.80-3.57 (m, 3H), 3.53-3.27 (m, 2H), 3.14-2.78 (m, 4H), 3.05 (s, 3H), 2.86 (s, 3H), 2.76-2.65 (m, 2H), 2.61-2.20 (m, 4H).

Example 22

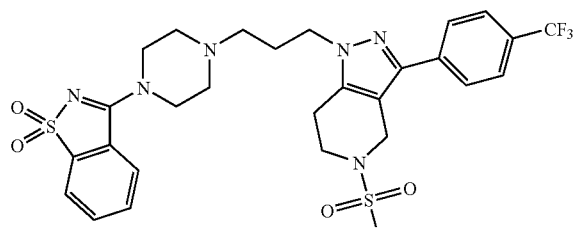

1-{3-[4-(1,1-Dioxo-1H-1λ$^6$-benzo[d]isothiazol-3-yl)-piperazin-1-yl]-propyl}-5-methanesulfonyl-3-(4-trifluoromethyl-phenyl)-4,5,6,7-tetrahydro-1H-pyrazolo[4,3-c]pyridine A. 3-piperazin-1-yl-benzo[d]isothiazole 1,1-dioxide POCl$_3$ (10.2 mL, 109.2 mmol) was added to saccharin (5.0 g, 27.3 mmol) and heated at 120° C. for 20 h. The excess reagent was removed in a rotary evaporator and water (50 mL) was added to the residue to form a precipitate. The solid was filtered, washed with water (2×20 mL), and dried. A portion of the above crude material (2.0 g, 9.95 mmol) and piperazine (4.28 g, 49.75 mmol) was taken in dioxane (10 mL), and heated at 100° C. for 24 h. The reaction was allowed to cool to room temperature and poured into ice water (50 g), and neutralized by addition of 10% aqueous NaOH. The mixture was extracted with CH$_2$Cl$_2$ (3×25 mL) and the combined organic extracts were washed with brine, dried (Na$_2$SO$_4$) and concentrated. MPLC (silica, 5-20% MeOH/CH$_2$Cl$_2$) afforded the piperazinyl derivative (0.07 g, 4.2%). MS (electrospray): exact mass calculated for C$_{11}$H$_{13}$N$_3$O$_2$S, 251.07; m/z found, 252.1 [M+H]$^+$. $^1$H NMR (400 MHz, CDCl$_3$): 7.72 (dd, J=0.8, 7.4 Hz, 1H), 7.64 (d, J=7.8 Hz, 1H), 7.49 (dt, J=0.8, 7.4 Hz, 1H), 7.43 (dt, J=1.2, 7.8 Hz, 1H), 3.80 (s, 4H), 2.85 (br t, J=5.0 Hz, 4H), 2.07 (br s, 1H). $^{13}$C NMR (100 MHz, CDCl$_3$): 160.8, 145.3, 133.3, 133.0, 128.5, 125.9, 123.2, 49.8, 46.3.

B. 1-{3-[4-(1,1-Dioxo-1H-1λ$^6$-benzo[d]isothiazol-3-yl)-piperazin-1-yl]-propyl}-5-methanesulfonyl-3-(4-trifluoromethyl-phenyl)-4,5,6,7-tetrahydro-1H-pyrazolo[4,3-c]pyridine To a stirred solution of 3-[5-methanesulfonyl-3-(4-trifluoromethyl-phenyl)-4,5,6,7-tetrahydro-pyrazolo[4,3-c]pyridin-1-yl]-propionaldehyde (0.040 g, 0.13 mmol) and 3-piperazin-1-yl-benzo[d]isothiazole 1,1-dioxide (0.050 g, 0.21 mmol) in CH$_2$Cl$_2$ (0.5 mL), glacial AcOH (12 µL, 0.21 mmol) was added and stirred for 15 min at room temperature. NaBH(OAc)$_3$ (0.058 g, 0.27 mmol) was added and stirred under nitrogen overnight. Saturated NaHCO$_3$ (0.5 mL) was then added and stirred for 15 min. The layers separated and the aqueous layer was extracted with CH$_2$Cl$_2$ (0.5 mL). MPLC (silica, 2-15% MeOH/CH$_2$Cl$_2$) afforded the desired product as a white solid (0.048 g, 76%). TLC (silica, 12% MeOH/CH$_2$Cl$_2$): R$_f$=0.50. MS (electrospray): exact mass calculated for C$_{28}$H$_{31}$F$_3$N$_6$O$_4$S$_2$, 636.18; m/z found, 637.2 [M+H]$^+$. $^1$H NMR (400 MHz, CDCl$_3$): 7.94 (dd, J=0.8, 7.6 Hz, 1H), 7.86 (d, J=7.8 Hz, 1H), 7.75 (d, J=8.3 Hz, 2H), 7.73-7.63 (m, 2H), 7.68 (d, J=8.3 Hz, 2H), 4.57 (s, 2H), 4.17 (t, J=6.9 Hz, 2H), 4.04 (br s, 4H), 3.69 (t, J=5.7 Hz, 2H), 2.94 (s, 3H), 2.92 (t, J=6.2 Hz, 2H), 2.62 (t, J=5.0 Hz, 4H), 2.44 (t, J=6.6 Hz, 2H), 2.13 (q, J=6.6 Hz, 2H).

Example 23

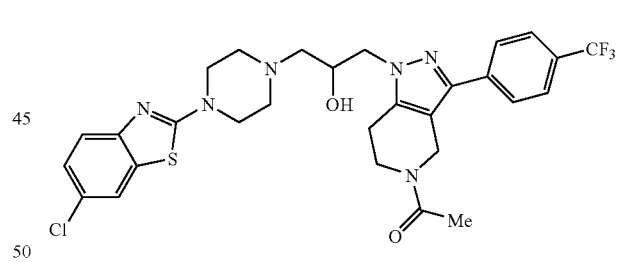

1-[1-{3-[4-(6-Chloro-benzothiazol-2-yl)-piperazin-1-yl]-2-hydroxy-propyl}-3-(4-trifluoromethyl-phenyl)-1,4,6,7-tetrahydro-pyrazolo[4,3-c]pyridin-5-yl]-ethanone A. 6-Chloro-2-piperazin-1-yl-benzothiazole To a stirred solution of 1.07 g (5.24 mmol) of 2,6-dichlorobenzothiazole in dry DMF (25 mL) was added 2.4 g of potassium carbonate (15.7 mmol) and 0.5 g of piperazine (5.8 mmol). The mixture was stirred at room temperature for 4 h. When the reaction was complete it was partitioned between EtOAc (150 mL) and water (50 mL) and separated. The aqueous layer was extracted with EtOAC (2×100 mL). The combined organic layers were then washed with water (2×25 mL), brine, dried over Na$_2$SO$_4$, and the solvent was removed under reduced pressure to give 1.33 g (100%) of desired product as a white solid. MS (electrospray): exact mass calculated for C$_{11}$H$_{12}$ClN$_3$S, 253.04; m/z found, 254.0 [M+H]$^+$.

B. 1-[1-{3-[4-(6-Chloro-benzothiazol-2-yl)-piperazin-1-yl]-2-hydroxy-propyl}-3-(4-trifluoromethyl-Phenyl)-1,4,6,7-tetrahydro-pyrazolo[4,3-c]pyridin-5-yl]-ethanone To a stirred solution of 144 mg (0.39 mmol) of 1-[1-oxiranylmethyl-3-(4-trifluoromethyl-phenyl)-1,4,6,7-tetrahydro-pyrazolo[4,3-c]pyridin-5-yl]-ethanone in 4 mL of EtOH was added 100 mg (0.39 mmol) 6-chloro-2-piperazin-1-yl-benzothiazole. The solution was heated to 60° C. overnight. The solvent was then removed by rotary evaporation and the crude product was purified by column chromatography (silica, 0-10% MeOH/EtOAc) to afford 220 mg (90%) of a white solid. MS (electrospray): exact mass calculated for C$_{29}$H$_{30}$ClF$_3$N$_6$O$_2$S: 618.18; m/z found, 619.2 [M+H]$^+$. HPLC (reverse phase conditions 40-90%): t$_R$=8.27 min. $^1$H NMR (CDCl$_3$, 400 MHz, a mixture of amide rotamers): 7.70 (d, J=8.34 Hz, 1H), 7.62 (m, 2H), 7.57 (d, J=8.59 Hz, 1H), 7.48 (d, J=2.53 Hz, 1H), 7.36 (d, J=8.59 Hz, 1H), 7.16 (dd, J=8.59, 2.53 Hz, 1H), 4.80 and 4.68 (A and B of AB quartet, J=15.92 Hz, 1H), 4.58 (s, 1H), 4.18-4.08 (m, 2H), 4.01-3.89 (m, 2H), 3.85-3.60 (m, 2H), 3.59-3.47 (m, 4H), 2.94-2.75 (m, 2H), 2.72-2.62 (m, 2H), 2.55-2.47 (m, 2H), 2.46-2.39 (m, 2H), 2.13 (s, 1.5H), 2.08 (s, 1.5H).

Example 24

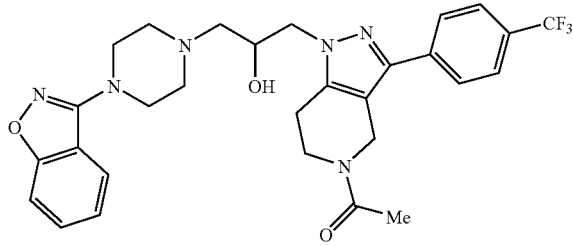

1-[1-[3-(4-Benzo[d]isoxazol-3-yl-piperazin-1-yl)-2-hydroxy-propyl]-3-(4-trifluoromethyl-phenyl)-1,4,6,7-tetrahydro-pyrazolo[4,3-c]pyridin-5-yl]-ethanone

A. 4-Benzo[d]isoxazol-3-yl-piperazine-1-carboxylic acid tert-butyl ester

To a stirred solution of 100 mg (0.65 mmol) of 3-chloro-1,2-benzisoxazole in pyridine (1 mL) was added 145 mg of piperazine-1-carboxylic acid tert-butyl ester (0.78 mmol) and 0.18 mL of DBU (0.78 mmol). The mixture was stirred at 100° C. overnight and then partitioned between EtOAC (50 mL) and water (20 mL) and separated. The aqueous layer was extracted with EtOAC (2×30 mL). The combined organic layers were then washed with water (25 mL), brine, dried over Na$_2$SO$_4$, and the solvent was removed under reduced pressure to give crude product. Purification by column chromatography (silica, 60-100% CH$_2$Cl$_2$/hexanes) gave 82 mg (42%) of the desired product as a light yellow solid. MS (electrospray): exact mass calculated for C$_{16}$H$_{21}$N$_3$O$_3$, 303.16; m/z found, 326.1 [M+Na]$^+$. $^1$H NMR (CDCl$_3$, 400 MHz): 7.68 (dt, J=8.02, 0.98 Hz, 1H), 7.52-7.44 (m, 2H), 7.24 (ddd, J=8.42, 6.46, 1.57 Hz, 1H), 3.66-3.61 (m, 4H), 3.56-3.49 (m, 4H), 1.49 (s, 9H).

B. 1-[1-[3-(4-Benzo[d]isoxazol-3-yl-piperazin-1-yl)-2-hydroxy-Propyl]-3-(4-trifluoromethyl-phenyl)-1,4,6,7-tetrahydro-pyrazolo[4,3-c]pyridin-5-yl]-ethanone A solution of 82 mg (0.27 mmol) of 4-benzo[d]isoxazol-3-yl-piperazine-1-carboxylic acid tert-butyl ester in 2 mL of CH$_2$Cl$_2$ was treated with trifluoroacetic acid (0.5 mL) at room temperature overnight. The solvent was then removed and the crude product dissolved in EtOH and stirred over 100 mg of sodium bicarbonate for 1 h, the solid was then filtered off and the filtrate concentrated. The crude piperazine was then dissolved in 4 mL EtOH and treated with 100 mg (0.27 mmol) of 1-[1-oxiranylmethyl-3-(4-trifluoromethyl-phenyl)-1,4,6,7-tetrahydro-pyrazolo[4,3-c]pyridin-5-yl]-ethanone. The solution was heated to 60° C. overnight. The solvent was then removed by rotary evaporation and the crude product was purified by column chromatography (silica, 0-10% MeOH/EtOAc) to afford 105 mg (68%) of a white solid. MS (electrospray), exact mass calculated for C$_{29}$H$_{31}$F$_3$N$_6$O$_3$, 568.24; m/z found, 569.2 [M+H]$^+$. $^1$H NMR (CDCl$_3$, 400 MHz, a mixture of amide rotamers): 7.77 (d, J=8.41 Hz, 1H), 7.69 (m, 2H), 7.67-7.62 (m, 2H), 7.50-7.44 (m, 1H), 7.45-7.42 (m, 1H), 7.23-7.18 (m, 1H), 4.93 (br m, 1H), 4.87 and 4.75 (A and B of AB quartet, J=15.65 Hz, 1H), 4.65 (br s, 1H), 4.27-4.15 (m, 2.3H), 4.09-3.95 (m, 1.7H), 3.91-3.82 (m, 0.7H), 3.81-3.66 (m, 1.3H), 3.62-3.49 (m, 4H), 3.01-2.85 (m, 1.5H), 2.85-2.74 (m, 2.5H), 2.71-2.60 (m, 2H), 2.58-2.45 (m, 2H), 2.20 (s, 1.5H), 2.15 (s, 1.5H).

Example 25

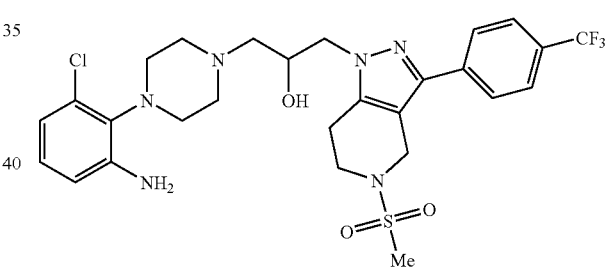

1-[4-(2-Amino-6-chloro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol

Example 26

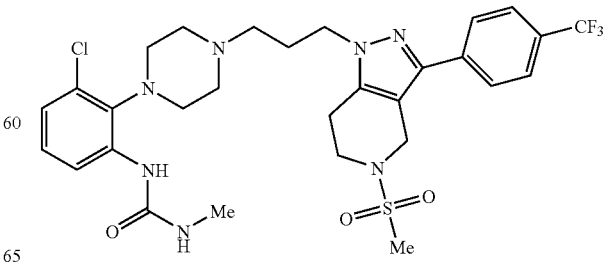

1-[3-Chloro-2-(4-{3-[5-methanesulfonyl-3-(4-trif-
luoromethyl-phenyl)-4,5,6,7-tetrahydro-pyrazolo[4,
3-c]pyridin-1-yl]-propyl}-piperazin-1-yl)-phenyl]-3-
methyl-urea Example 27

3-Chloro-2-(4-{3-[5-methanesulfonyl-3-(4-trifluo-
romethyl-phenyl)-4,5,6,7-tetrahydro-pyrazolo[4,3-c]
pyridin-1-yl]-propyl}-piperazin-1-yl)-phenylamine Example 30

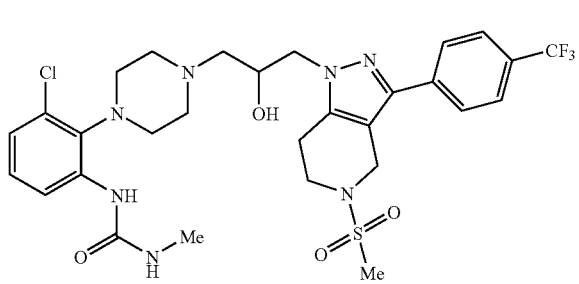

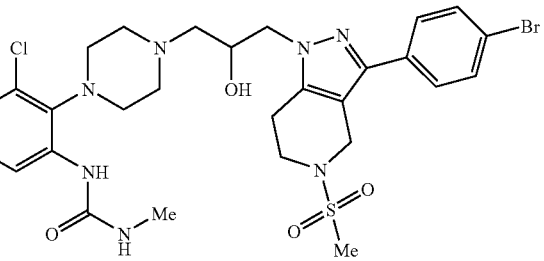

1-[3-Chloro-2-(4-{2-hydroxy-3-[5-methanesulfonyl-
3-(4-trifluoromethyl-phenyl)-4,5,6,7-tetrahydro-
pyrazolo[4,3-c]pyridin-1-yl]-propyl}-piperazin-1-
yl)-phenyl]-3-methyl-urea Example 28

1-[2-(4-{3-[3-(4-Bromo-phenyl)-5-methanesulfonyl-
4,5,6,7-tetrahydro-pyrazolo[4,3-c]pyridin-1-yl]-2-
hydroxy-propyl}-piperazin-1-yl)-3-chloro-phenyl]-3-
methyl-urea Example 31

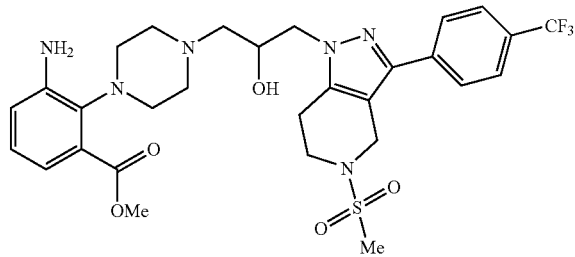

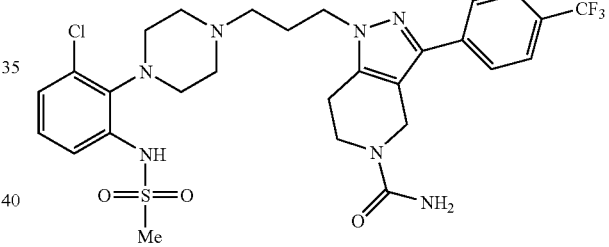

3-Amino-2-(4-{2-hydroxy-3-[5-methanesulfonyl-3-
(4-trifluoromethyl-phenyl)-4,5,6,7-tetrahydro-pyra-
zolo[4,3-c]pyridin-1-yl]-propyl}-piperazin-1-yl)-
benzoic acid methyl ester Example 29

1-{3-[4-(2-Chloro-6-methanesulfonylamino-phenyl)-
piperazin-1-yl]-propyl}-3-(4-trifluoromethyl-phe-
nyl)-1,4,6,7-tetrahydro-pyrazolo[4,3-c]pyridine-5-
carboxylic acid amide Example 32

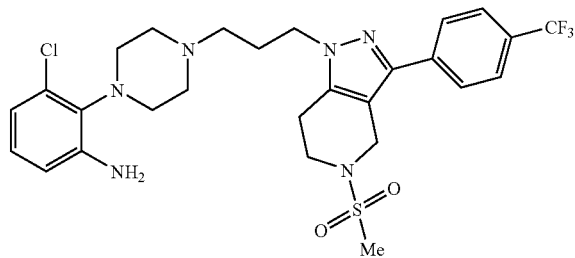

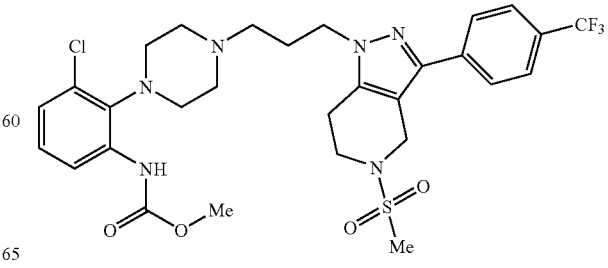

[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-carbamic acid methyl ester Example 33

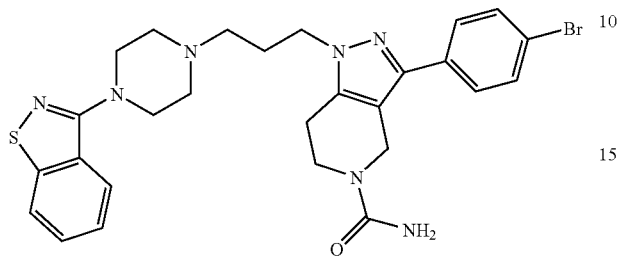

1-[3-(4-Benzo[d] isothiazol-3-yl-piperazin-1-yl)-propyl]-3-(4-bromo-phenyl)-1,4,6,7-tetrahydro-pyrazolo[4,3-c]pyridine-5-carboxylic acid amide Example 34

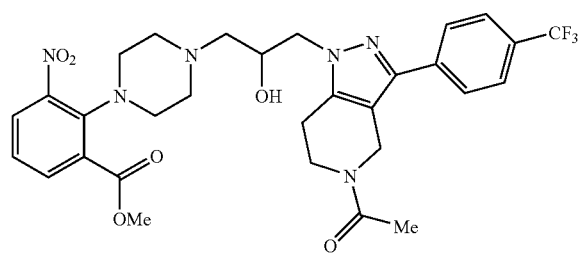

2-(4-{3-[5-Acetyl-3-(4-trifluoromethyl-phenyl)-4,5,6,7-tetrahydro-pyrazolo[4,3-c]pyridin-1-yl]-2-hydroxy-propyl}-piperazin-1-yl)-3-nitro-benzoic acid methyl ester Example 35

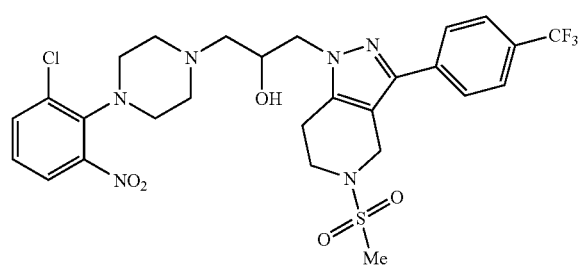

1-[4-(2-Chloro-6-nitro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol Example 36

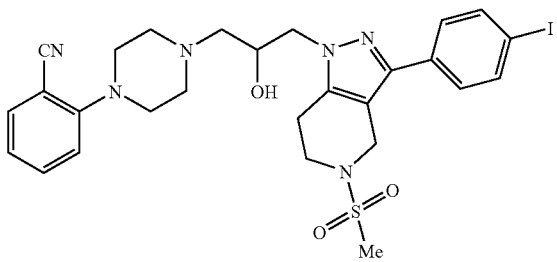

2-(4-{2-Hydroxy-3-[3-(4-iodo-phenyl)-5-methanesulfonyl-4,5,6,7-tetrahydro-pyrazolo[4,3-c]pyridin-1-yl]-propyl}-piperazin-1-yl)-benzonitrile Example 37

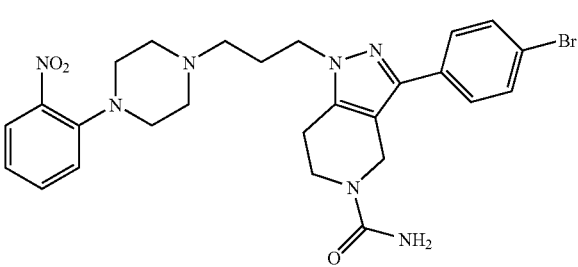

3-(4-Bromo-phenyl)-1-{3-[4-(2-nitro-phenyl)-piperazin-1-yl]-propyl}-1,4,6,7-tetrahydro-pyrazolo[4,3-c]pyridine-5-carboxylic acid amide Example 38

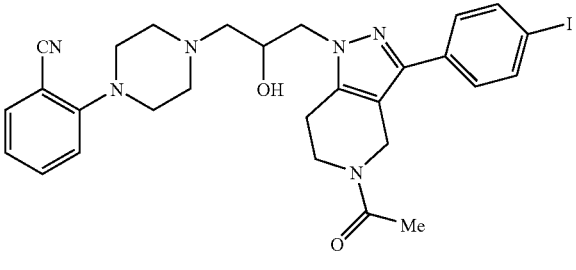

67

2-(4-{3-[5-Acetyl-3-(4-iodo-phenyl)-4,5,6,7-tetrahydro-pyrazolo[4,3-c]pyridin-1-yl]-2-hydroxy-propyl}-piperazin-1-yl)-benzonitrile Example 39

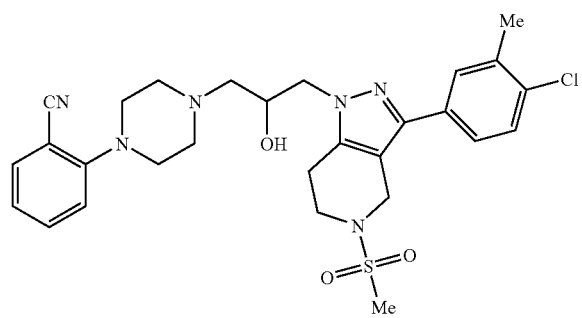

2-(4-{3-[3-(4-Chloro-3-methyl-phenyl)-5-methanesulfonyl-4,5,6,7-tetrahydro-pyrazolo[4,3-c]pyridin-1-yl]-2-hydroxy-propyl}-piperazin-1-yl)-benzonitrile Example 40

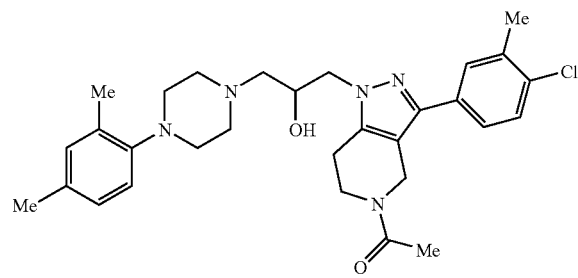

1-(3-(4-Chloro-3-methyl-phenyl)-1-{3-[4-(2,4-dimethyl-phenyl)-piperazin-1-yl]-2-hydroxy-propyl}-1,4,6,7-tetrahydro-pyrazolo[4,3-c]pyridin-5-yl)-ethanone Example 41

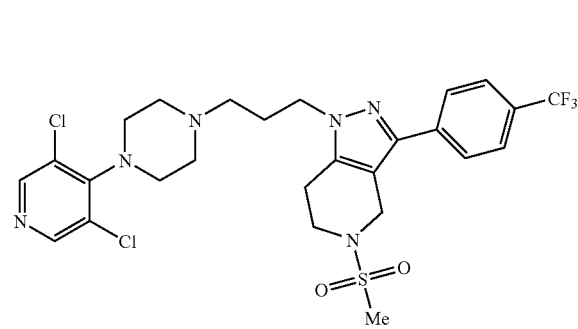

68

1-{3-[4-(3,5-Dichloro-pyridin-4-yl)-piperazin-1-yl]-propyl}-5-methanesulfonyl-3-(4-trifluoromethyl-phenyl)-4,5,6,7-tetrahydro-1H-pyrazolo[4,3-c]pyridine Example 42

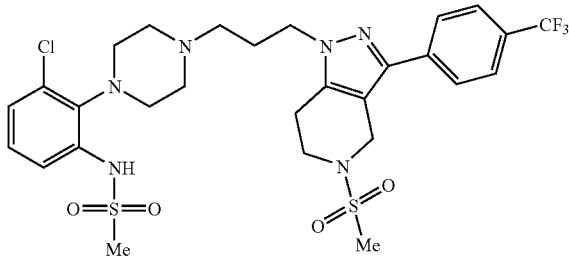

2-(4-{3-[5-Methanesulfonyl-3-(4-trifluoromethyl-phenyl)-4,5,6,7-tetrahydro-pyrazolo[4,3-c]pyridin-1-yl]-propyl}-piperazin-1-yl)-benzonitrile Example 43

N-[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-methanesulfonamide Example 44

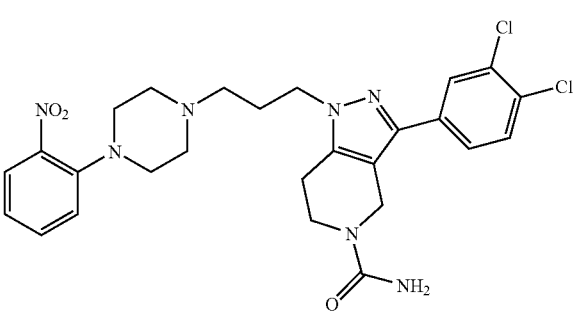

3-(3,4-Dichloro-phenyl)-1-{3-[4-(2-nitro-phenyl)-piperazin-1-yl]-propyl}-1,4,6,7-tetrahydro-pyrazolo[4,3-c]pyridine-5-carboxylic acid amide Example 45

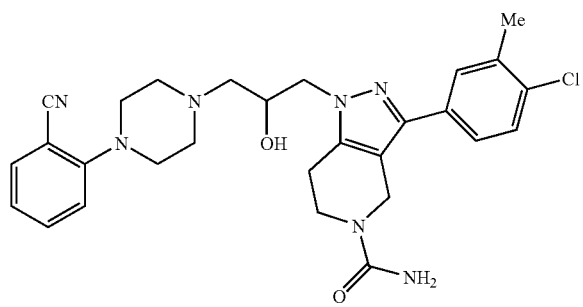

3-(4-Chloro-3-methyl-phenyl)-1-{3-[4-(2-cyano-phenyl)-piperazin-1-yl]-2-hydroxy-propyl}-1,4,6,7-tetrahydro-pyrazolo[4,3-c]pyridine-5-carboxylic acid amide Example 46

Cathepsin S Inhibition Assay.

Recombinant human cathepsin S (CatS) was expressed in the baculovirus system and purified in one step with a thiopropyl-sepharose column. 10-L yielded ~700 mg of CatS and N-terminal sequencing confirmed identity. The assay is run in 100 mM sodium acetate pH 5.0 containing 1 mM DTT and 100 mM NaCl. The substrate for the assay is
(Aedens)EKARVLAEAA(Dabcyl)K-amide The $K_m$ for the substrate is around 5 μM but the presence of substrate inhibition makes kinetic analysis difficult. With 20 μM substrate the assay rate is linear over the range of 1-8 ng CatS in 100 μl reaction. Using 2 ng/well of CatS, the production of product is linear and yields ~7-fold signal after 20 min with only 20% loss of substrate. Primary assays are run by quenching the reaction after 20 min with 0.1% SDS and then measuring the fluorescence. For other assays, measurements are taken every min for 20 min. The rate is calculated from the slope of the increase and the percent inhibition is calculated from this (See Tables 1, 2 and 3 below).

TABLE 1

| EXAMPLE | IC$_{50}$ (μM) |
| --- | --- |
| 1 | 0.89 |
| 2 | 1.22 |
| 3 | 0.84 |
| 4 | 0.51 |
| 5 | 0.36 |
| 6 | 0.30 |
| 7 | 6.60 |
| 8 | 0.89 |
| 9 | 1.14 |
| 10 | 0.05 |
| 11 | 0.03 |
| 12 | 0.98 |
| 13 | 0.77 |
| 14 | 0.25 |
| 15 | 0.12 |
| 16 | 0.06 |

TABLE 1-continued

| EXAMPLE | IC$_{50}$ (μM) |
| --- | --- |
| 17 | 0.08 |
| 18 | 0.14 |
| 19 | 0.06 |
| 20 | 0.17 |
| 21 | 0.07 |
| 22 | 2.15 |
| 23 | 1.10 |
| 24 | 0.47 |

TABLE 2

| EXAMPLE | IC$_{50}$ (μM) |
| --- | --- |
| 25 | 0.04 |
| 26 | 0.04 |
| 27 | 0.04 |
| 28 | 0.07 |
| 29 | 0.07 |
| 30 | 0.08 |
| 31 | 0.10 |
| 32 | 0.10 |
| 33 | 0.10 |
| 34 | 0.11 |
| 35 | 0.12 |
| 36 | 0.12 |
| 37 | 0.12 |
| 38 | 0.12 |
| 39 | 0.13 |
| 40 | 0.13 |
| 41 | 0.13 |
| 42 | 0.13 |
| 43 | 0.13 |
| 44 | 0.13 |
| 45 | 0.13 |

Example 101

1-(3-(4-Chloro-phenyl)-1-{4-[4-(2-methoxy-phenyl)-piperazin-1-yl]-butyl}-1,4,6,7-tetrahydro-pyrazolo[4,3-c]pyridin-5-yl)-ethanone Example 102

1-[1-(3-{4-[Bis-(4-fluoro-phenyl)-methyl]-piperazin-1-yl}-2-hydroxy-propyl)-3-(4-chloro-phenyl)-1,4,6,7-tetrahydro-pyrazolo[4,3-c]pyridin-5-yl]-ethanone Example 103

1-(3-(4-Chloro-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone Example 104

1-(3-(4-Chloro-phenyl)-1-{3-[4-(2-chloro-phenyl)-piperazin-1-yl]-2-hydroxy-propyl}-1,4,6,7-tetrahydro-pyrazolo[4,3-c]pyridin-5-yl)-ethanone Example 105

1-(3-(4-Chloro-phenyl)-1-{3-[4-(3-chloro-phenyl)-piperazin-1-yl]-2-hydroxy-propyl}-1,4,6,7-tetrahydro-pyrazolo[4,3-c]pyridin-5-yl)-ethanone

Example 106

1-(3-(4-Chloro-phenyl)-1-{3-[4-(4-chloro-phenyl)-piperazin-1-yl]-2-hydroxy-propyl}-1,4,6,7-tetrahydro-pyrazolo[4,3-c]pyridin-5-yl)-ethanone

Example 107

1-(3-(4-Chloro-phenyl)-1-{3-[4-(2-fluoro-phenyl)-piperazin-1-yl]-2-hydroxy-propyl}-1,4,6,7-tetrahydro-pyrazolo[4,3-c]pyridin-5-yl)-ethanone

Example 108

1-(3-(4-Chloro-phenyl)-1-{3-[4-(4-fluoro-phenyl)-piperazin-1-yl]-2-hydroxy-propyl}-1,4,6,7-tetrahydro-pyrazolo[4,3-c]pyridin-5-yl)-ethanone

Example 109

1-(3-(4-Chloro-phenyl)-1-{2-hydroxy-3-[4-(3-methoxy-phenyl)-piperazin-1-yl]-propyl}-1,4,6,7-tetrahydro-pyrazolo[4,3-c]pyridin-5-yl)-ethanone

Example 110

1-(3-(4-Chloro-phenyl)-1-{2-hydroxy-3-[4-(4-methoxy-phenyl)-piperazin-1-yl]-propyl}-1,4,6,7-tetrahydro-pyrazolo[4,3-c]pyridin-5-yl)-ethanone

Example 111

1-{3-(4-Chloro-phenyl)-1-[2-hydroxy-3-(4-phenyl-piperazin-1-yl)-propyl]-1,4,6,7-tetrahydro-pyrazolo[4,3-c]pyridin-5-yl}-ethanone

Example 112

1-[1-[3-(4-Benzhydryl-piperazin-1-yl)-2-hydroxy-propyl]-3-(4-chloro-phenyl)-1,4,6,7-tetrahydro-pyrazolo[4,3-c]pyridin-5-yl]-ethanone

Example 113

1-[3-(4-Chloro-phenyl)-1-(3-{4-[(4-chloro-phenyl)-phenyl-methyl]-piperazin-1-yl}-2-hydroxy-propyl)-1,4,6,7-tetrahydro-pyrazolo[4,3-c]pyridin-5-yl]-ethanone

Example 114

1-(3-(4-Chloro-phenyl)-1-{3-[4-(9H-fluoren-9-yl)-piperazin-1-yl]-2-hydroxy-propyl}-1,4,6,7-tetrahydro-pyrazolo[4,3-c]pyridin-5-yl)-ethanone

Example 115

1-[1-[3-(4-Benzyl-piperazin-1-yl)-2-hydroxy-propyl]-3-(4-chloro-phenyl)-1,4,6,7-tetrahydro-pyrazolo[4,3-c]pyridin-5-yl]-ethanone

Example 116

3-[5-Acetyl-3-(4-chloro-phenyl)-4,5,6,7-tetrahydro-pyrazolo[4,3-c]pyridin-1-yl]-1-[4-(2-methoxy-phenyl)-piperazin-1-yl]-propan-1-one

Example 117

1-[1-{2-Hydroxy-3-[4-(2-methoxy-phenyl)-piperazin-1-yl]-propyl}-3-(4-iodo-phenyl)-1,4,6,7-tetrahydro-pyrazolo[4,3-c]pyridin-5-yl]-ethanone

Example 118

1-(3-(4-Chloro-phenyl)-1-{2-hydroxy-3-[4-(2-trifluoromethyl-phenyl)-piperazin-1-yl]-propyl}-1,4,6,7-tetrahydro-pyrazolo[4,3-c]pyridin-5-yl)-ethanone

Example 119

1-(3-(4-Fluoro-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone

Example 120

4-[5-Acetyl-3-(4-chloro-phenyl)-4,5,6,7-tetrahydro-pyrazolo[4,3-c]pyridin-1-yl]-1-[4-(2-methoxy-phenyl)-piperazin-1-yl]-butan-1-one

Example 121

1-(1-{2-Hydroxy-3-[4-(2-methoxy-phenyl)-piperazin-1-yl]-propyl}-3-p-tolyl-1,4,6,7-tetrahydro-pyrazolo[4,3-c]pyridin-5-yl)-ethanone

Example 122

1-(3-(4-Chloro-phenyl)-1-{3-[4-(3,4-dichloro-phenyl)-piperazin-1-yl]-2-hydroxy-propyl}-1,4,6,7-tetrahydro-pyrazolo[4,3-c]pyridin-5-yl)-ethanone

Example 123

1-{3-(4-Chloro-phenyl)-1-[2-hydroxy-3-(4-pyridin-2-yl-piperazin-1-yl)-propyl]-1,4,6,7-tetrahydro-pyrazolo[4,3-c]pyridin-5-yl}-ethanone

Example 124

1-(3-Biphenyl-4-yl-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone

Example 125

1-(1-{2-Hydroxy-3-[4-(2-methoxy-phenyl)-piperazin-1-yl]-propyl}-3-phenyl-1,4,6,7-tetrahydro-pyrazolo[4,3-c]pyridin-5-yl)-ethanone

Example 126

1-[1-{2-Hydroxy-3-[4-(2-methoxy-phenyl)-piperazin-1-yl]-propyl}-3-(4-methoxy-phenyl)-1,4,6,7-tetrahydro-pyrazolo[4,3-c]pyridin-5-yl)-ethanone

Example 127

1-[1-[2-Hydroxy-3-(4-pyridin-4-yl-piperazin-1-yl)-propyl]-3-(4-methoxy-phenyl)-1,4,6,7-tetrahydro-pyrazolo[4,3-c]pyridin-5-yl]-ethanone

Example 129

1-[5-Acetyl-3-(4-chloro-phenyl)-4,5,6,7-tetrahydro-pyrazolo[4,3-c]pyridin-1-yl]-3-(4-o-tolyl-piperazin-1-yl)-propan-2-one

Example 130

3-(4-Chloro-phenyl)-1-{2-hydroxy-3-[4-(2-methoxy-phenyl)-piperazin-1-yl]-propyl}-1,4,6,7-tetrahydro-pyrazolo[4,3-c]pyridine-5-carboxylic acid tert-butyl ester

Example 131

1-(1-{2-Hydroxy-3-[4-(2-methoxy-phenyl)-piperazin-1-yl]-propyl}-3-naphthalen-2-yl-1,4,6,7-tetrahydro-pyrazolo[4,3-c]pyridin-5-yl)-ethanone

Example 132

1-(3-(4-tert-Butyl-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone

Example 133

1-(3-(4-Chloro-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-butan-1-one

Example 134

1-(3-(4-Chloro-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-2,2-dimethyl-propan-1-one

Example 136

(3-(4-Chloro-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-(4-methoxy-phenyl)-methanone

Example 137

3-(4-Chloro-phenyl)-1-{2-hydroxy-3-[4-(2-methoxy-phenyl)-piperazin-1-yl]-propyl}-1,4,6,7-tetrahydro-pyrazolo[4,3-c]pyridine-5-carboxylic acid amide

Example 138

1-[3-(4-Chloro-phenyl)-4,5,6,7-tetrahydro-pyrazolo[4,3-c]pyridin-1-yl]-3-[4-(2-methoxy-phenyl)-piperazin-1-yl]-propan-2-ol

Example 139

1-(3-(3,4-Dichloro-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone

Example 140

1-[1-{2-Hydroxy-3-[4-(2-methoxy-phenyl)-piperazin-1-yl]-propyl}-3-(4-trifluoromethyl-phenyl)-1,4,6,7-tetrahydro-pyrazolo[4,3-c]pyridin-5-yl]-ethanone

Example 141

1-[1-{2-Hydroxy-3-[4-(2-methoxy-phenyl)-piperazin-1-yl]-propyl}-3-(4-nitro-phenyl)-1,4,6,7-tetrahydro-pyrazolo[4,3-c]pyridin-5-yl]-ethanone

Example 142

1-(3-(4-Chloro-phenyl)-1-{3-[4-(2,4-difluoro-phenyl)-piperazin-1-yl]-2-hydroxy-propyl}-1,4,6,7-tetrahydro-pyrazolo[4,3-c]pyridin-5-yl)-ethanone

Example 143

2-(4-{3-[5-Acetyl-3-(4-chloro-phenyl)-4,5,6,7-tetrahydro-pyrazolo[4,3-c]pyridin-1-yl]-2-hydroxy-propyl}-piperazin-1-yl)-benzonitrile

Example 144

4-{3-[5-Acetyl-3-(4-chloro-phenyl)-4,5,6,7-tetrahydro-pyrazolo[4,3-c]pyridin-1-yl]-2-hydroxy-propyl}-3,4,5,6-tetrahydro-2H-[1,2']bipyrazinyl-3'-carbonitrile

Example 145

1-(3-(4-Chloro-phenyl)-1-{3-[4-(2,3-dimethyl-phenyl)-piperazin-1-yl]-2-hydroxy-propyl}-1,4,6,7-tetrahydro-pyrazolo[4,3-c]pyridin-5-yl)-ethanone

Example 146

1-(3-(4-Chloro-phenyl)-1-{3-[4-(2,4-dimethyl-phenyl)-piperazin-1-yl]-2-hydroxy-propyl}-1,4,6,7-tetrahydro-pyrazolo[4,3-c]pyridin-5-yl)-ethanone

Example 147

1-(3-(4-Chloro-phenyl)-1-{3-[4-(2,5-dimethyl-phenyl)-piperazin-1-yl]-2-hydroxy-propyl}-1,4,6,7-tetrahydro-pyrazolo[4,3-c]pyridin-5-yl)-ethanone

Example 148

1-{3-(4-Chloro-phenyl)-1-[2-hydroxy-3-(3-methyl-4-p-tolyl-piperazin-1-yl)-propyl]-1,4,6,7-tetrahydro-pyrazolo[4,3-c]pyridin-5-yl}-ethanone

Example 149

1-{3-(4-Chloro-phenyl)-1-[2-hydroxy-3-(3-methyl-4-m-tolyl-piperazin-1-yl)-propyl]-1,4,6,7-tetrahydro-pyrazolo[4,3-c]pyridin-5-yl}-ethanone

Example 150

1-(3-(4-Chloro-phenyl)-1-{2-hydroxy-3-[4-(4-trifluoromethyl-pyridin-2-yl)-piperazin-1-yl]-propyl}-1,4,6,7-tetrahydro-pyrazolo[4,3-c]pyridin-5-yl)-ethanone

Example 151

1-(3-(4-Chloro-phenyl)-1-{3-[4-(3-chloro-5-trifluoromethyl-pyridin-2-yl)-piperazin-1-yl]-2-hydroxy-propyl}-1,4,6,7-tetrahydro-pyrazolo[4,3-c]pyridin-5-yl)-ethanone Example 152

1-(3-(4-Chloro-phenyl)-1-{3-[4-(3,5-dichloro-pyridin-4-yl)-piperazin-1-yl]-2-hydroxy-propyl}-1,4,6,7-tetrahydro-pyrazolo[4,3-c]pyridin-5-yl)-ethanone Example 153

1-(3-(4-Chloro-phenyl)-1-{4-[4-(2-methoxy-phenyl)-piperazin-1-yl]-but-2-enyl}-1,4,6,7-tetrahydro-pyrazolo[4,3-c]pyridin-5-yl)-ethanone Example 154

4-(5-Acetyl-1-{2-hydroxy-3-[4-(2-methoxy-phenyl)-piperazin-1-yl]-propyl}-4,5,6,7-tetrahydro-1H-pyrazolo[4,3-c]pyridin-3-yl)-benzonitrile Example 155

1-{3-(4-Chloro-phenyl)-1-[2-hydroxy-3-(2,3,5,6-tetrahydro-[1,2']bipyrazinyl-4-yl)-propyl]-1,4,6,7-tetrahydro-pyrazolo[4,3-c]pyridin-5-yl}-ethanone Example 156

1-{3-(4-Chloro-phenyl)-1-[2-hydroxy-3-(4-pyrimidin-2-yl-piperazin-1-yl)-propyl]-1,4,6,7-tetrahydro-pyrazolo[4,3-c]pyridin-5-yl}-ethanone Example 157

1-(3-(2,4-Bis-trifluoromethyl-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone Example 158

1-(3-(2,4-Dichloro-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone Example 159

2-(4-{3-[3-(4-Chloro-phenyl)-5,6-dihydro-4H-cyclopentapyrazol-1-yl]-2-hydroxy-propyl}-piperazin-1-yl)-benzonitrile Example 160

2-(4-{3-[3-(4-Chloro-phenyl)-5,6-dihydro-4H-cyclopenta pyrazol-1-yl]-2-hydroxy-propyl}-piperazin-1-yl)-phenol Example 161

1-(3-(4-Bromo-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone Example 162

1-{3-(4-Chloro-phenyl)-1-[2-(2-methyl-allyloxy)-3-(4-o-tolyl-piperazin-1-yl)-propyl]-1,4,6,7-tetrahydro-pyrazolo[4,3-c]pyridin-5-yl}-ethanone Example 163

1-[1-[2-Benzyloxy-3-(4-o-tolyl-piperazin-1-yl)-propyl]-3-(4-chloro-phenyl)-1,4,6,7-tetrahydro-pyrazolo[4,3-c]pyridin-5-yl]-ethanone Example 164

Acetic acid 1-[5-acetyl-3-(4-chloro-phenyl)-4,5,6,7-tetrahydro-pyrazolo[4,3-c]pyridin-1-ylmethyl]-2-(4-o-tolyl-piperazin-1-yl)-ethyl ester Example 165

Morpholine-4-carboxylic acid 1-[5-acetyl-3-(4-chloro-phenyl)-4,5,6,7-tetrahydro-pyrazolo[4,3-c]pyridin-1-ylmethyl]-2-(4-o-tolyl-piperazin-1-yl)-ethyl ester Example 166

Benzoic acid 1-[5-acetyl-3-(4-chloro-phenyl)-4,5,6,7-tetrahydro-pyrazolo[4,3-c]pyridin-1-ylmethyl]-2-(4-o-tolyl-piperazin-1-yl)-ethyl ester Example 167

Benzoyl-carbamic acid 1-[5-acetyl-3-(4-chloro-phenyl)-4,5,6,7-tetrahydro-pyrazolo[4,3-c]pyridin-1-ylmethyl]-2-(4-o-tolyl-piperazin-1-yl)-ethyl ester Example 168

1-[3-(4-Chloro-phenyl)-pyrazol-1-yl]-3-(4-o-tolyl-piperazin-1-yl)-propan-2-ol

Example 169

1-(3-(3-Chloro-phenyl)-1-{2-hydroxy-3-[4-(2-hydroxy-phenyl)-piperazin-1-yl]-propyl}-1,4,6,7-tetrahydro-pyrazolo[4,3-c]pyridin-5-yl)-ethanone Example 170

2-(4-{3-[5-Acetyl-3-(3-chloro-phenyl)-4,5,6,7-tetrahydro-pyrazolo[4,3-c]pyridin-1-yl]-2-hydroxy-propyl}-piperazin-1-yl)-benzonitrile Example 171 tert-Butyl-carbamic acid 1-[5-acetyl-3-(4-chloro-phenyl)-4,5,6,7-tetrahydro-pyrazolo[4,3-c]pyridin-1-ylmethyl]-2-(4-o-tolyl-piperazin-1-yl)-ethyl ester Example 172

Carbonic acid 1-[5-acetyl-3-(4-chloro-phenyl)-4,5,6,7-tetrahydro-pyrazolo[4,3-c]pyridin-1-ylmethyl]-2-(4-o-tolyl-piperazin-1-yl)-ethyl ester methyl ester Example 173

1-(3-(4-Chloro-phenyl)-1-{4-[4-(2-hydroxy-phenyl)-piperazin-1-yl]-but-2-enyl}-1,4,6,7-tetrahydro-pyrazolo[4,3-c]pyridin-5-yl)-ethanone

Example 174

2-(4-{4-[5-Acetyl-3-(4-chloro-phenyl)-4,5,6,7-tetrahydro-pyrazolo[4,3-c]pyridin-1-yl]-but-2-enyl}-piperazin-1-yl)-benzonitrile

Example 175

1-(3-(4-Chloro-phenyl)-1-{4-[4-(2-methoxy-phenyl)-piperazin-1-yl]-but-2-enyl}-1,4,6,7-tetrahydro-pyrazolo[4,3-c]pyridin-5-yl)-ethanone

Example 176

1-(3-(4-Chloro-phenyl)-1-{3-[4-(2-methoxy-phenyl)-piperazin-1-yl]-propyl}-1,4,6,7-tetrahydro-pyrazolo[4,3-c]pyridin-5-yl)-ethanone

Example 177

1-(3-(4-Chloro-phenyl)-1-{5-[4-(2-methoxy-phenyl)-piperazin-1-yl]-pentyl}-1,4,6,7-tetrahydro-pyrazolo[4,3-c]pyridin-5-yl)-ethanone

Example 178

1-(3-(4-Chloro-phenyl)-1-{6-[4-(2-methoxy-phenyl)-piperazin-1-yl]-hexyl}-1,4,6,7-tetrahydro-pyrazolo[4,3-c]pyridin-5-yl)-ethanone

Example 179

2-[1-[5-Acetyl-3-(4-chloro-phenyl)-4,5,6,7-tetrahydro-pyrazolo[4,3-c]pyridin-1-ylmethyl]-2-(4-o-tolyl-piperazin-1-yl)-ethoxy]-acetamide

Example 180

[1-[5-Acetyl-3-(4-chloro-phenyl)-4,5,6,7-tetrahydro-pyrazolo[4,3-c]pyridin-1-ylmethyl]-2-(4-o-tolyl-piperazin-1-yl)-ethoxy]-acetic acid

Example 181

[1-[5-Acetyl-3-(4-chloro-phenyl)-4,5,6,7-tetrahydro-pyrazolo[4,3-c]pyridin-1-ylmethyl]-2-(4-o-tolyl-piperazin-1-yl)-ethoxy]-acetonitrile

Example 182

1-[1-{3-[4-(2-Bromo-benzenesulfonyl)-piperazin-1-yl]-2-hydroxy-propyl}-3-(4-chloro-phenyl)-1,4,6,7-tetrahydro-pyrazolo[4,3-c]pyridin-5-yl]-ethanone

Example 183

3-(5-(4-Chloro-phenyl)-2-{3-[4-(2-cyano-phenyl)-piperazin-1-yl]-2-hydroxy-propyl}-2H-pyrazol-3-yl)-propionic acid methyl ester

Example 184

2-(4-{3-[3-(4-Chloro-phenyl)-4,5,6,7-tetrahydro-indazol-1-yl]-2-hydroxy-propyl}-piperazin-1-yl)-benzonitrile

Example 185

2-(4-{3-[3-(4-Chloro-phenyl)-4,5,6,7-tetrahydro-indazol-1-yl]-2-hydroxy-propyl}-piperazin-1-yl)-phenol

Example 186

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carboxylic acid dimethylamide

Example 187

1-[1-[2-Azido-3-(4-o-tolyl-piperazin-1-yl)-propyl]-3-(4-chloro-phenyl)-1,4,6,7-tetrahydro-pyrazolo[4,3-c]pyridin-5-yl]-ethanone

Example 188

1-[1-[2-Amino-3-(4-o-tolyl-piperazin-1-yl)-propyl]-3-(4-chloro-phenyl)-1,4,6,7-tetrahydro-pyrazolo[4,3-c]pyridin-5-yl]-ethanone

Example 189

1-{3-(4-Chloro-phenyl)-1-[2-methylamino-3-(4-o-tolyl-piperazin-1-yl)-propyl]-1,4,6,7-tetrahydro-pyrazolo[4,3-c]pyridin-5-yl}-ethanone

Example 190

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carboxylic acid amide

Example 191

3-(4-Chloro-phenyl)-1-{2-hydroxy-3-[4-(2-methoxy-phenyl)-piperazin-1-yl]-propyl}-1,4,6,7-tetrahydro-indazol-5-one ethylene ketal

Example 192

1-[2-Hydroxy-3-(4-o-tolyl-piperazin-1-yl)-propyl]-3-(4-iodo-phenyl)-1,4,6,7-tetrahydro-pyrazolo[4,3-c]pyridine-5-carboxylic acid tert-butyl ester

Example 193

1-(3-(4-Chloro-3-methyl-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone

Example 194

2-(4-{3-[5-Acetyl-3-(4-chloro-3-methyl-phenyl)-4,5,6,7-tetrahydro-pyrazolo[4,3-c]pyridin-1-yl]-2-hydroxy-propyl}-piperazin-1-yl)-benzonitrile

Example 195

1-[1-{3-[4-(2-Chloro-benzenesulfonyl)-piperazin-1-yl]-2-hydroxy-propyl}-3-(4-chloro-phenyl)-1,4,6,7-tetrahydro-pyrazolo[4,3-c]pyridin-5-yl]-ethanone

Example 196

1-(3-(4-Chloro-2-fluoro-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone

Example 197

2-(4-{3-[5-Acetyl-3-(4-chloro-2-fluoro-phenyl)-4,5,6,7-tetrahydro-pyrazolo[4,3-c]pyridin-1-yl]-2-hydroxy-propyl}-piperazin-1-yl)-benzonitrile

Example 198

1-[3-(4-Chloro-phenyl)-5-methyl-4,5,6,7-tetrahydro-pyrazolo[4,3-c]pyridin-1-yl]-3-(4-o-tolyl-piperazin-1-yl)-propan-2-ol

Example 199

1-{3-(4-Chloro-phenyl)-1-[2-hydroxy-3-(4-o-tolyl-piperazin-1-yl)-propyl]-1,4,6,7-tetrahydro-pyrazolo[4,3-c]pyridin-5-yl}-2-phenyl-ethanone

Example 200

1-[3-(4-Chloro-phenyl)-5-methanesulfonyl-4,5,6,7-tetrahydro-pyrazolo[4,3-c]pyridin-1-yl]-3-(4-o-tolyl-piperazin-1-yl)-propan-2-ol

Example 201

1-[1-{3-[4-(2-Amino-phenyl)-piperazin-1-yl]-2-hydroxy-propyl}-3-(4-chloro-phenyl)-1,4,6,7-tetrahydro-pyrazolo[4,3-c]pyridin-5-yl]-ethanone

Example 202

N-[2-(4-{3-[5-Acetyl-3-(4-chloro-phenyl)-4,5,6,7-tetrahydro-pyrazolo[4,3-c]pyridin-1-yl]-2-hydroxy-propyl}-piperazin-1-yl)-phenyl]-methanesulfonamide

Example 203

N-[2-(4-{3-[5-Acetyl-3-(4-chloro-phenyl)-4,5,6,7-tetrahydro-pyrazolo[4,3-c]pyridin-1-yl]-2-hydroxy-propyl}-piperazin-1-yl)-phenyl]-acetamide

Example 204

1-[2-(4-{3-[5-Acetyl-3-(4-chloro-phenyl)-4,5,6,7-tetrahydro-pyrazolo[4,3-c]pyridin-1-yl]-2-hydroxy-propyl}-piperazin-1-yl)-phenyl]-3-isopropyl-urea

Example 205

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carboxylic acid methylamide

Example 206

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carboxylic acid hydrazide

Example 207

2-(4-{3-[5-Acetyl-3-(4-phenoxy-phenyl)-4,5,6,7-tetrahydro-pyrazolo[4,3-c]pyridin-1-yl]-2-hydroxy-propyl}-piperazin-1-yl)-benzonitrile

Example 208

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carboxylic acid phenethyl-amide

Example 209

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carboxylic acid (4-methoxy-phenyl)-amide

Example 210

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carbothioic acid methylamide

Example 211

2-(4-{3-[5-Acetyl-3-(4-chloro-3-nitro-phenyl)-4,5,6,7-tetrahydro-pyrazolo[4,3-c]pyridin-1-yl]-2-hydroxy-propyl}-piperazin-1-yl)-benzonitrile

Example 212

1-[2-Hydroxy-3-(4-o-tolyl-piperazin-1-yl)-propyl]-3-(4-iodo-phenyl)-1,4,6,7-tetrahydro-pyrazolo[4,3-c]pyridine-5-carboxylic acid ethylamide

Example 213

N-(5-{5-Acetyl-1-[2-hydroxy-3-(4-o-tolyl-piperazin-1-yl)-propyl]-4,5,6,7-tetrahydro-1H-pyrazolo[4,3-c]pyridin-3-yl}-2-chloro-phenyl)-methanesulfonamide

Example 214

1-{3-(4-Chloro-phenyl)-1-[2-[(1-ethyl-pyrrolidin-2-ylmethyl)-amino]-3-(4-o-tolyl-piperazin-1-yl)-propyl]-1,4,6,7-tetrahydro-pyrazolo[4,3-c]pyridin-5-yl}-ethanone

Example 215

2-(4-{3-[5-Acetyl-3-(4-trifluoromethylsulfanyl-phenyl)-4,5,6,7-tetrahydro-pyrazolo[4,3-c]pyridin-1-yl]-2-hydroxy-propyl}-piperazin-1-yl)-benzonitrile

Example 216

2-(4-{3-[5-Acetyl-3-(3-amino-4-chloro-phenyl)-4,5,6,7-tetrahydro-pyrazolo[4,3-c]pyridin-1-yl]-2-hydroxy-propyl}-piperazin-1-yl)-benzonitrile

Example 217

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carboxylic acid isopropylamide

Example 218

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carboxylic acid phenylamide

Example 219

1-[3-(4-Chloro-phenyl)-4,5,6,7-tetrahydro-pyrazolo[4,3-c]pyridin-1-yl]-3-(4-o-tolyl-piperazin-1-yl)-propan-2-ol

Example 220

1-[3-(4-Iodo-phenyl)-4,5,6,7-tetrahydro-pyrazolo[4,3-c]pyridin-1-yl]-3-(4-o-tolyl-piperazin-1-yl)-propan-2-ol

Example 221

2-(4-{3-[5-Acetyl-3-(4-methanesulfonyl-phenyl)-4,5,6,7-tetrahydro-pyrazolo[4,3-c]pyridin-1-yl]-2-hydroxy-propyl}-piperazin-1-yl)-benzonitrile

Example 222

1-[1-{2-Hydroxy-3-[4-(2-hydroxy-phenyl)-piperazin-1-yl]-propyl}-3-(4-methanesulfonyl-phenyl)-1,4,6,7-tetrahydro-pyrazolo[4,3-c]pyridin-5-yl]-ethanone

Example 223

1-[3-(4-Iodo-phenyl)-5-methanesulfonyl-4,5,6,7-tetrahydro-pyrazolo[4,3-c]pyridin-1-yl]-3-(4-o-tolyl-piperazin-1-yl)-propan-2-ol

Example 224

1-[2-Hydroxy-3-(4-o-tolyl-piperazin-1-yl)-propyl]-3-(4-iodo-phenyl)-1,4,6,7-tetrahydro-pyrazolo[4,3-c]pyridine-5-carboxylic acid amide

Example 225

1-[2-Hydroxy-3-(4-o-tolyl-piperazin-1-yl)-propyl]-3-(4-iodo-phenyl)-1,4,6,7-tetrahydro-pyrazolo[4,3-c]pyridine-5-carboxylic acid methyl ester

Example 226

1-[2-Hydroxy-3-(4-o-tolyl-piperazin-1-yl)-propyl]-3-(4-iodo-phenyl)-1,4,6,7-tetrahydro-pyrazolo[4,3-c]pyridine-5-carboxylic acid methylamide

Example 227

N-[5-(5-Acetyl-1-{3-[4-(2-cyano-phenyl)-piperazin-1-yl]-2-hydroxy-propyl}-4,5,6,7-tetrahydro-1H-pyrazolo[4,3-c]pyridin-3-yl)-2-chloro-phenyl]-methanesulfonamide

Example 228

1-(5-{5-Acetyl-1-[2-hydroxy-3-(4-o-tolyl-piperazin-1-yl)-propyl]-4,5,6,7-tetrahydro-1H-pyrazolo[4,3-c]pyridin-3-yl}-2-chloro-phenyl)-3-ethyl-urea

Example 229

1-[5-(5-Acetyl-1-{3-[4-(2-cyano-phenyl)-piperazin-1-yl]-2-hydroxy-propyl}-4,5,6,7-tetrahydro-1H-pyrazolo[4,3-c]pyridin-3-yl)-2-chloro-phenyl]-3-ethyl-urea

Example 230

N-(5-{5-Acetyl-1-[2-hydroxy-3-(4-o-tolyl-piperazin-1-yl)-propyl]-4,5,6,7-tetrahydro-1H-pyrazolo[4,3-c]pyridin-3-yl}-2-chloro-phenyl)-acetamide

Example 231

Acetic acid 2-[5-acetyl-3-(3-amino-4-chloro-phenyl)-4,5,6,7-tetrahydro-pyrazolo[4,3-c]pyridin-1-yl]-1-[4-(2-cyano-phenyl)-piperazin-1-ylmethyl]-ethyl ester

Example 232

N-[5-(5-Acetyl-1-{3-[4-(2-cyano-phenyl)-piperazin-1-yl]-2-hydroxy-propyl}-4,5,6,7-tetrahydro-1H-pyrazolo[4,3-c]pyridin-3-yl)-2-chloro-phenyl]-acetamide

Example 233

N-[2-[5-Acetyl-3-(4-chloro-phenyl)-4,5,6,7-tetrahydro-pyrazolo[4,3-c]pyridin-1-yl]-1-(4-o-tolyl-piperazin-1-ylmethyl)-ethyl]-methanesulfonamide

Example 234

1-{3-(4-Chloro-phenyl)-1-[2-(2-pyridin-2-yl-ethylamino)-3-(4-o-tolyl-piperazin-1-yl)-propyl]-1,4,6,7-tetrahydro-pyrazolo[4,3-c]pyridin-5-yl}-ethanone

Example 235

1-{3-(4-Chloro-phenyl)-1-[2-(2-dimethylamino-ethylamino)-3-(4-o-tolyl-piperazin-1-yl)-propyl]-1,4,6,7-tetrahydro-pyrazolo[4,3-c]pyridin-5-yl}-ethanone

Example 236

Carbonic acid 2-[5-acetyl-3-(4-trifluoromethyl-phenyl)-4,5,6,7-tetrahydro-pyrazolo[4,3-c]pyridin-1-yl]-1-(4-o-tolyl-piperazin-1-ylmethyl)-ethyl ester methyl ester

Example 237

Carbamic acid 2-[5-acetyl-3-(4-trifluoromethyl-phenyl)-4,5,6,7-tetrahydro-pyrazolo[4,3-c]pyridin-1-yl]-1-(4-o-tolyl-piperazin-1-ylmethyl)-ethyl ester

Example 238

3-(4-Chloro-phenyl)-1-[2-hydroxy-3-(4-o-tolyl-piperazin-1-yl)-propyl]-1,4,6,7-tetrahydro-indazol-5-one

Example 239

3-(4-Chloro-phenyl)-1-[2-hydroxy-3-(4-o-tolyl-piperazin-1-yl)-propyl]-4,5,6,7-tetrahydro-1H-indazol-5-ol

Example 240

3-(4-Chloro-phenyl)-1-[2-hydroxy-3-(4-o-tolyl-piperazin-1-yl)-propyl]-1,4,6,7-tetrahydro-indazol-5-one oxime

Example 241

1-[5-Ethanesulfonyl-3-(4-iodo-phenyl)-4,5,6,7-tetrahydro-pyrazolo[4,3-c]pyridin-1-yl]-3-(4-o-tolyl-piperazin-1-yl)-propan-2-ol

Example 242

1-[2-Hydroxy-3-(4-o-tolyl-piperazin-1-yl)-propyl]-3-(4-iodo-phenyl)-1,4,6,7-tetrahydro-pyrazolo[4,3-c]pyridine-5-carboxylic acid methyl ester

Example 243

1-[5-(4-Chloro-benzenesulfonyl)-3-(4-iodo-phenyl)-4,5,6,7-tetrahydro-pyrazolo[4,3-c]pyridin-1-yl]-3-(4-o-tolyl-piperazin-1-yl)-propan-2-ol

Example 244

1-{3-[4-(2-Cyano-phenyl)-piperazin-1-yl]-2-hydroxy-propyl}-3-(4-iodo-phenyl)-1,4,6,7-tetrahydro-pyrazolo[4,3-c]pyridine-5-carboxylic acid methylamide

Example 245

1-[3-(4-Iodo-phenyl)-5-(propane-2-sulfonyl)-4,5,6,7-tetrahydro-pyrazolo[4,3-c]pyridin-1-yl]-3-(4-o-tolyl-piperazin-1-yl)-propan-2-ol

Example 246

1-{3-[4-(2-Cyano-phenyl)-piperazin-1-yl]-2-hydroxy-propyl}-3-(4-iodo-phenyl)-1,4,6,7-tetrahydro-pyrazolo[4,3-c]pyridine-5-carbonitrile

Example 247

4-{3-[5-Acetyl-3-(4-chloro-3-methyl-phenyl)-4,5,6,7-tetrahydro-pyrazolo[4,3-c]pyridin-1-yl]-2-hydroxy-propyl}-piperazine-1-carboxylic acid o-tolylamide

Example 248

4-{3-[5-Acetyl-3-(4-chloro-3-methyl-phenyl)-4,5,6,7-tetrahydro-pyrazolo[4,3-c]pyridin-1-yl]-2-hydroxy-propyl}-piperazine-1-carboxylic acid (2-methoxy-phenyl)-amide

Example 249

2-(4-{3-[5-Acetyl-3-(3-chloro-4-trifluoromethyl-phenyl)-4,5,6,7-tetrahydro-pyrazolo[4,3-c]pyridin-1-yl]-2-hydroxy-propyl}-piperazin-1-yl)-benzonitrile

Example 250

2-(4-{3-[5-Acetyl-3-(3-fluoro-4-trifluoromethyl-phenyl)-4,5,6,7-tetrahydro-pyrazolo[4,3-c]pyridin-1-yl]-2-hydroxy-propyl}-piperazin-1-yl)-benzonitrile

Example 251

2-(4-{3-[5-Acetyl-3-(4-chloro-3-methyl-phenyl)-4,5,6,7-tetrahydro-pyrazolo[4,3-c]pyridin-1-yl]-2-hydroxy-propyl}-piperazin-1-ylmethyl)-benzonitrile

Example 252

1-(3-(4-Chloro-3-methyl-phenyl)-1-{2-hydroxy-3-[4-(2-methoxy-benzyl)-piperazin-1-yl]-propyl}-1,4,6,7-tetrahydro-pyrazolo[4,3-c]pyridin-5-yl)-ethanone

Example 253

2-(4-{3-[5-Acetyl-3-(4-bromo-3-methyl-phenyl)-4,5,6,7-tetrahydro-pyrazolo[4,3-c]pyridin-1-yl]-2-hydroxy-propyl}-piperazin-1-yl)-benzonitrile

Example 254

3-(4-Chloro-phenyl)-1-[2-hydroxy-3-(4-o-tolyl-piperazin-1-yl)-propyl]-1,4,6,7-tetrahydro-pyrazolo[4,3-c]pyridine-5-carboxamidine

Example 255

2-(4-{3-[5-Acetyl-3-(3,4-dichloro-phenyl)-4,5,6,7-tetrahydro-pyrazolo[4,3-c]pyridin-1-yl]-2-hydroxy-propyl}-piperazin-1-yl)-benzonitrile

Example 256

2-(4-{3-[5-Acetyl-3-(3,4-difluoro-phenyl)-4,5,6,7-tetrahydro-pyrazolo[4,3-c]pyridin-1-yl]-2-hydroxy-propyl}-piperazin-1-yl)-benzonitrile

Example 257

2-(4-{3-[5-Acetyl-3-(3,5-dichloro-phenyl)-4,5,6,7-tetrahydro-pyrazolo[4,3-c]pyridin-1-yl]-2-hydroxy-propyl}-piperazin-1-yl)-benzonitrile

Example 258

2-{4-[3-[5-Acetyl-3-(4-trifluoromethyl-phenyl)-4,5,6,7-tetrahydro-pyrazolo[4,3-c]pyridin-1-yl]-2-(2-morpholin-4-yl-ethoxy)-propyl]-piperazin-1-yl}-benzonitrile

Example 259

2-(4-{2-Hydroxy-3-[3-(4-iodo-phenyl)-5-trifluoromethanesulfonyl-4,5,6,7-tetrahydro-pyrazolo[4,3-c]pyridin-1-yl]-propyl}-piperazin-1-yl)-benzonitrile

Example 260

2-(4-{3-[5-Acetyl-3-(3-chloro-4-methyl-phenyl)-4,5,6,7-tetrahydro-pyrazolo[4,3-c]pyridin-1-yl]-2-hydroxy-propyl}-piperazin-1-yl)-benzonitrile

Example 261

N-[4-(5-Acetyl-1-{3-[4-(2-cyano-phenyl)-piperazin-1-yl]-2-hydroxy-propyl}-4,5,6,7-tetrahydro-1H-pyrazolo[4,3-c]pyridin-3-yl)-phenyl]-acetamide

Example 262

2-(4-{3-[5-Acetyl-3-(4-bromo-3-chloro-phenyl)-4,5,6,7-tetrahydro-pyrazolo[4,3-c]pyridin-1-yl]-2-hydroxy-propyl}-piperazin-1-yl)-benzonitrile

Example 263

1-(3-(3-Chloro-4-methyl-phenyl)-1-{2-hydroxy-3-[4-(2-methoxy-phenyl)-piperazin-1-yl]-propyl}-1,4,6,7-tetrahydro-pyrazolo[4,3-c]pyridin-5-yl)-ethanone

Example 264

1-[1-{3-[4-(2-Azido-phenyl)-piperazin-1-yl]-2-hydroxy-propyl}-3-(4-bromo-phenyl)-1,4,6,7-tetrahydro-pyrazolo[4,3-c]pyridin-5-yl]-ethanone

Example 265

2-(4-{3-[5-Acetyl-3-(3-azido-4-chloro-phenyl)-4,5,6,7-tetrahydro-pyrazolo[4,3-c]pyridin-1-yl]-2-hydroxy-propyl}-piperazin-1-yl)-benzonitrile

Example 266

5-Methanesulfonyl-1-[3-(4-o-tolyl-piperazin-1-yl)-propyl]-3-(4-trifluoromethyl-phenyl)-4,5,6,7-tetrahydro-1H-pyrazolo[4,3-c]pyridine

Example 267

5-Methanesulfonyl-1-{3-[4-(2-methoxy-phenyl)-piperazin-1-yl]-propyl}-3-(4-trifluoromethyl-phenyl)-4,5,6,7-tetrahydro-1H-pyrazolo[4,3-c]pyridine

Example 268

1-[1-{2-Hydroxy-3-[4-(2-nitro-phenyl)-piperazin-1-yl]-propyl}-3-(4-nitro-phenyl)-1,4,6,7-tetrahydro-pyrazolo[4,3-c]pyridin-5-yl]-ethanone

Example 269

3-(4-Bromo-phenyl)-1-{3-[4-(2-nitro-phenyl)-piperazin-1-yl]-propyl}-1,4,6,7-tetrahydro-pyrazolo[4,3-c]pyridine-5-carboxylic acid tert-butyl ester

Example 270

3-(4-Bromo-phenyl)-1-{3-[4-(2-nitro-phenyl)-piperazin-1-yl]-propyl}-4,5,6,7-tetrahydro-1H-pyrazolo[4,3-c]pyridine

Example 271

1-(3-(4-Bromo-phenyl)-1-{3-[4-(2-nitro-phenyl)-piperazin-1-yl]-propyl}-1,4,6,7-tetrahydro-pyrazolo[4,3-c]pyridin-5-yl)-ethanone

Example 272

3-(4-Bromo-phenyl)-5-methanesulfonyl-1-{3-[4-(2-nitro-phenyl)-piperazin-1-yl]-propyl}-4,5,6,7-tetrahydro-1H-pyrazolo[4,3-c]pyridine

Example 273

3-(3,4-Dichloro-phenyl)-1-{3-[4-(2-nitro-phenyl)-piperazin-1-yl]-propyl}-1,4,6,7-tetrahydro-pyrazolo[4,3-c]pyridine-5-carboxylic acid tert-butyl ester

Example 274

3-(4-Bromo-phenyl)-1-{3-[4-(2-nitro-phenyl)-piperazin-1-yl]-propyl}-1,4,6,7-tetrahydro-pyrazolo[4,3-c]pyridine-5-sulfonic acid amide

Example 275

1-(3-(3,4-Dichloro-phenyl)-1-{3-[4-(2-nitro-phenyl)-piperazin-1-yl]-propyl}-1,4,6,7-tetrahydro-pyrazolo[4,3-c]pyridin-5-yl)-ethanone

Example 276

3-(3,4-Dichloro-phenyl)-5-methanesulfonyl-1-{3-[4-(2-nitro-phenyl)-piperazin-1-yl]-propyl}-4,5,6,7-tetrahydro-1H-pyrazolo[4,3-c]pyridine

Example 277

3-(4-Bromo-phenyl)-1-{3-[4-(1,1-dioxo-1H-1$\lambda^6$-benzo[d]isothiazol-3-yl)-piperazin-1-yl]-propyl}-5-methanesulfonyl-4,5,6,7-tetrahydro-1H-pyrazolo[4,3-c]pyridine

Example 278

1-[1-[3-(4-Benzo[d]isothiazol-3-yl-piperazin-1-yl)-propyl]-3-(4-bromo-phenyl)-1,4,6,7-tetrahydro-pyrazolo[4,3-c]pyridin-5-yl]-ethanone

Example 279

1-[3-(4-Benzo[d]isothiazol-3-yl-piperazin-1-yl)-propyl]-3-(4-bromo-phenyl)-5-methanesulfonyl-4,5,6,7-tetrahydro-1H-pyrazolo[4,3-c]pyridine

Example 280

1-[3-(4-Benzo[d]isothiazol-3-yl-piperazin-1-yl)-propyl]-3-(4-bromo-phenyl)-1,4,6,7-tetrahydro-pyrazolo[4,3-c]pyridine-5-carboxylic acid tert-butyl ester

Example 281

1-[3-(4-Benzo[d]isothiazol-3-yl-piperazin-1-yl)-propyl]-3-(4-bromo-phenyl)-4,5,6,7-tetrahydro-1H-pyrazolo[4,3-c]pyridine

Example 282

1-[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-3-methyl-urea

Example 283

[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-urea

Example 284

[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-carbamic acid methyl ester

Example 285

1-[3-Chloro-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-3-methyl-urea

Example 286

N-[3-Chloro-2-(4-{3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-methanesulfonamide

Example 287

1-[4-(2,6-Dimethyl-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol

Example 288

1-[1-{3-[4-(2,6-Dimethyl-phenyl)-piperazin-1-yl]-2-hydroxy-propyl}-3-(4-trifluoromethyl-phenyl)-1,4,6,7-tetrahydro-pyrazolo[4,3-c]pyridin-5-yl]-ethanone

Example 289

2-(4-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-isophthalonitrile

Example 290

2-(4-{3-[5-Acetyl-3-(4-trifluoromethyl-phenyl)-4,5,6,7-tetrahydro-pyrazolo[4,3-c]pyridin-1-yl]-2-hydroxy-propyl}-piperazin-1-yl)-isophthalonitrile

Example 291

1-[4-(2-Chloro-6-nitro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol

Example 292

1-[4-(2-Amino-6-chloro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol

Example 293

3-Chloro-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-benzoic acid methyl ester

Example 294

3-Chloro-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)—N-methyl-benzamide

Example 295

[3-Chloro-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-phenyl]-morpholin-4-yl-methanone

Example 296

1-[4-(2-Chloro-6-morpholin-4-ylmethyl-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol

Example 297

3-Chloro-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-N-pyridin-4-ylmethyl-benzamide

Example 299

2-(4-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-3-nitro-benzoic acid methyl ester

Example 300

2-(4-{3-[5-Acetyl-3-(4-trifluoromethyl-phenyl)-4,5,6,7-tetrahydro-pyrazolo[4,3-c]pyridin-1-yl]-2-hydroxy-propyl}-piperazin-1-yl)-3-nitro-benzoic acid methyl ester

Example 301

3-Acetylamino-2-(4-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-benzoic acid methyl ester

Example 302

2-(4-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-3-methanesulfonylamino-benzoic acid methyl ester

Example 303

2-(4-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-3-nitro-benzamide

Example 304

2-(4-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperazin-1-yl)-3-(3-methyl-ureido)-benzoic acid methyl ester

Example 305

1-[4-(2,6-Dinitro-phenyl)-piperazin-1-yl]-3-[5-methanesulfonyl-3-(4-trifluoromethyl-phenyl)-4,5,6,7-tetrahydro-pyrazolo[4,3-c]pyridin-1-yl]-propan-2-ol

Example 306

1-[1-{3-[4-(2,6-Dinitro-phenyl)-piperazin-1-yl]-2-hydroxy-propyl}-3-(4-trifluoromethyl-phenyl)-1,4,6,7-tetrahydro-pyrazolo[4,3-c]pyridin-5-yl]-ethanone

Example 307

1-[1-{3-[4-(3,5-Dichloro-pyridin-4-yl)-piperazin-1-yl]-2-hydroxy-propyl}-3-(4-trifluoromethyl-phenyl)-1,4,6,7-tetrahydro-pyrazolo[4,3-c]pyridin-5-yl]-ethanone

Example 308

1-{3-[4-(3,5-Dichloro-pyridin-4-yl)-piperazin-1-yl]-propyl}-5-methanesulfonyl-3-(4-trifluoromethyl-phenyl)-4,5,6,7-tetrahydro-1H-pyrazolo[4,3-c]pyridine

Example 309

1-[1-{3-[4-(3,5-Dichloro-pyridin-4-yl)-piperazin-1-yl]-2-hydroxy-propyl}-3-(4-trifluoromethylsulfanyl-phenyl)-1,4,6,7-tetrahydro-pyrazolo[4,3-c]pyridin-5-yl]-ethanone

Example 310

1-[1-{3-[4-(3,5-Dichloro-pyridin-4-yl)-piperazin-1-yl]-propyl}-3-(4-trifluoromethyl-phenyl)-1,4,6,7-tetrahydro-pyrazolo[4,3-c]pyridin-5-yl]-ethanone

Example 311

2-(4-{3-[5-Acetyl-3-(4-bromo-phenyl)-4,5,6,7-tetrahydro-pyrazolo[4,3-c]pyridin-1-yl]-2-azido-propyl}-piperazin-1-yl)-benzonitrile

Example 312

1-[1-{2-Hydroxy-3-[4-(6-nitro-benzothiazol-2-yl)-piperazin-1-yl]-propyl}-3-(4-trifluoromethyl-phenyl)-1,4,6,7-tetrahydro-pyrazolo[4,3-c]pyridin-5-yl]-ethanone

Example 313

1-[1-{2-Hydroxy-3-[4-(6-methoxy-benzothiazol-2-yl)-piperazin-1-yl]-propyl}-3-(4-trifluoromethyl-phenyl)-1,4,6,7-tetrahydro-pyrazolo[4,3-c]pyridin-5-yl]-ethanone

Example 314

1-{3-[4-(1,1-Dioxo-1H-1$\lambda^6$-benzo[d]isothiazol-3-yl)-piperazin-1-yl]-propyl}-5-methanesulfonyl-3-(4-trifluoromethyl-phenyl)-4,5,6,7-tetrahydro-1H-pyrazolo[4,3-c]pyridine

Example 315

1-[3-(4-Benzo[d]isothiazol-3-yl-piperazin-1-yl)-propyl]-3-(4-bromo-phenyl)-1,4,6,7-tetrahydro-pyrazolo[4,3-c]pyridine-5-carboxylic acid amide

TABLE 3

| EXAMPLE | $IC_{50}$ (μM) |
| --- | --- |
| 103 | 2.1 |
| 109 | 1.2 |
| 114 | 1.1 |
| 120 | 12 |
| 121 | 4.3 |
| 123 | 1.9 |
| 126 | 7.4 |
| 131 | 2.2 |
| 135 | 1.4 |
| 137 | 0.98 |
| 139 | 0.71 |
| 140 | 0.53 |
| 141 | 1.4 |
| 143 | 0.35 |
| 148 | 0.63 |
| 149 | 0.86 |
| 150 | 1.8 |
| 156 | 2.9 |
| 159 | 6.2 |
| 164 | 1.9 |
| 167 | 4.9 |
| 170 | 4.5 |
| 174 | 1.4 |
| 176 | 1.6 |
| 181 | 1.7 |
| 185 | 8.4 |
| 190 | 0.26 |
| 192 | 0.79 |
| 193 | 0.33 |
| 195 | 3.3 |
| 196 | 1.9 |
| 199 | 1.6 |
| 205 | 0.95 |
| 208 | 1.5 |
| 211 | 0.16 |
| 214 | 1.9 |
| 216 | 1.3 |
| 219 | 10 |
| 221 | 0.82 |
| 223 | 0.23 |
| 224 | 0.14 |
| 228 | 2.7 |
| 230 | 0.81 |
| 237 | 1.5 |
| 238 | 3.6 |
| 245 | 0.44 |
| 247 | 4.9 |
| 249 | 0.47 |
| 251 | 4.6 |
| 255 | 0.40 |
| 258 | 0.39 |
| 260 | 0.24 |
| 262 | 0.29 |
| 266 | 0.19 |
| 267 | 0.22 |
| 270 | 1.8 |
| 272 | 0.15 |
| 277 | 2.8 |
| 278 | 0.19 |
| 281 | 2.5 |

TABLE 3-continued

| EXAMPLE | IC$_{50}$ (μM) |
|---|---|
| 283 | 0.08 |
| 285 | 0.04 |
| 287 | 0.20 |
| 289 | 0.15 |
| 293 | 0.14 |
| 296 | 0.48 |
| 302 | 0.07 |
| 306 | 0.34 |
| 310 | 0.40 |
| 311 | 2.1 |
| 312 | 0.77 |

F. OTHER EMBODIMENTS

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

The invention claimed is:

1. A compound of formula (I) below:

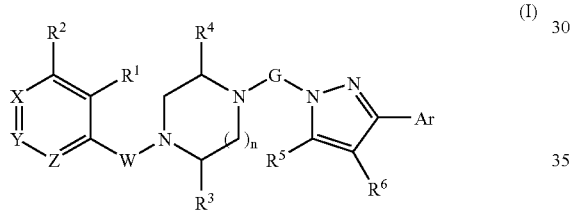

(I)

wherein:
R$^1$ is hydrogen, azido, halogen, C$_{1-5}$ alkoxy, hydroxy, C$_{1-5}$ alkyl, C$_{2-5}$ alkenyl, cyano, nitro, R$^7$R$^8$N, C$_{2-8}$ acyl, R$^9$OC=O, R$^{10}$R$^{11}$NC=O, or R$^{10}$R$^{11}$NSO$_2$; or R$^1$ is taken together with W as described below;
R$^2$ is hydrogen, halogen, C$_{1-5}$ alkoxy, C$_{1-5}$ alkyl, C$_{2-5}$ alkenyl, C$_{1-5}$ haloalkyl, cyano, or R$^{48}$R$^{49}$N;
alternatively, R$^1$ and R$^2$ can be taken together to form an optionally substituted 5- to 7-membered carbocyclic or heterocyclic ring, which ring may be unsaturated or aromatic;
each of R$^3$ and R$^4$ is independently hydrogen or C$_{1-5}$ alkyl;
each of R$^5$ and R$^6$ is independently hydrogen, C$_{1-5}$ alkyl, C$_{2-5}$ alkenyl, C$_{1-5}$ alkoxy, C$_{1-5}$ alkylthio, halogen, or a 4-7 membered carbocyclyl or heterocyclyl;
alternatively, R$^5$ and R$^6$ are taken together to form a 5- to 7-membered carbocyclic or heterocyclic ring, which ring is unsaturated or aromatic, and which ring is optionally substituted with between one and three substituents independently selected from halo, cyano, amino, nitro, R$^{40}$, R$^{40}$O—, R$^{40}$S—, R$^{40}$O(C$_{1-5}$ alkylene)-, R$^{40}$O(C=O)—, R$^{40}$(C=O)—, R$^{40}$(C=S)—, R$^{40}$(C=O)O—, R$^{40}$O(C=O)(C=O)—, R$^{40}$SO$_2$, NHR$^{62}$(C=NH)—, NHR$^{62}$SO$_2$—, and NHR$^{62}$(C=O)—;
R$^{40}$ is H, C$_{1-5}$ alkyl, C$_{2-5}$ alkenyl, phenyl, benzyl, phenethyl, C$_{1-5}$ heterocyclyl, (C$_{1-5}$ heterocyclyl)C$_{1-5}$ alkylene, amino, or mono- or di(C$_{1-5}$ alkyl)amino, or R$^{58}$OR$^{59}$—, wherein R$^{58}$ is H, C$_{1-5}$ alkyl, C$_{2-5}$ alkenyl, phenyl, benzyl, phenethyl, C$_{1-5}$ heterocyclyl, or (C$_{1-5}$ heterocyclyl)C$_{1-6}$ alkylene and R$^{59}$ is C$_{1-5}$ alkylene, phenylene, or divalent C$_{1-5}$ heterocyclyl; and
R$^{62}$ can be H in addition to the values for R$^{40}$;
R$^7$ is hydrogen, C$_{1-5}$ alkyl, C$_{3-5}$ alkenyl, phenyl, naphthyl, C$_{1-5}$ heterocyclyl, C$_{2-8}$ acyl, aroyl, R$^{27}$OC=O, R$^{28}$R$^{29}$NC=O, R$^{27}$SO, R$^{27}$SO$_2$, or R$^{28}$R$^{29}$NSO$_2$;
R$^8$ is hydrogen, C$_{1-5}$ alkyl, C$_{3-5}$ alkenyl, phenyl, or C$_{1-5}$ heterocyclyl;
alternatively, R$^7$ and R$^8$ are taken together to form an optionally substituted 4- to 7-membered heterocyclic ring, which ring is saturated, unsaturated or aromatic;
R$^9$ is C$_{1-5}$ alkyl, phenyl, naphthyl, or C$_{1-5}$ heterocyclyl;
R$^{21}$ is hydrogen, C$_{1-5}$ alkyl, C$_{3-5}$ alkenyl, phenyl, naphthyl, C$_{1-5}$ heterocyclyl, C$_{2-8}$ acyl, aroyl, R$^{30}$OC=O, R$^{31}$R$^{32}$NC=O, R$^{30}$SO, R$^{30}$SO$_2$, or R$^{31}$R$^{32}$NSO$_2$;
R$^{22}$ is hydrogen, C$_{1-5}$ alkyl, C$_{3-5}$ alkenyl, phenyl, or C$_{1-5}$ heterocyclyl;
alternatively, R$^{21}$ and R$^{22}$ are taken together to form an optionally substituted 4- to 7-membered heterocyclic ring, which ring is saturated, unsaturated or aromatic;
each of R$^{23}$, R$^{26}$, R$^{27}$, R$^{30}$, R$^{33}$, R$^{44}$, R$^{45}$, and R$^{50}$ is C$_{1-5}$ alkyl, phenyl, naphthyl, or C$_{1-5}$ heterocyclyl;
R$^{24}$ is hydrogen, C$_{1-5}$ alkyl, C$_{3-5}$ alkenyl, phenyl, naphthyl, C$_{1-5}$ heterocyclyl, C$_{2-8}$ acyl, aroyl, R$^{33}$OC=O, R$^{34}$R$^{35}$NC=O, R$^{33}$SO, R$^{33}$SO$_2$, or R$^{34}$R$^{35}$NSO$_2$;
R$^{25}$ is hydrogen, C$_{1-5}$ alkyl, C$_{3-5}$ alkenyl, phenyl, or C$_{1-5}$ heterocyclyl;
alternatively, R$^{24}$ and R$^{25}$ are taken together to form an optionally substituted 4- to 7-membered heterocyclic ring, which ring is saturated, unsaturated or aromatic;
each of R$^{10}$ and R$^{11}$ is independently hydrogen, C$_{1-5}$ alkyl, C$_{2-5}$ alkenyl, phenyl, or C$_{1-5}$ heterocyclyl;
alternatively, R$^{10}$ and R$^{11}$ are taken together to form an optionally substituted 4- to 7-membered heterocyclic ring, which ring is saturated, unsaturated or aromatic;
each of R$^{28}$, R$^{29}$, R$^{31}$, R$^{32}$, R$^{34}$, R$^{35}$, R$^{46}$, R$^{47}$, R$^{51}$ and R$^{52}$ is independently hydrogen, C$_{1-5}$ alkyl, phenyl, or C$_{1-5}$ heterocyclyl;
alternatively, R$^{28}$ and R$^{29}$, R$^{31}$ and R$^{32}$, R$^{34}$ and R$^{35}$, R$^{46}$ and R$^{47}$, or R$^{51}$ and R$^{52}$, independently, can be taken together to form an optionally substituted 4- to 7-membered heterocyclic ring, which ring may be saturated, unsaturated or aromatic;
n is 2;
G represents C$_{3-6}$ alkenediyl or C$_{3-6}$ alkanediyl, optionally substituted with hydroxy, halogen, C$_{1-5}$ alkyl, C$_{1-5}$ alkoxy, oxo, hydroximino, CO$_2$R$^{60}$, R$^{60}$R$^{61}$NCO$_2$, (L)-C$_{1-4}$ alkylene-, (L)-C$_{1-5}$ alkoxy, N$_3$, or [(L)-C$_{1-5}$ alkylene]amino;
each of R$^{60}$ and R$^{61}$ is independently hydrogen, C$_{1-5}$ alkyl, C$_{3-5}$ alkenyl, phenyl, benzyl, phenethyl, or C$_{1-5}$ heterocyclyl; alternatively, R$^{60}$ and R$^{61}$ are taken together to form an optionally substituted 4- to 7-membered heterocyclic ring, which ring is saturated, unsaturated or aromatic;
L is amino, mono- or di-C$_{1-5}$ alkylamino, pyrrolidinyl, morpholinyl, piperidinyl, homopiperidinyl, or piperazinyl, where available ring nitrogens may be optionally substituted with C$_{1-5}$ alkyl, benzyl, C$_{2-5}$ acyl, C$_{1-5}$ alkylsulfonyl, or C$_{1-5}$ alkyloxycarbonyl;
X is nitrogen or R$^{12}$C;
Y is nitrogen or R$^{13}$C;
Z is nitrogen or R$^{14}$C;
R$^{12}$ is hydrogen, halogen, C$_{1-5}$ alkoxy, C$_{1-5}$ alkyl, C$_{2-5}$ alkenyl, cyano, nitro, R$^{21}$R$^{22}$N, C$_{2-8}$ acyl, C$_{1-5}$ haloalkyl, C$_{1-5}$ heterocyclyl, (C$_{1-5}$ heterocyclyl)C$_{1-5}$ alkylene, R$^{23}$OC=O, R$^{23}$O(C=O)NH—, R$^{23}$SO, $R^{22}NHCO$—$R^{22}NH(C=O)NH$—, $R^{23}(C_{1-4}$ alkylene)NHCO—, $R^{23}SO_2$, or $R^{23}SO_2NH$—;

$R^{13}$ is hydrogen, halogen, $C_{1-5}$ alkoxy, $C_{1-5}$ alkyl, $C_{2-5}$ alkenyl, cyano, nitro, $R^{42}R^{43}N$, $C_{2-8}$ acyl, $C_{1-5}$ haloalkyl, $C_{1-5}$ heterocyclyl, $(C_{1-5}$ heterocyclyl)$C_{1-5}$ alkylene, $R^{44}OC=O$, $R^{44}O(C=O)NH$—, $R^{44}SO$, $R^{43}NHCO$—$R^{43}NH(C=O)NH$—, $R^{44}(C_{1-4}$ alkylene)NHCO—, $R^{44}SO_2$, or $R^{44}SO_2NH$—;

$R^{14}$ is hydrogen, halogen, $C_{1-5}$ alkoxy, $C_{1-5}$ alkyl, $C_{2-5}$ alkenyl, cyano, nitro, $R^{24}R^{25}N$, $C_{2-8}$ acyl, $C_{1-5}$ haloalkyl, $C_{1-5}$ heterocyclyl, $(C_{1-5}$ heterocyclyl)$C_{1-5}$ alkylene, $R^{26}OC=O$, $R^{26}O(C=O)NH$—, $R^{26}SO$, $R^{25}NHCO$—$R^{25}NH(C=O)NH$—, $R^{26}(C_{1-4}$ alkylene)NHCO—, $R^{26}SO_2$, or $R^{26}SO_2NH$—;

alternatively, $R^{12}$ and $R^{13}$ or $R^{12}$ and $R^2$ or $R^{13}$ and $R^{14}$ are taken together to form an optionally substituted 5- to 6-membered carbocyclic or heterocyclic ring, which ring is unsaturated or aromatic;

Ar represents a monocyclic or bicyclic aryl or heteroaryl ring, optionally substituted with between 1 and 3 substituents selected from halogen, $C_{1-5}$ alkoxy, $C_{1-5}$ alkyl, $C_{2-5}$ alkenyl, cyano, azido, nitro, $R^{15}R^{16}N$, $R^{17}SO_2$, $R^{17}S$, $R^{17}SO$, $R^{17}OC=O$, $R^{15}R^{16}NC=O$, $C_{1-5}$ haloalkyl, $C_{1-5}$ haloalkoxy, $C_{1-5}$ haloalkylthio, and $C_{1-5}$ alkylthio;

$R^{15}$ is hydrogen, $C_{1-5}$ alkyl, $C_{3-5}$ alkenyl, phenyl, benzyl, $C_{1-5}$ heterocyclyl, $C_{2-8}$ acyl, aroyl, $R^{53}OC=O$, $R^{54}R^{55}NC=O$, $R^{53}S$, $R^{53}SO$, $R^{53}SO_2$, or $R^{54}R^{55}NSO_2$;

$R^{16}$ is hydrogen, $C_{1-5}$ alkyl, $C_{3-5}$ alkenyl, phenyl, benzyl, or $C_{1-5}$ heterocyclyl;

alternatively, $R^{15}$ and $R^{16}$ are taken together to form an optionally substituted 4- to 7-membered heterocyclic ring, which ring is saturated, unsaturated or aromatic;

each of $R^{17}$ and $R^{53}$ is $C_{1-5}$ alkyl, phenyl, or $C_{1-5}$ heterocyclyl;

each of $R^{54}$ and $R^{55}$ is independently hydrogen, $C_{1-5}$ alkyl, $C_{2-5}$ alkenyl, phenyl, benzyl, or $C_{1-5}$ heterocyclyl;

alternatively, $R^{54}$ and $R^{55}$ are taken together to form an optionally substituted 4- to 7-membered heterocyclic ring, which ring is saturated, unsaturated or aromatic;

W represents $SO_2$, $C=O$, $CHR^{20}$, or a covalent bond; or W and $R^1$, taken together with the 6-membered ring to which they are both attached, form one of the following two formulae:

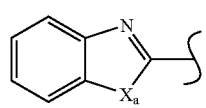
(I)(a)

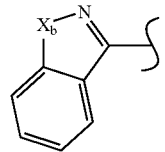
(I)(b)

wherein $X_a$ is O, S, or N; and $X_b$ is O, S or $SO_2$;

$R^{20}$ is hydrogen, $C_{1-5}$ alkyl, phenyl, benzyl, naphthyl, or $C_{1-5}$ heterocyclyl;

$R^{42}$ is hydrogen, $C_{1-5}$ alkyl, $C_{3-5}$ alkenyl, phenyl, naphthyl, $C_{1-5}$ heterocyclyl, $C_{2-8}$ acyl, aroyl, $R^{45}OC=O$, $R^{46}R^{47}NC=O$, $R^{45}SO$, $R^{45}SO_2$, or $R^{46}R^{47}NSO_2$;

$R^{43}$ is hydrogen, $C_{1-5}$ alkyl, $C_{3-5}$ alkenyl, phenyl, or $C_{1-5}$ heterocyclyl;

alternatively, $R^{42}$ and $R^{43}$ are taken together to form an optionally substituted 4- to 7-membered heterocyclic ring, which ring is saturated, unsaturated or aromatic;

$R^{44}$ is $C_{1-5}$ alkyl, $C_{2-5}$ alkenyl, phenyl, naphthyl, or $C_{1-5}$ heterocyclyl;

$R^{48}$ is hydrogen, $C_{1-5}$ alkyl, $C_{3-5}$ alkenyl, phenyl, naphthyl, $C_{1-5}$ heterocyclyl, $C_{2-8}$ acyl, aroyl, $R^{50}OC=O$, $R^{51}R^{52}NC=O$, $R^{50}SO$, $R^{50}SO_2$, or $R^{51}R^{52}NSO_2$;

$R^{49}$ is hydrogen, $C_{1-5}$ alkyl, $C_{3-5}$ alkenyl, phenyl, or $C_{1-5}$ heterocyclyl;

alternatively, $R^{48}$ and $R^{49}$ are taken together to form an optionally substituted 4- to 7-membered heterocyclic ring, which ring is saturated, unsaturated or aromatic; and wherein each of the above hydrocarbyl or heterocarbyl groups, unless otherwise indicated, and in addition to any specified substituents, is optionally and independently substituted with between 1 and 3 substituents selected from methyl, halomethyl, hydroxymethyl, halo, hydroxy, amino, nitro, cyano, $C_{1-5}$ alkyl, $C_{1-5}$ alkoxy, —COOH, $C_{2-6}$ acyl, [di($C_{1-4}$ alkyl)amino]$C_{2-5}$ alkylene, [di($C_{1-4}$ alkyl)amino]$C_{2-5}$ alkyl-NH—CO—, and $C_{1-5}$ haloalkoxy;

or a pharmaceutically acceptable salt, ester, or amide thereof.

2. A compound of claim 1, wherein $R^1$ is hydrogen, halogen, $C_{1-5}$ alkoxy, hydroxy, $C_{1-5}$ alkyl, cyano, nitro, $R^7R^8N$, $C_{2-8}$ acyl, or $R^{10}R^{11}NSO_2$.

3. A compound of claim 2, wherein $R^1$ is halogen, cyano, nitro, $R^7R^8N$, or $R^{10}R^{11}NSO_2$.

4. A compound of claim 1, wherein $R^2$ is hydrogen.

5. A compound of claim 1, wherein each of $R^3$ and $R^4$ is independently hydrogen or $C_{1-3}$ alkyl.

6. A compound of claim 5, wherein one of $R^3$ and $R^4$ is hydrogen.

7. A compound of claim 6, wherein each of $R^3$ and $R^4$ is hydrogen.

8. A compound of claim 1, wherein one of $R^5$ and $R^6$ is hydrogen and the other is a 5-7 membered carbocyclyl or heterocyclyl, optionally substituted.

9. A compound of claim 1, wherein $R^5$ and $R^6$ taken together form a six-membered heterocyclyl.

10. A compound of claim 8, wherein $R^5$ and $R^6$ taken together form pyridinyl, pyrimidinyl, or piperazinyl, optionally N-substituted with $R^{40}O(C=O)(C=O)$—, $R^{40}SO_2$, $R^{40}NHCO_2$, $R^{40}(C=O)$— or $R^{40}N(C=O)$—.

11. A compound of claim 1, wherein each of $R^7$, $R^8$, $R^{21}$, $R^{22}$, $R^{24}$, and $R^{25}$ is independently hydrogen or $C_{1-5}$ alkyl; or, independently, each of $R^7$ and $R^8$, $R^{21}$ and $R^{22}$, and $R^{24}$ and $R^{25}$ are taken together to form an optionally substituted 4- to 7-membered heterocyclic ring, which ring is saturated, unsaturated or aromatic.

12. A compound of claim 11, wherein at least one of $R^7$ and $R^8$, $R^{21}$ and $R^{22}$, and $R^{24}$ and $R^{25}$ taken together, is morpholinyl, piperidinyl, or pyrrolidinyl.

13. A compound of claim 1, wherein $R^9$, $R^{23}$, $R^{26}$, and $R^{27}$ are each independently $C_{1-5}$ alkyl.

14. A compound of claim 1, wherein G is $C_{3-4}$ alkanediyl, optionally substituted with hydroxy, (L)-$C_{1-5}$ alkyloxy-, or [(L)-$C_{1-5}$ alkylene]amino-.

15. A compound of claim 14, wherein G is $C_3$ alkanediyl, optionally substituted with hydroxy, (L)-$C_{1-5}$ alkyloxy-, or [(L)-$C_{1-5}$ alkylene]amino-.

16. A compound of claim 1, wherein X is nitrogen.

17. A compound of claim 1, wherein Y is $CR^{13}$.

18. A compound of claim 1, wherein Z is $CR^{14}$.

19. A compound of claim 18, wherein X is CH.

20. A compound of claim 1, wherein $R^{12}$ is hydrogen, $R^{23}O(C=O)NH-$, $R^{22}NH(C=O)NH-$, $R^{23}SO_2NH$, $R^{23}SO$, or $R^{23}SO_2$, and $R^{13}$ is hydrogen, $R^{44}O(C=O)NH-$, $R^{43}NH(C=O)NH-$, $R^{44}SO_2NH$, $R^{44}SO$, or $R^{44}SO_2$.

21. A compound of claim 1, wherein $R^{14}$ is hydrogen, halogen, $C_{1-5}$ alkoxy, $C_{1-5}$ alkyl, cyano, nitro, $R^{26}O(C=O)NH-$, $R^{25}NH(C=O)NH-$, $R^{26}SO_2NH$, or $R^{24}R^{25}N$.

22. A compound of claim 21, wherein $R^{14}$ is halogen, $R^{26}O(C=O)NH-$, $R^{25}NH(C=O)NH-$, $R^{26}SO_2NH$, or $R^{24}R^{25}N$.

23. A compound of claim 1, wherein Ar represents a monocyclic ring, optionally substituted with between 1 and 2 substituents selected independently from halogen, $C_{1-5}$ alkyl, cyano, nitro, $R^{15}R^{16}N$, $CF_3$, and $OCF_3$.

24. A compound of claim 23, wherein Ar is a six membered ring substituted with between 1 and 2 substituents selected from halo, $CF_3$, and $OCF_3$, said substitutent or substitutents being at the 4-position or at the 3- and 4-positions, respectively.

25. A compound of claim 1, wherein W is $SO_2$, C=O, or $CHR^{20}$.

26. A compound of claim 1, wherein W is a covalent bond.

27. A compound of claim 1, wherein W and $R^1$ taken together are formula (I)(a).

28. A compound of claim 1, wherein W and $R^1$ taken together are formula (I)(b).

29. A compound of claim 1, wherein one of $R^3$ and $R^4$ is hydrogen; Ar represents a monocyclic ring, optionally substituted with between 1 and 2 substituents selected from halogen, $C_{1-5}$ alkyl, cyano, nitro, $R^{15}R^{16}N$, $CF_3$, and $OCF_3$; $R^{12}$ is hydrogen, $R^{23}SO$, or $R^{23}SO_2$; $R^{13}$ is hydrogen, $R^{44}SO$, or $R^{44}SO_2$; $R^{14}$ is hydrogen, halogen, $C_{1-5}$ alkoxy, $C_{1-5}$ alkyl, cyano, nitro, or $R^{24}R^{25}N$; and G is $C_{3-4}$ alkanediyl, optionally substituted with hydroxy, $C_{1-3}$ alkyl, (L)-$C_{1-5}$ alkyloxy, or [(L)-$C_{1-5}$ alkylene]amino-.

30. A compound of claim 1, wherein each of $R^3$ and $R^4$ is hydrogen; Ar represents a six membered ring, optionally substituted with between 1 and 2 substituents selected from halogen, $C_{1-5}$ alkyl, cyano, nitro, $R^{15}R^{16}N$, $CF_3$, and $OCF_3$; $R^{12}$ is hydrogen, $R^{23}SO$, or $R^{23}SO_2$; $R^{13}$ is hydrogen, $R^{44}SO$, or $R^{44}SO_2$; $R^{14}$ is hydrogen, halogen, $C_{1-5}$ alkoxy, $C_{1-5}$ alkyl, cyano, nitro, or $R^{24}R^{25}N$; and G is $C_3$ alkanediyl, optionally substituted with hydroxy, (L)-$C_{1-5}$ alkyloxy-, or (L)-$C_{1-5}$ alkylamino.

31. A compound of claim 30 wherein Ar is phenyl.

32. A compound of claim 31, wherein W and $R^1$ taken together are formula (I)(b).

33. A pharmaceutical composition comprising a compound of claim 1, 30, or 31 and a pharmaceutically acceptable carrier.

34. A method for treating an autoimmune disease, or inhibiting the progression of an autoimmune disease, in a subject, said method comprising administering to the subject a therapeutically effective amount of a pharmaceutical composition comprising a compound of claim 1, 30, or 31, wherein the autoimmune disease is selected from lupus, rheumatoid arthritis, and asthma.

35. A method of claim 34, wherein the autoimmune disease is asthma.

36. A method for treating the proteolytic activity of human cathepsin S comprising contacting human cathepsin S with a compound of claim 1.

37. A method of claim 36, wherein the human cathepsin S is in a human subject.

38. A method of claim 37, wherein the human subject is suffering from an autoimmune disease selected from lupus, rheumatoid arthritis, and asthma.

* * * * *